US012605039B2

(12) United States Patent
Jørgensen et al.

(10) Patent No.: US 12,605,039 B2
(45) Date of Patent: Apr. 21, 2026

(54) ENDOSCOPE IMAGE PROCESSING DEVICE

(71) Applicant: AMBU A/S, Ballerup (DK)

(72) Inventors: Andreas Härstedt Jørgensen, Rødovre
(DK); Finn Sonnenborg, Frederikssund
(DK); Dana Marie Yu, Ballerup (DK);
Lee Herluf Lund Lassen, Måløv (DK);
Alejandro Alonso Díaz, Ballerup (DK);
Josefine Dam Gade, Frederiksberg
(DK)

(73) Assignee: AMBU A/S, Ballerup (DK)

( * ) Notice: Subject to any disclaimer, the term of this
patent is extended or adjusted under 35
U.S.C. 154(b) by 489 days.

(21) Appl. No.: 18/074,436

(22) Filed: Dec. 2, 2022

(65) Prior Publication Data

US 2023/0172428 A1     Jun. 8, 2023

(30) Foreign Application Priority Data

Dec. 3, 2021    (EP) ..................................... 21212282
Dec. 3, 2021    (EP) ..................................... 21212292
(Continued)

(51) Int. Cl.
     *A61B 1/00*         (2006.01)
     *A61B 5/00*         (2006.01)
(52) U.S. Cl.
     CPC .... *A61B 1/000096* (2022.02); *A61B 1/00045*
     (2013.01); *A61B 5/7267* (2013.01); *G06T*
     *2207/20084* (2013.01)
(58) Field of Classification Search
     CPC ............................................. A61B 1/000096
     See application file for complete search history.

(56) References Cited

U.S. PATENT DOCUMENTS 7,641,609 B2    1/2010  Ohnishi et al.
7,894,648 B2    2/2011  De Groen et al.
                (Continued)

FOREIGN PATENT DOCUMENTS

CN        108042092 A    5/2018
EP          1466552 B1   1/2007
                (Continued)

OTHER PUBLICATIONS

European Search Report for EP Patent Application No. 21212282.4,
Issued on May 18, 2022, 8 pages.
(Continued)

*Primary Examiner* — Benjamin O Dulaney
(74) *Attorney, Agent, or Firm* — Faegre Drinker Biddle &
Reath LLP

(57)                ABSTRACT
An image processing device including a housing and a
processing circuit in the housing, the processing circuit
including a processor and memory, the memory including a
neural network model and proximity suppression logic, the
neural network model comprising a single-pass neural net-
work model trained with training images corresponding to
an endoscopic procedure and defining anatomic references
observable in the training images, wherein the neural net-
work model is configured to process images, to detect the
anatomic references in the images, and to output a set of
anatomic references including identifiers and confidence
values representing the likelihoods that the anatomic refer-
ence identifiers are correct, and wherein the proximity
suppression logic is configured to change the confidence
values of the anatomic references in the set of anatomic
references based on a prior position of the endoscope to
identify an anatomic reference indicative of the current
position of the endoscope.

16 Claims, 23 Drawing Sheets

(30) Foreign Application Priority Data

| | | | |
|---|---|---|---|
| Dec. 3, 2021 | (EP) | .................................. | 21212304 |
| Dec. 3, 2021 | (EP) | .................................. | 21212319 |
| Dec. 3, 2021 | (EP) | .................................. | 21212323 |

(56) References Cited

U.S. PATENT DOCUMENTS

| | | | |
|---|---|---|---|
| 8,064,666 | B2 | 11/2011 | Bayer |
| 8,353,816 | B2 | 1/2013 | Shimizu et al. |
| 9,044,185 | B2 | 6/2015 | Bayer |
| 9,055,881 | B2 | 6/2015 | Gilboa et al. |
| 9,443,132 | B2 | 9/2016 | Linguraru et al. |
| 9,613,418 | B2 | 4/2017 | Bayer |
| 9,760,807 | B2 | 9/2017 | Zhou et al. |
| 9,978,142 | B2 | 5/2018 | Chi et al. |
| 10,321,803 | B2 | 6/2019 | Gilboa et al. |
| 10,354,382 | B2 | 7/2019 | Bayer |
| 10,646,288 | B2 | 5/2020 | Yeung et al. |
| 10,682,108 | B1 | 6/2020 | Ma et al. |
| 10,736,497 | B2 | 8/2020 | Nicolau et al. |
| 10,888,248 | B2 | 1/2021 | Zhao et al. |
| 11,045,075 | B2 | 6/2021 | Komp |
| 11,065,079 | B2 | 7/2021 | Wolf et al. |
| 11,439,469 | B2 | 9/2022 | Poltaretskyi et al. |
| 11,707,255 | B2 * | 7/2023 | Salgaonkar .............. A61B 8/12 600/463 |
| 12,525,145 | B2 | 1/2026 | Jørgensen et al. |
| 2011/0032347 | A1 | 2/2011 | Lacey et al. |
| 2011/0301447 | A1 | 12/2011 | Park et al. |
| 2012/0033062 | A1 | 2/2012 | Bayer |
| 2012/0062714 | A1 | 3/2012 | Liu et al. |
| 2012/0123250 | A1 * | 5/2012 | Pang ....................... G06T 7/277 600/424 |
| 2012/0130171 | A1 | 5/2012 | Barak et al. |
| 2013/0237811 | A1 | 9/2013 | Mihailescu et al. |
| 2014/0180063 | A1 | 6/2014 | Zhao et al. |
| 2015/0054929 | A1 | 2/2015 | Ito et al. |
| 2016/0206228 | A1 | 7/2016 | Angulo et al. |
| 2016/0287064 | A1 | 10/2016 | Svendsen et al. |
| 2017/0296032 | A1 * | 10/2017 | Li ............................. A61B 6/03 |
| 2017/0360403 | A1 | 12/2017 | Rothberg et al. |
| 2018/0296281 | A1 | 10/2018 | Yeung et al. |
| 2019/0034800 | A1 | 1/2019 | Shiratani |
| 2019/0125173 | A1 * | 5/2019 | Lee ....................... G06T 7/0012 |
| 2019/0183587 | A1 * | 6/2019 | Rafii-Tari ............... A61B 34/20 |
| 2019/0340761 | A1 | 11/2019 | Bayer |
| 2019/0380781 | A1 | 12/2019 | Tsai et al. |
| 2020/0029789 | A1 | 1/2020 | Hirakawa |
| 2020/0043613 | A1 | 2/2020 | Zhang et al. |
| 2020/0193603 | A1 | 6/2020 | Golden et al. |
| 2020/0237187 | A1 | 7/2020 | Cantrall et al. |
| 2020/0279373 | A1 | 9/2020 | Hussain et al. |
| 2020/0297444 | A1 * | 9/2020 | Camarillo .............. G16H 30/40 |
| 2020/0364880 | A1 | 11/2020 | Yu et al. |
| 2020/0367721 | A1 | 11/2020 | Yue et al. |
| 2021/0038321 | A1 | 2/2021 | Toporek et al. |
| 2021/0251602 | A1 * | 8/2021 | Chen ...................... A61B 8/085 |
| 2022/0409291 | A1 * | 12/2022 | Shochat .................. A61B 34/10 |
| 2023/0044620 | A1 * | 2/2023 | Shochat ................ G06T 7/0012 |
| 2023/0045451 | A1 | 2/2023 | Cho |
| 2023/0147689 | A1 | 5/2023 | Buras et al. |
| 2023/0233098 | A1 | 7/2023 | Jørgensen et al. |
| 2024/0225584 | A1 * | 7/2024 | Kopel .................... A61B 34/20 |

FOREIGN PATENT DOCUMENTS

| | | | |
|---|---|---|---|
| EP | 2276391 | A1 | 1/2011 |
| EP | 2427867 | A1 | 3/2012 |
| EP | 1761160 | B1 | 12/2012 |
| EP | 2906133 | A1 | 8/2015 |
| EP | 3068281 | B1 | 1/2018 |
| EP | 2996557 | B1 | 5/2019 |
| EP | 3920189 | A1 | 12/2021 |
| KR | 10-2037303 | B1 | 10/2019 |
| WO | 2006/138504 | A2 | 12/2006 |
| WO | 2015015310 | A2 | 2/2015 |
| WO | 2018144698 | A1 | 8/2018 |
| WO | 2018188466 | A1 | 10/2018 |
| WO | 2018195221 | A1 | 10/2018 |
| WO | 2019/174953 | A1 | 9/2019 |
| WO | 2019/232236 | A1 | 12/2019 |
| WO | 2020114037 | A1 | 6/2020 |
| WO | 2020/160567 | A1 | 8/2020 |
| WO | 2020201772 | A1 | 10/2020 |
| WO | 2020215593 | A1 | 10/2020 |
| WO | 2021011190 | A1 | 1/2021 |
| WO | 2021/194872 | A1 | 9/2021 |
| WO | 2021/245222 | A1 | 12/2021 |

OTHER PUBLICATIONS

European Search Report for EP Patent Application No. 21212292.3, Issued on Jun. 2, 2022, 10 pages.

European Search Report for EP Patent Application No. 21212304.6, Issued on Jun. 8, 2022, 12 pages.

European Search Report for EP Patent Application No. 21212319.4, Issued on May 10, 2022, 7 pages.

European Search Report for EP Patent Application No. 21212323.6, Issued on May 20, 2022, 8 pages.

Hwang et al., "Automatic measurement of quality metrics for colonoscopy videos," Proceedings of the 13th annual ACM international conference on Multimedia, Nov. 6, 2005, pp. 912-921.

International Search Report and Written Opinion received for PCT Patent Application No. PCT/EP2021/064985, mailed on Aug. 6, 2021, 11 pages.

Mikada et al., "Three-dimensional posture estimation of robot forceps using endoscope with convolutional neural network," The International Journal of Medical Robotics and Computer Assisted Surgery, vol. 16, Issue 2, Jan. 8, 2020, pp. 1-9.

Li, Ying et al., "Development and validation of the artificial intelligence (AI)-based diagnostic model for bronchial lumen identification," Transl Lung Cancer Res 2022;11(11); pp. 2261-2274, Nov. 2022.

Chen, Chongxian et al., "Distinguishing bronchoscopically observed anatomical positions of airway under by convolutional neural network," Therapeutic Advances in Chronic Disease, vol. 14: 1-10; Published online Aug. 23, 2023.

Search report in European Application No. 22211097.5, dated May 3, 2023, 9 pages.

Wang, Chien-Yao et al., "YOLOv7: Trainable bag-of-freebies sets new state-of-the-art for real-time object detectors," Institute of Information Science, Academia Sinica, Taiwan, [2207.02696] YOLOv7: Trainable bag-of-freebies sets new state-of-the-art for real-time object detectors, Jul. 6, 2022, 17 pages.

Ronneberger, Olaf et al., "U-Net: Convolutional Networks for Biomedical Image Segmentation," Computer Science Department and BIOSS Centre for Biological Signalling Studies, University of Freiburg, Germany, May 18, 2015, arXiv:1505.04597 [cs.CV], 8 pages.

He, Kaiming et al., "Mask R-CNN," Facebook AI Research (FAIR), arXiv:1703.06870 [cs.CV], Jan. 24, 2018, 12 pages.

Office Action issued in related U.S. Appl. No. 18/206,935 mailed Oct. 21, 2025; 26 pages.

* cited by examiner

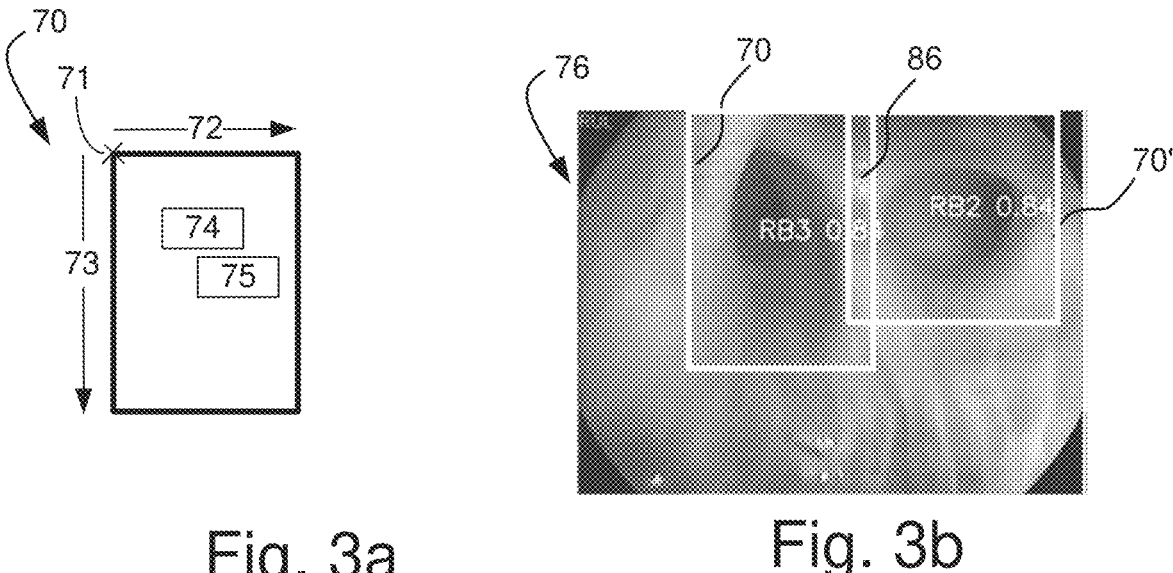
Fig. 3a
Fig. 3b
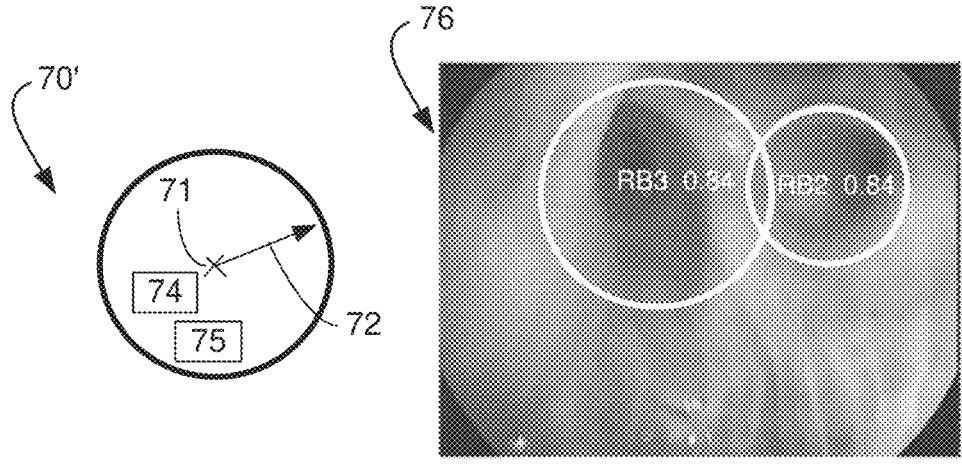
Fig. 4a
Fig. 4b

400

Obtain stream of images captured
by the image capturing device — 402

Process the stream of images to
estimate the location of a lumen in
the image — 404

Determine  a quality measure
based on the estimated location of
the  lumen — 406

432          430

434

500

Obtain an image captured by the image
capturing device — 502

Process the image to estimate the location of
one or more lumens in the image — 504

Determine a quality measure based on the
estimated location of the one or more lumens — 506

542

540

544

552

550

554

556

630
632
650

640

630
632
650

640
652

ENDOSCOPE IMAGE PROCESSING DEVICE

CROSS-REFERENCE TO RELATED APPLICATIONS

This application claims priority from and the benefit of European Patent Applications Nos. EP 2121 2282, filed Dec. 3, 2021, EP 2121 2292, filed Dec. 3, 2021, EP 2121 2304, filed Dec. 3, 2021, EP 2121 2319, filed Dec. 3, 2021, and EP 2121 2323, filed Dec. 3, 2021, which are incorporated by reference herein in their entirety.

TECHNICAL FIELD

The present disclosure relates to a method implemented with a video processing apparatus for assisting a user during an endoscopic procedure. More specifically, the method includes the application of object detection logic to determine a location of the endoscope relative to the patient.

BACKGROUND

Examination of human cavities, such as human airways, with an endoscope may be carried out to determine whether a patient has disease, a tumor, an infection, or the like, and in some cases samples may be taken/removed from the human cavity. For instance, bronchoscopies or colonoscopies may be carried out to examine whether a patient has a lung or colon disease, respectively, a tumour, or the like. The endoscope typically comprises an image sensor, such as a camera, at a distal end of the endoscope to be inserted into the patient and connected to a display so as to provide the medical personnel with a view of the part of the airways, in which the distal end of the endoscope is positioned.

Typically, when an endoscopic examination of a human cavity, i.e. an endoscopic procedure, is carried out, the medical personnel will need to search through various parts of the human cavity. This often includes moving the endoscope into a part of the human cavity and back to an earlier position to again move the endoscope into another part of the human cavity. For instance, human airways have a branched structure and when one branch of a branching has been examined, the endoscope will typically be retracted to a branching and subsequently moved from that branching into another branch of the branching. This may, however, be a challenging task as parts of the bronchial tree are very narrow and provide little space for the endoscope. Unintentionally colliding the endoscope with the bronchial wall may be very unpleasant for the patient and should be avoided. In other examinations, the endoscope may be re-inserted into a part of the human cavity, in which it has already been, to make further examination of the part of the human cavity.

Traditionally, when navigating the endoscope through the human cavity, the medical personnel rely on experience to navigate the endoscope through the human cavity based on images from a camera of the endoscope. In the human cavities, such as human airways or a colon, various parts thereof look identical, which may make it difficult for the medical personnel to identify the location of the endoscope in the human cavity. This increases the risk that a patient is not properly examined. This leads to a risk of mistakes, e.g. in that the desired parts of the human cavity are not examined or in that a part of the airways are mistaken for a different part in the cavity. This, in turn, increases a risk that the patient is not properly examined.

While medical personnel are often trained to perform the endoscope navigation using models of the human cavities, this training is often based on a "best practice" of an experienced person, such as a doctor, training a less experienced person. This, increases the risk of inconsistent and/or insufficient training, in turn leading to an increased risk of insufficient or incorrect examinations. Additionally, training on a phantom model is not optimal as the phantom model presents an idealized case with no tissue movement. Furthermore, the pressure of an actual clinical setting cannot be fully re-created. Furthermore, it may be difficult for the new medical personnel or trainers of the new medical personnel to properly evaluate their performance both when training on a phantom model and when training on real patients. Additionally, it may be difficult or too time consuming to document a procedure in sufficient detail.

Systems have been developed to assist the medical personnel in navigating the endoscope through the human cavity. The position of the endoscope may be found by firstly imaging the bronchial tree using CT or planar X-Ray, and then using a magnetic tracking system to determine the position of the endoscope in the CT image of a planar X-Ray image. The superDimension™ Navigation System from Medtronic is an example of such a system. However, reliance on external devices increases the complexity of the examination since the external devices must be controlled along with the endoscope.

The location of the endoscope may be determined using any method, such as magnetic tracking, and image-based techniques such as machine learning methods, e.g. as disclosed in commonly-owned PCT Publication No. WO2021245222A1, which is incorporated herein by reference.

On this background, it is desirable to provide a method, and a video processing apparatus, which at least mitigate some of the above-mentioned drawbacks.

SUMMARY

According to a first aspect, the present disclosure relates to an image processing device comprising a supervised single-pass neural network model trained to detect anatomic reference positions in images from an endoscope. Advantageously, using the supervised single-pass neural network model a physician can be assisted visually during navigation of the endoscope during the endoscopic procedure, both in an actual examination and using a phantom model for training of the physician. The visual assistance is based on the images generated by the endoscope and is provided using only the endoscope to generate the visual assistance. Therefore, the image processing device can be portable.

According to a second aspect, the present disclosure relates to examination and training methods implemented with an image processing device according to the first aspect.

According to a third aspect, the present disclosure relates to an endoscope system comprising an image processing device according to the first aspect and an endoscope connectable to the image processing device.

In the following, the term "image processing device" has the same meaning and is used interchangeably with the term "video processing apparatus."

The supervised single-pass neural network model may be referred to as a machine learning data architecture.

In some embodiments, the image processing device comprises proximity suppression logic operable to produce a subset of anatomic reference positions from a set of anatomic reference positions detected by the neural network model based on a prior position of the endoscope. Advantageously, use of the proximity suppression logic increases the confidences of the predicted anatomic reference positions relative to the confidences obtained without the proximity suppression logic with minimal computational costs.

In some embodiments, the image processing device is configured to estimate a position of an endoscope in a model of the human airways using a first machine learning data architecture trained to determine a set of anatomic reference positions, said image processing device comprising a processor operationally connectable to an image sensor of the endoscope, wherein the processor is configured to: obtain a stream of recorded images; continuously analyse the recorded images of the stream of recorded images using the first machine learning data architecture to determine if an anatomic reference position of a subset of anatomic reference positions, from the set of anatomic reference positions, has been reached; and where it is determined that the anatomic reference position has been reached, update the endoscope position based on the anatomic reference position.

In some embodiments, the image processing device is configured to estimate a position of an endoscope, said image processing device comprising: a processor operationally connectable to an image sensor of the endoscope; a first machine learning data architecture trained to determine a set of anatomic reference positions; and a model of human airways, wherein the processor is configured to: obtain from the image sensor of the endoscope a stream of recorded images during an endoscopic procedure; continuously analyse the recorded images of the stream of recorded images using the first machine learning data architecture to determine if the endoscope reached an anatomic reference position of a subset of anatomic reference positions from the set of anatomic reference positions, the subset comprising a plurality of anatomic reference positions; and where it is determined that the anatomic reference position has been reached, update the endoscope position based on the anatomic reference position and update the subset of anatomic reference positions.

In some embodiments, a method of recognising previously observed locations during an endoscopic procedure is provided, the method comprising: obtaining a stream of images from an image sensor of an endoscope during the endoscopic procedure; during the endoscopic procedure, building a database of previously observed locations based on images of the stream of images; and continuously comparing images of the stream of images with the database of previously observed locations to determine if an image of the stream of images is recorded from a previously observed location.

In some embodiments, the image processing device is configured to determine the location of an endoscope in a phantom model, the phantom model being a physical model of a cavity of a human body, wherein the image processing device comprises a processor operationally connectable to an image sensor of an endoscope, the processor being configured to: obtain a stream of images from the image sensor of the endoscope; continuously process images of the stream of images to determine if a predetermined reference position has been reached; in response to determining that the predetermined reference position has been reached, updating an estimated location of the endoscope.

In some embodiments, the image processing device is configured to estimate a quality measure of a endoscopic procedure performed using an endoscope, the endoscope comprising an image sensor, the image processing device comprising a processor operationally connectable to the image sensor, wherein the processor is configured to: obtain a stream of images captured by the image sensor of the endoscope; process the stream of images to estimate locations of a lumen in the stream of images, and determine a quality measure of the endoscopic procedure based on the estimated locations of the lumen.

In some embodiments, the image processing device is configured to estimate a quality measure of a bronchoscopy procedure performed using an endoscope, the endoscope comprising an image sensor, the image processing device comprising a processor operationally connectable to the image sensor, wherein the processor is configured to: obtain an image captured by the image sensor of the endoscope; process the image to estimate the location of one or more lumens in the image, and determine a quality measure of the bronchoscopy based on the estimated location of the one or more lumens.

In some embodiments, the image processing device is configured to document a bronchoscopy procedure performed using an endoscope, the endoscope comprising an image sensor, the image processing device comprising a processor operationally connectable to the image sensor, wherein the processor is configured to: obtain a model of the bronchial tree; obtain a stream of images captured by the image sensor of the endoscope; continuously obtain estimates of the location of the endoscope in the model of the bronchial tree during the bronchoscopy; and based on at least three estimates of the location of the endoscope in the model of the bronchial tree generate a report documenting the bronchoscopy procedure.

In some embodiments, the image processing device according to the first aspect is configured according to one or more of the embodiments of the image processing device enumerated above and image processing devices configured to implement the embodiments of the methods enumerated above.

BRIEF DESCRIPTION OF THE DRAWINGS

The foregoing embodiments of the image processing device and the method will now be described in greater detail with reference to non-limiting exemplary embodiments illustrated in the appended drawings, of which:

FIGS. 3a, 3b, 4a, and 4b illustrate outputs of an enhanced object detection logic operable to recognize anatomical features in images generated by the endoscope of FIG. 1b;

FIGS. 16*a-e* are schematic representations of images to illustrate how to assess a quality of the examination;

DETAILED DESCRIPTION

Figure 1A:
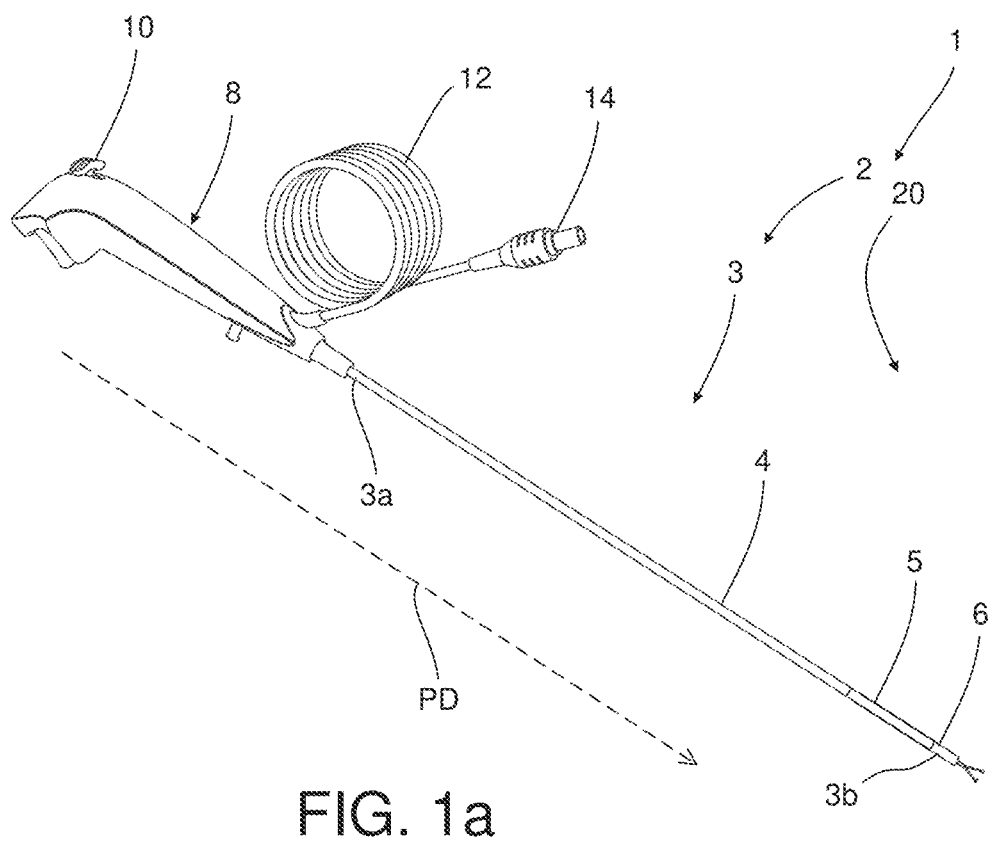
FIG. 1a shows a perspective view of an endoscope.
Figure 1B:
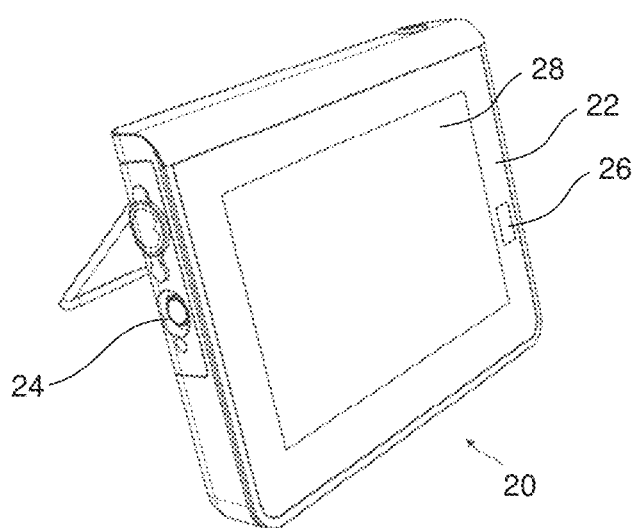
FIG. 1b shows a perspective view of a video processing apparatus to which the endoscope of FIG. 1a is connectable.

FIGS. 1*a* and 1*b* present a visualization system 1 including an endoscope 2 and a video processing apparatus 20. Referring first to FIG. 1*a*, an embodiment of the endoscope 2 comprises an elongated insertion cord 3 including an insertion tube 4, a bending section 5, and a distal tip 6. At the proximal end 3*a* of the insertion cord 3 an operating handle 8 is arranged. The operating handle 8 has a steering control lever 10 for manoeuvering the tip part 6 at the distal end 3*b* of the insertion cord 3 by means of a steering wire. The tip part 6 includes a housing accommodating a camera 15 including an image sensor 16 and one or more light emitting diodes (LEDs) 18, shown in FIG. 2. The image sensor 16 is configured to transmit an image signal through a cable 12 having a connector 14.

A positioning interface, or interface, functions to control the position of the insertion cord. The handle 8 is an example of a positioning interface and, unless stated otherwise, the terms are used interchangeably. The positioning interface also functions to provide the steering controls, e.g. knobs, levers, buttons, and the like, to steer the field of view of the camera and the elevator controls. Alternatively, a different positioning interface can be provided that is connected to the insertion cord and is detachably connected to a robotic arm. The insertion cord thus extends from the robotic arm, and the intrusive medical device is detachable from the robotic arm. The robotic arm responds to signals, including voice commands from an operator, to rotate, translate, and otherwise position the proximal end of the insertion cord, as an operator would do manually. The positioning interface can include control actuators, including manual control actuators. Alternatively or additionally, control actuators can be provided in or on the robotic arm or by the robotic system including the robotic arm, thereby potentially reducing the cost of the intrusive medical device. Example control actuators include single axis actuators, including linear motion actuators. A linear motion actuator may comprise a threaded rod coupled to a threaded nut portion, in which a motor rotates the rod to translate the nut portion.

In FIG. 1*b*, an embodiment of an image processing device, also referred to as video processing apparatus (VPA) 20, is presented. The VPA 20 in the present embodiment includes a housing 22 enclosing and supporting a display screen 28 and a video processing circuit 26. A cable socket 24 receives the connector 14 of the endoscope 2 to establish a signal communication between the image sensor 16 and the video processing circuit 26. The VPA 20 allow an operator to view an image captured by the image sensor. The image processing circuit 26 is described with reference to FIG. 2. A longitudinal direction is denoted by reference PD.

Variations of the VPA 20 can be provided with various features of the VPA 20 but including or excluding other features. For example, it might not be desirable to provide a video display screen with a touch screen, or it might be desirable to omit a display screen altogether. Omission of the display screen might be beneficial to take advantage of evolving video display technologies which improve resolution and reduce cost. Provision of exchangeable medical device interfaces allows for adoption of evolving image sensor and endoscope technologies, thus use of existing or future-developed external video displays could allow presentation of higher resolution or otherwise improved video. Use of external video displays could also leverage existing capital investments.

In all embodiments, the endoscope may be disposable and may not be intended to be cleaned and reused. Alternatively the endoscope may, in all embodiments, be re-usable. In some variations of the present embodiment, the endoscope and the VPA comprise wireless transceivers to exchange image data and configuration data. The endoscope may comprise a battery to power the image sensor and the LEDs.

Figure 2:
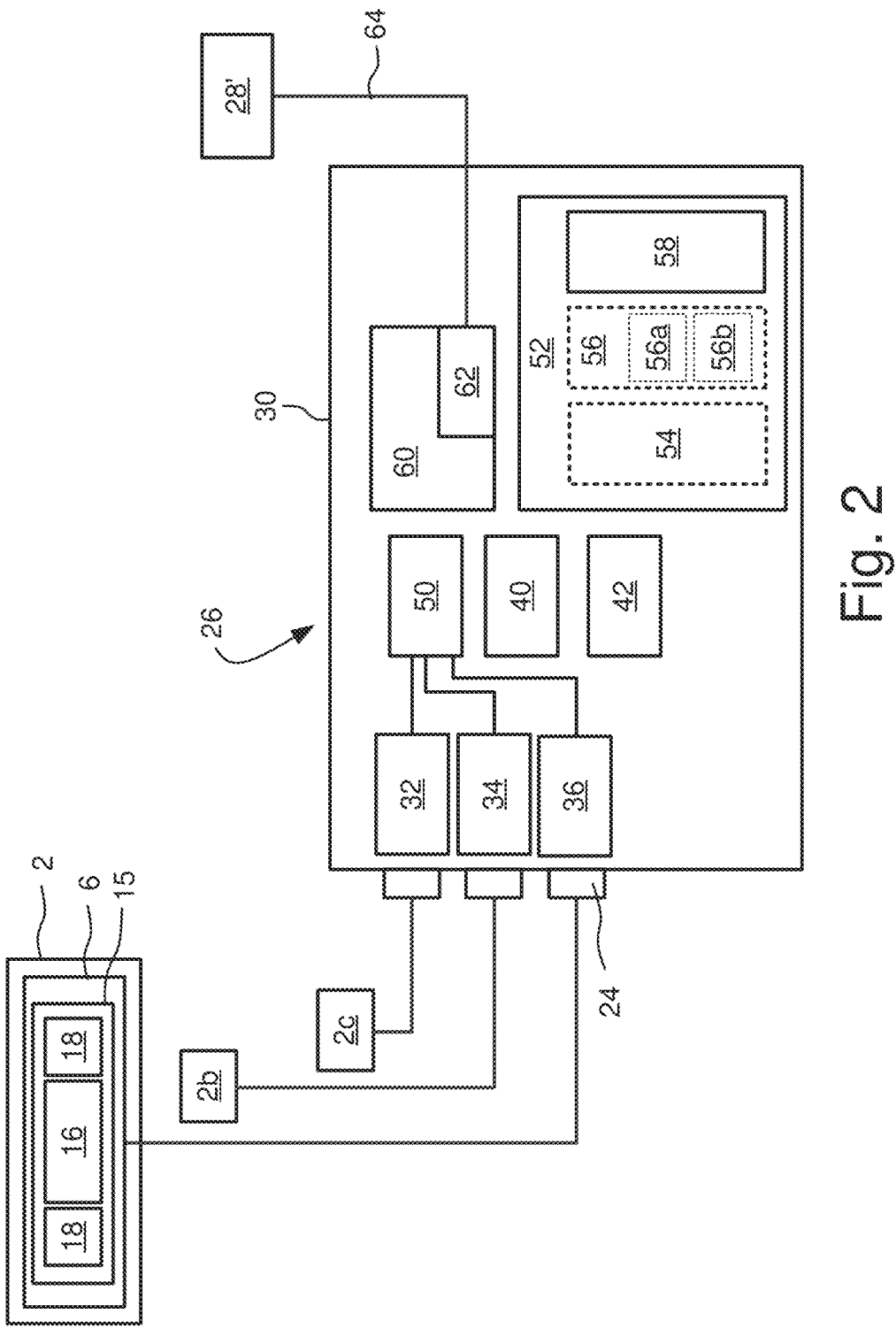
FIG. 2 shows a block diagram of a visualization system including an image processing circuit included in the video processing apparatus of FIG. 1b.

Referring to FIG. 2, the video processing circuit 26 of the VPA 20 is operable to receive image data, present a graphical user interface to allow a user to manipulate image data with a touch screen, and, optionally, output a video signal to allow remote viewing of the images presented with the touch screen. In the present embodiment, the image sensor 16 is communicatively coupled with the video processing circuit 26. Additional endoscopes 2*b* and 2*c* are also communicatively coupled with the video processing circuit 26 via cable sockets 24, each of which is part of a medical device interface 32, 34, 36. A separate, potentially remote, display screen 28' is connected via a cable 64 to a video out connector 62 of a video output board 60.

The VPA 20 may include or omit the display screen 28. The medical device interfaces include the cable sockets and circuits to compatibilize the signals from the image sensors to what the FPGA and processor expect to receive, in terms of image format, for example. Thus, a particular type of endoscope is matched with a corresponding medical device interface and the VPA 20 can thus enable use of different endoscope technologies. The medical device interfaces may also include isolation amplifiers to electrically isolate the video signal, and a power output connector to provide power to the endoscope for the image sensor and the LEDs. The medical device interfaces may also include a serial to parallel converter circuit to deserialize the video signals of endoscopes that generate serial signals, for example serial analog video signals. The medical device interfaces may also include a configuration connector to output image sensor configuration parameters such as image inversion, clock, shutter speed etc.

The VPA 20 includes a circuit board 30 interconnecting the medical device interfaces 32, 34, 36 with a field-programmable gate array (FPGA) 40, a processor 50, and a memory 52 including graphical user interface (GUI) logic 54, object detection logic (OD logic) 56 and a database 58, which are collectively referred to as the video processing circuit 26. Optionally, the video processing circuit 26 includes the video output board 60. The VPA 20 may also include a microphone, a wireless interface operable to receive user inputs via a mouse, keyboard, or other physical user input devices. Example wireless interfaces include Bluetooth and Zigbee controllers. A user interface 46 may also comprise a USB port to receive a USB connector of a wired user input device. Thus, the VPA 20 provides for flexibility in receiving user inputs via various user input devices. The circuit board 30 may comprise one or more rigid circuit board parts provided to mount some or all of the electronic devices, including the processor 50 and the FPGA 42. The memory 52 may also be mounted thereon, for example.

The FPGA 42 is optionally provided because it is capable of rapid power-up (i.e. short boot-up time) and thus is useful in emergency situations. FPGAs process data very fast compared to other memory/instruction combinations and are re-programmable. Therefore, FPGAs facilitate presentation of a live view of the images captured by the endoscope in real-time with minimal latency so that the physician observing the live view can take immediate actions even in emergency situations. The processor 50 combines images from the endoscope with the GUI and provides the combined data to the FPGA to be output. As technology evolves, the functionality of the FPGA 42 may be performed by the processor 50. The VPA 20 is therefore not limited to the precise packaged integrated circuits described with reference to FIG. 2 but can be constructed to take advantage of design and cost targets and future video processing technologies. For example, faster/more costly memory may be used to increase graphics processing speed. Graphics processing may be provided in the FPGA or a processor that incorporates graphics processing logic such as a GPU may be used instead.

The processor 50 may comprise one or more physical processors and/or may be comprised by a plurality of individual processors. The processor 50 may be a central processor (CPU), a graphics processor (GPU), a microcontroller unit (MCU), the FPGA 42, or any combination thereof.

The term "logic" as used herein includes software and/or firmware executing on one or more programmable processing devices, application-specific integrated circuits, field-programmable gate arrays, digital signal processors, hard-wired logic, or combinations thereof. Therefore, in accordance with the embodiments, various logic may be implemented in any appropriate fashion and would remain in accordance with the embodiments herein disclosed. Logic may comprise processing instructions embedded in non-transitory machine-readable media (e.g. memory). The memory 52 may comprise multiple interconnected circuits, including a memory circuit embedded in the processor 50, a memory integrated circuit connected to the processor 50, a hard-drive connected to the processor 50, and any other devices operable to store data and communicate with the processor 50 and/or the FPGA 42.

The GUI logic 54 comprises processing instructions to generate a GUI presented with or by the VPA 20. The GUI can be responsive to user inputs received via the touch screen or other user inputs. The processor 50 receives image data from the medical device interfaces and outputs video signals incorporating the GUI and image data. Image data may be referred to "live images" or "live video" if they are received substantially in real-time from the endoscopes even if they are processed by an object detector after they are saved to memory. The video signals may be received by a memory buffer and the buffer may be read by the display module or video output card to present the GUI and images. Techniques for presenting images are well known, including techniques using buffers or mapped memory. The GUI may comprise first and second panels provided side-by-side in a view. The second panel presents live images and is positioned on the right side of the view, with the first panel positioned on the left side of the view. The GUI may present in the first panel a small version of live images provided by a second endoscope and the user may use the GUI to switch the live images from the first and second endoscopes so that the images from the second endoscope are presented in the second panel while the images from the first endoscope are reduced and presented in the first panel. However, the views from the different endoscopes can be selected by the user with the GUI for presentation in the first or second panel or not displayed at all. The GUI may present various icons corresponding to actions selectable by the user with any of the above-described user input devices, to for example store a copy of a live image, store a portion of video corresponding to live images, invert the views, apply correction curves to the image data to reduce overexposure, etc.

Figure 7:
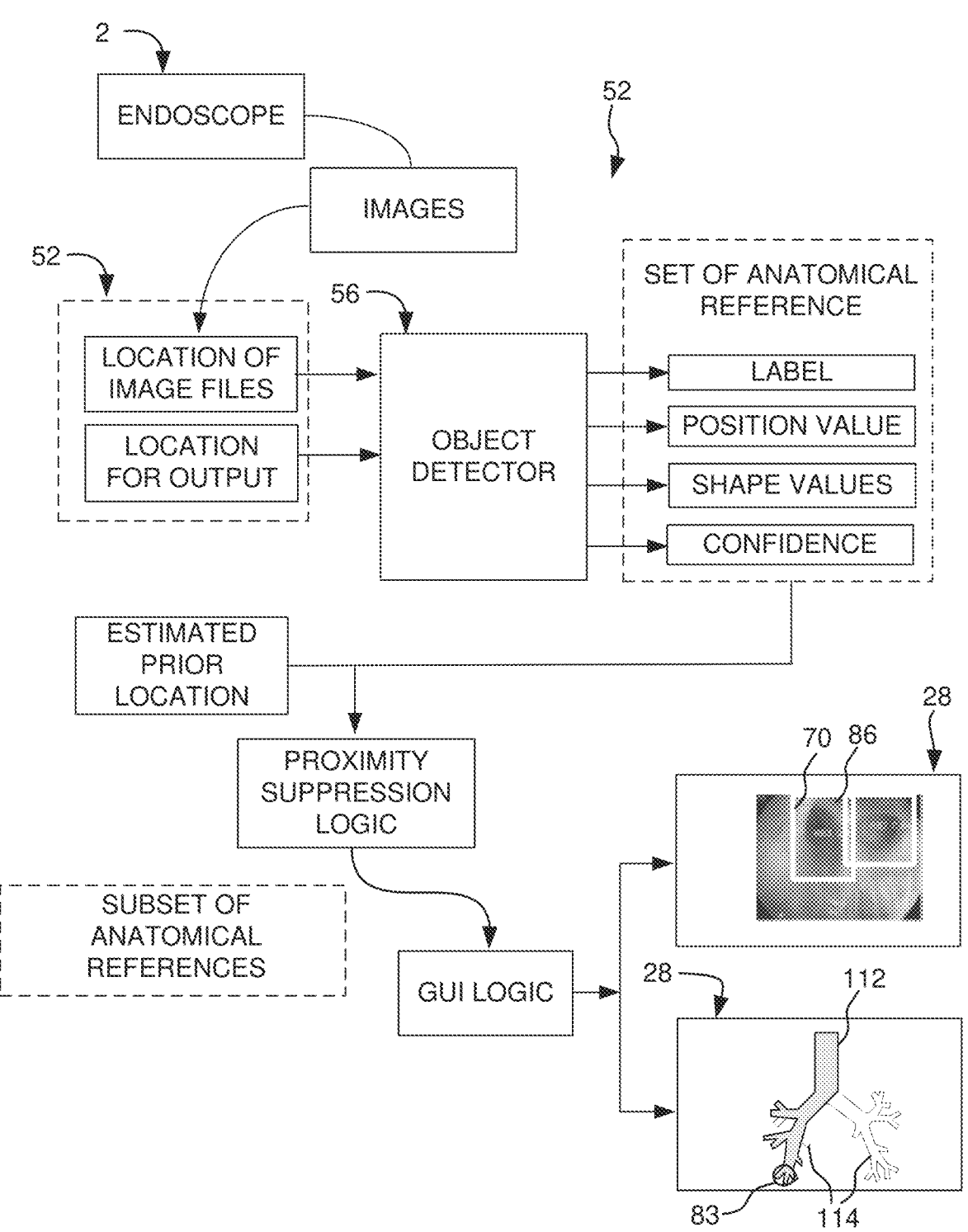
FIG. 7 is a functional diagram showing the inputs and outputs of an object detection logic.

The VPA 20 also comprises the OD logic 56 and the database 58. The OD logic 56 comprises an object detection algorithm, or object detector 56a, that performs image recognition tasks by taking an image (or images) as input and then predicting bounding boxes and class probabilities for each object in the image. Generally, the object detector 56a comprises a first set of known processing instructions and libraries. The object detection logic reads the image files, processes them, and outputs detected object data comprising bounding boxes data, labels, and confidence values representing a probability that a label correctly identifies an object from a training dataset, shown in FIGS. 3a to 4b. The label, therefore, is an anatomic reference identifier. Other anatomic reference identifiers may be used such as numbers, combinations of numbers and letters, and any other markings suitable to uniquely identify the anatomic references. The identifiers correspond to locations in the model, thus correctly identifying an anatomic reference also determines its location in the model. The OD logic 56 can process a single image, a few images (less than 10, preferably 5 or less), or a multitude of images, to make the predictions. For example, the OD logic 56 may use a current image (t), an immediately preceeding image (t−1), and the next preceeding image (t−2) to make predictions. The output may be referred to as a set of anatomical reference positions, each item in the set comprising bounding box data, labels, and confidence values, as shown in FIG. 7.

The OD logic 56 can be any supervised single-pass neural network or networks. By supervised it is meant that the neural network(s) is/are trained with images having a known output. For simplicity the disclosure refers to a single-pass neural network but it is understood that the object detector may comprise multiple networks and that is what is meant even though the singular form is used. The object detector assigns the class probabilities to the bounding boxes, which include detected objects. The probabilities are based on a trained database of images. The object detector uses a convolutional neural network (CNN) to extract features from the image to predict the probability of learned classes. Optionally, a neural processor (NPU) or vision accelerators may be provided to improve robustness and reduce latency. Such NPU devices include, for example, Neural compute stick or NCS (Intel), Jetson AI edge devices (Nvidia), Apple neural engine (Apple), Coral Edge TPU (Google), and Neural processing engine (Qualcomm). Efficient object detection architectures use models based on MobileNEt, ShuffleNet, or GhostNet. Object detectors optimized for GPU computing commonly use ResNet, DarkNet, or DLA architectures.

To use a supervised single-pass object detector, the algorithm and necessary libraries are first downloaded and installed. This installs the neural network architecture. The object detector is then programmed with the location where to read the image files and the location where to store the output. The object detector detects and identifies objects and provides a confidence value indicative of the likelihood that the object was identified correctly. For example, in an image of an office, the object detector may detect a computer with 75% confidence, a desk with 90%, etc. The object detector may accept a confidence threshold value and exclude objects that do not reach the confidence threshold value.

The object detector separates the image into N grids. Each of these grids is of equal size SxS. For each grid, bounding box coordinates, B, for the potential object(s) are predicted with an object label and a probability score for the predicted object's presence. A non-maximal suppression function suppresses all the bounding boxes with comparatively lower probability scores. First, the probability scores associated with each decision are determined and the largest score identified. Then, the bounding boxes with the largest Intersection over Union with the chosen high probability bounding box are removed. This step is then repeated until only the desired final bounding boxes remain.

Before training a neural network model, a labeling tool is used to label the images. The desired classifications should be accurately labeled. A user can review and modify the bounding boxes and assign correct labels. Images are used for a training set, for a test set, and optionally for a validation set. The training set is used for training a neural network model and the other sets are used to assess whether the training is adequate. About 2,000 images per classification are desirable for accuracy of prediction. Once the training of the neural network model is completed, the neural network model can be used to perform object detection.

It has been found that when the endoscope travels into a right or left lumen after reaching a bifurcation, the structures in the right and left sides look very similar. It is therefore difficult based on the images alone to make an accurate prediction. To enhance the prediction, proximity suppression logic 56b is provided which uses an estimated prior location of the endoscope to reduce the number of predictions. The reduced number of predictions have, therefore, higher confidences and may be referred to as a subset of anatomical reference positions. The OD logic 56 may comprise the object detector 56a and the proximity suppression logic 56b.

The proximity suppression logic, or PS logic 56b, comprises a proximity suppression map. The proximity suppression map is provided to increase the confidence values by removing from the object detection analysis potential objects that, based on the location of the endoscope, cannot be the object in the image. Generally, an endoscopic procedure comprises moving the endoscope into and through the patient, typically through various lumens. The path from the entry point to the distal-most point of the navigation route can be divided into segments. If the endoscope is at an anatomic reference position that is near the entry point, the image objects cannot correspond to anatomic reference positions at the distal-most point of the route. Confidence windows are used around the prior position of the endoscope, and anatomic reference positions are given a weights, based on the windows, intended to reduce the confidence value so that they will not be identified by the object detection analysis, thus increasing the confidence values of the anatomic reference positions closer to the prior position.

The map comprises a multitude of anatomic reference position groups, each group including a prior anatomic reference position and weights for the other anatomic reference positions based on their proximity to the prior anatomic reference position. The further away an anatomic reference position is from the prior position, the more likely it is that it will produce an incorrect prediction. Therefore, a far position has a weight that when multiplied by the confidence of the respective prediction reduces its confidence. For example, a 0.1 weight will reduce a 90% confidence to 9%. Each neural network model, e.g. model for bronchioscopy, model for colonoscopy, etc., uses a corresponding proximity suppression map that describes the segments of the procedure's model and defines the proximity derived weights. The weights are determined empirically, preferrably with a trained neural network model, by adjusting weights until the subset of predictions has a desired size. Once defined, the proximity suppression map is stored in the memory. As explained below, once a prior position of the endoscope is determined, the logic uses the prior position to find a relevant group and then applies the weights in the group. As the endoscope moves, different weights are applied to each position upstream and downstream of the current position in the route.

The database 58 may be used to store anatomic reference positions of a route. The database 58 may also be used to track the movement of the endoscope and determine whether all the positions in the route have been examined. Routing is described below. A prior position database may also be stored in memory to store all the positions reached by the endoscope as determined by the object detection logic. The image processing device may be configured to repeatedly store in the prior position database a position indication of the current position of the endoscope as the endoscope is moved during the endoscopic procedure and the current position changes, the position indication comprising at least one of the current position of the endoscope and/or the anatomic reference indicative of the current position of the endoscope.

Referring to FIGS. 3a, 3b, 4a, and 4b, the bounding box data comprises a location and a shape parameter representative of the shape or size of the identified object. The location allows the GUI to overlay the identified object or a facsimile thereof onto an image and can comprise, for example, the location 71 of an upper-right corner of the bounding box, as shown in FIG. 3a. The shape parameter can comprise one or more values. In one example, a shape parameter comprises a value 72 indicative of a width and a value 73 indicative of a height, of the bounding box. A length of a diagonal line connecting opposing corners of the bounding box can also be a shape parameter. FIG. 3*a* shows boxes representing an object label 74 and a confidence value 75. A bounding box 70 is shown in FIG. 3*b* overlayed on an image 76. A bounding box 70' of a second object is also shown. The objects are lumens. An anatomic reference position 86, indicating a bifurcation, is also shown in FIG. 3*b* and schematically in FIG. 5.

Referring to FIGS. 4*a* and 4*b*, in another example the shape parameter value is a radius of a circle and the location corresponds to the center of the circle. A bounding box 70' is shown indicating a center 71 and a radius 72, with label 74 and confidence value 75 also shown. The term "bounding box" is used loosely to indicate a boundary of the object and the boundary shape is not limited to a rectangular shape. As shown, the box can be circular but it could also be square or oval.

Figure 5:
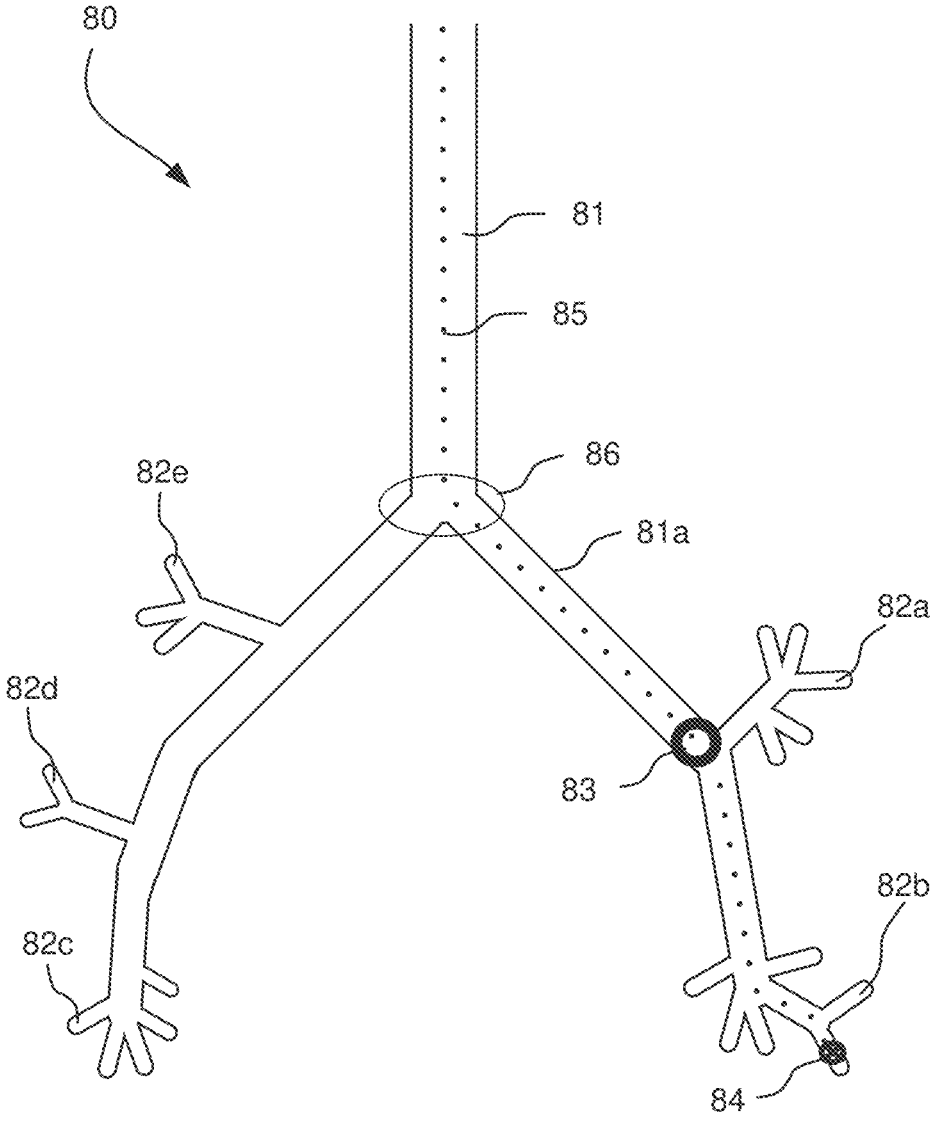
FIG. 5 illustrates schematically a model including a route for the endoscope to perform an endoscopic procedure, the model including a current position and a desired position of the endoscope.

Referring to FIG. 5, a visual model 80 of the human airways is shown. The visual model exemplifies the methods described below and may be referred to as an organ model as it visually displays the organ to be examined. Different neural network models can be used for different endoscopic procedures, such as colonoscopy. The training sets and proximity suppression maps are selected based on the procedure. Thus, the VPA 20 can enable the user to choose a procedure and based on the choice use OD logic corresponding to the choice. Each medical device interface is configured for a particular type of endoscope. Thus, alternatively or additionally, the medical device interface can indicate the procedure and the VPA 20 can automatically choose the visual model and the OD logic when an endoscope is connected to the medical device interface. The visual model 80 is not necessarily in scale and the relative size of individual parts or elements therein does not necessarily correspond to the relative sizes of the parts or elements of the human airways which they model. The visual model 80 includes representations of a trachea 81, a left primary bronchus 81*a*, a right primary bronchus 81*b*, secondary bronchi and some bronchioles 82*a*-82*e*. The visual model 80 may be displayed on a display screen by the VPA 20 and can include overlaid objects such as an estimated position 83 of the endoscope, and a desired position 84 which in this example is the distal-most point of a route 85.

The route 85 may be predetermined based on the selected procedure. In some variations, the route might direct the user to a previously examined position, which would comprise the desired position. This might be the case in the examination of a lesion to determine changes over time. In some variations, the route might direct the user to a previously unexamined position, which would comprise the desired position. This might be the case when the examination requires examination of a number of positions or segments, in which case the desired position might be a position close to the estimated position. As more positions are examined, the desired position changes to ensure all positions that need to be examined are examined. The GUI might show multiple desired positions and change their characteristics as they are examined, for example by changing their color, to indicate a sense of progress to the user. Additional examples pertaining to routing are discussed with reference to FIG. 8.

Figure 6:
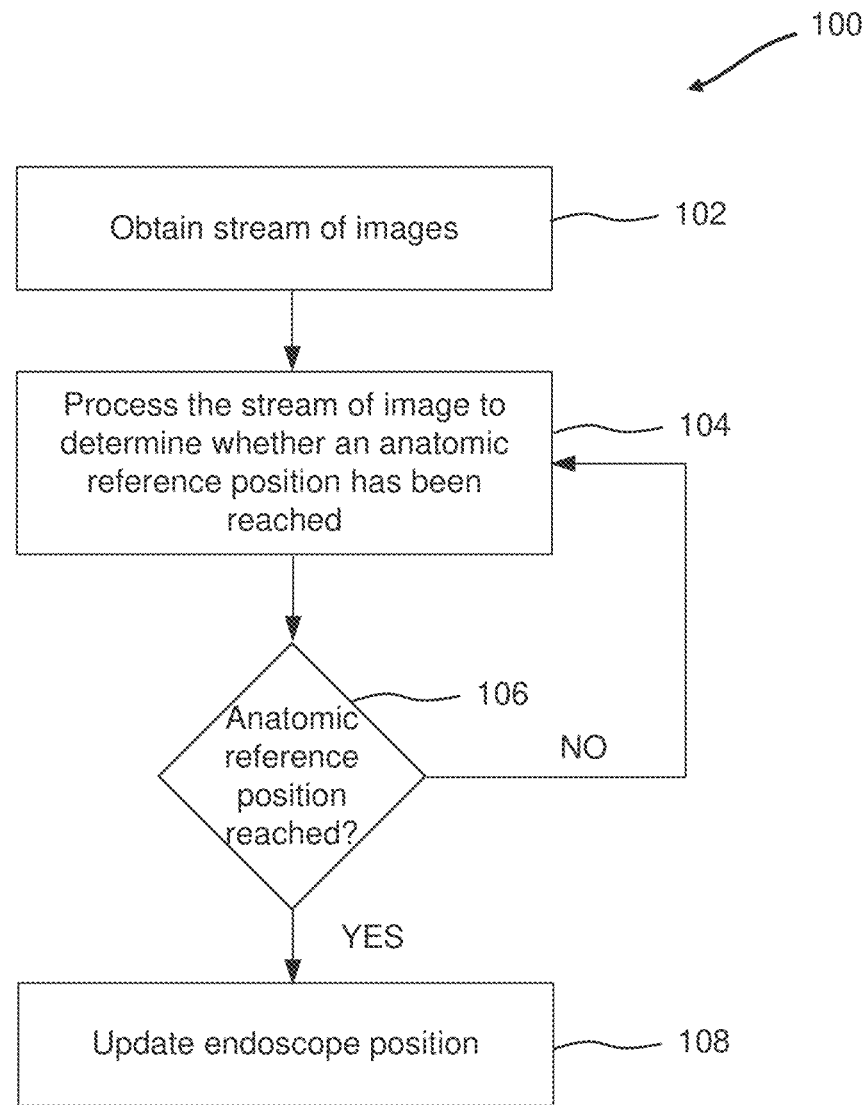
FIG. 6 is a flowchart of an embodiment of a method for recognising anatomic reference positions and updating a position of the endoscope.
Figure 8:
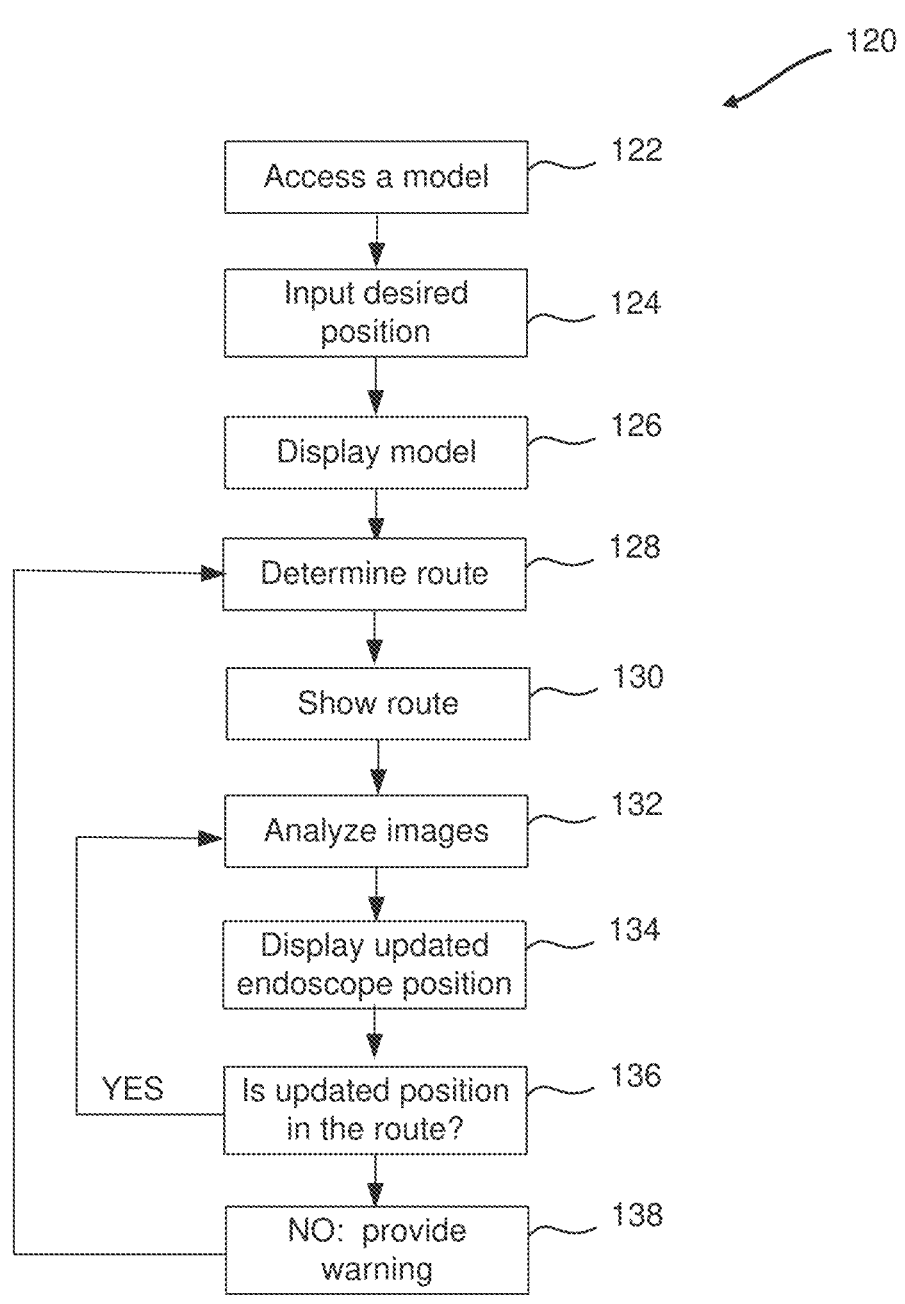
FIG. 8 is a flowchart of an embodiment of a method for determining and displaying a route of the endoscope.

A method for estimating a position of an endoscope in a model is described herein with reference to FIGS. 6 to 8. As exemplified, the model is a model of the human airways, such as the visual model 80 shown in FIG. 5. However, the model is selected based on the endoscopic procedure and can, therefore, be a different model. In one embodiment, the method comprises obtaining a stream of recorded images; continuously analyzing the recorded images of the stream of recorded images using object detection logic to determine if the endoscope reached an anatomic reference position; and if so, update the endoscope position. The reference position may be from a subset of anatomic reference positions selected based on a prior position of the endoscope using the proximity suppression map.

Thereby, the image processing device may determine a position of the endoscope in the model of the human airways in a simple manner by analysing the stream of recorded images. Thereby an easier examination of the human airways may be provided for by allowing the medical personnel to focus on identifying abnormalities in the images from the endoscope rather than keeping track of the position of the endoscope. Additional devices, such as echo (e.g. ultrasound) devices or devices for electromagnetic navigation, may be avoided, allowing for a simpler examination procedure as well as a reduced amount of equipment.

The update endoscope position may be shown in the display screen, allowing the medical personnel to navigate through the human airways in an easy manner. Moreover, the risk of wrongful navigation, such as a navigation of the endoscope to a non-desired part of the airways, may be reduced by having an updated endoscope position, again reducing the risk that a desired part of the human airways is not examined due to wrongful navigation and/or a human procedural error by the medical personnel. Documentation is described below with reference to FIGS. 24 to 29.

When updating the endoscope position, the previous position may be stored, e.g. at a storage medium, a computer, a server, or the like, allowing for an easy documentation that a correct examination of the human airways has been performed. For instance, it may be registered that the endoscope has been positioned in specific bronchioles of the right bronchus, in turn allowing for an easy documentation of the examination.

In some embodiments, an anatomic reference position is, and/or corresponds to, a predetermined position in the model. An anatomic reference position may alternatively or additionally correspond to a plurality of predetermined positions in the model.

A set of anatomic reference positions may comprise two or more anatomic reference positions. In some embodiments, a subset of anatomic reference positions comprises two or more anatomic reference positions from the set of anatomic reference positions, such as some but not all of the anatomic reference positions from the set of anatomic reference positions. The subset of anatomic reference positions may be determined based on the endoscope position, such as a previously estimated endoscope position. In some embodiments, the OD logic may be configured to select from the set of anatomic reference positions, a subset of anatomic reference positions. The subset may comprise at least one, such as a plurality, of the anatomic reference positions from the set of anatomic reference positions.

The predetermined positions and/or an anatomic reference position may be one or more of: the vocal cords, trachea, right main bronchus, left main bronchus, and any one or more furcations occurring in the bronchi, such as bi- or trifurcations into e.g. secondary or tertiary bronchi, bronchioles, alveoli, or the like. The terms "main bronchus" and "primary bronchus" may be used interchangeably. A "position" need not be restricted to a specific point but may refer to an area in the human airways, a portion of a part of the human airways, or a part of the human airways.

In some embodiments, the endoscope position may be estimated as one of the plurality of predetermined positions present in the model which has the smallest distance to the anatomic reference position. Each of the anatomic reference positions may, in some embodiments, correspond to a predetermined position present in the model. In this case, the endoscope position may be determined as the one of the predetermined positions corresponding to the anatomic reference position, which has been reached.

In some embodiments, a user may be able to correct a detection of an anatomic reference position and/or an updated position. The machine learning data architecture may be configured to include the corrected detection of the reaching of the anatomic reference position and/or the corrected updated position into a data set thereof, thereby allowing for the machine learning data architecture to be further trained. Alternatively or additionally, the machine learning data architecture may, where a subsequent detection of the reaching of an anatomic reference position results in the conclusion that a previously determination of the reaching of an anatomic reference position may have been erroneous, correct the position updated based on the erroneous determination and/or include the corrected determination and the image and/or features thereof into a dataset, potentially a training data set, of the machine learning data architecture.

The model of the human airways may be an overall and/or general model of the human airways, such as a schematic overview of the human airways including the lung tree and the trachea. The model may be provided as input specifically prior to each examination or may be an overall model used for most or all examinations. In some embodiments, the model may be a simplified model of the human airways. The model may, alternatively or additionally, be updated during the examination, e.g. in response to updating an endoscope position in the model. Alternatively or additionally, the model may be provided by means of results of a CT scan taken prior to the examination and/or updated subsequently using results of a CT scan taken prior to examination.

In some embodiments, the method further comprises displaying to a user the model. Displaying a model may be or may comprise displaying a view of the model. The method may furthermore comprise indicating on the displayed model, a position of the endoscope and/or indicating on the displayed model an updated position of the endoscope. The indication of the position of the endoscope on the model may be a display of a segment of the human airways, in which the endoscope is estimated to be positioned, such as in a given bronchus and/or a given bronchiole. The indication may be carried out as a graphic indication, such as a coloured mark, a highlighted portion, a flashing portion, an overlay of a portion, or the like. The position may in some embodiments indicate a portion or segment of the airways, in which the endoscope is estimated to be positioned. The model and/or the indication of the endoscope position may be displayed on a display separate from and connected to or integrated with the image processing device. Alternatively, or additionally, indications of one or more previous positions may be displayed, potentially in combination with the indication of the endoscope position.

In some embodiments, the subset may be selected by means of a machine learning data architecture, such as the machine learning data architecture that determines whether an anatomic reference position has been reached, or a second machine learning data architecture.

In some embodiments, the processor is configured to determine a second subset of anatomic reference position, where it is determined that the anatomic reference position, potentially from a first subset of anatomic reference positions, has been reached. Additional subsets are determined as the endoscope reaches additional positions.

In some embodiments, the updated subset of anatomic reference positions comprises at least one anatomic reference positions from the subset of anatomic reference positions. This, in turn, allows the image processing device to determine a backwards movement of the endoscope, such as a movement of the endoscope to a previous position thereof.

The at least one anatomic reference positions from the subset of anatomic reference positions may be or may comprise the reached anatomic reference position. Alternatively or additionally, the at least one anatomic reference positions from the subset of anatomic reference positions may be or may comprise a plurality of previously reached anatomic reference positions.

In some embodiments, the anatomic reference position is a branching structure comprising a plurality of branches. The image processing device may be further configured to: determine which branch from the plurality of branches the endoscope enters; and update the endoscope position based on the determined branch. Thereby, the risk that a wrong endoscope position is estimated where anatomic reference positions look similar may be reduced. This moreover allows for an improved registration of, in which part of the airways the endoscope has been, e.g. so as to make sure that a sufficiently detailed examination has been performed. For example, where branchings in the left and right main bronchus, respectively, may look similar, the image processing device may estimate the endoscope position being aware of, whether the endoscope has entered the left or right main bronchus. Hence, the image processing device may be able to distinguish between, for instance, furcations into secondary bronchi in the right and left primary bronchi, respectively.

The branching may be a furcation, such as a bifurcation, a trifurcation, or the like. The image processing device may determine which branch from the plurality of branches, the endoscope enters by analysing the image stream. The determined branch may be the branch, which the endoscope enters. Alternatively, or additionally, the image processing device may determine which branch the endoscope enters based on input from one or more sensors, such as a compass or an accelerometer, potentially arranged at the handle of the endoscope, magnetic resonance devices, or the like. In some embodiments, the image processing device may use a machine learning data architecture to identify the branching and/or to determine which branch from the plurality of branches, the endoscope enters.

Where the stream of images is provided to the operator and/or medical personnel, e.g. via a display unit, the image processing device may further be able to indicate to the operator and/or medical personnel the branching. In some embodiments, each of the branches may be indicated. The branching and/or branches may be graphically indicated, e.g. by means of a graphic overlay, such as a text and/or colour overlay, on an image of the stream.

In some embodiments, the indications of the branching and/or branches may be indicated upon request from a user, e.g. medical personnel. In other words, the user may activate an indication of the branching and/or branches. The request may, for instance, be input to the image processing device by means of a button push, a touch screen push, and/or a voice command. Hence, the branching and/or specific branches may be indicated on an endoscope image to assist the user in navigating the endoscope, when the user wishes so. Hence, where the user does not need navigating assistance, the indications need not be provided.

In some embodiments, the image processing device may be configured to determine and/or locate, in the image, a centre point, such as a geometrical centre, of each of the two or more lumens. Alternatively or additionally, the image processing device may be configured to determine an extent of each of the lumens in the at least one recorded images.

The image processing device may be configured to estimate the position using the (first) machine learning architecture.

In some embodiments, the image processing device is configured to, where it is determined that two or more lumens are present in the at least one recorded image, estimate a position of the two or more lumens in the model of the human airways using the first machine learning architecture. In some embodiments, the image processing device, such as the processor thereof, is configured to determine if two or more lumens are present in the at least one recorded image using a second machine learning architecture trained to detect lumens in an endoscope image. The second machine learning architecture trained to detect lumens may be a second machine learning architecture trained to detect a lumen, such as one or more lumens, in an endoscope image, such as in an image from an image sensor of an endoscope.

In some embodiments, the image processing device, such as the processor thereof, is configured to, in response to a determination of the position of the two or more lumens in the model of the human airways, determine whether one or more lumens are present in at least one subsequent recorded image and, where it is determined that one or more lumens are present in the at least one subsequent recorded image, determine a position of the one or more lumens in the model of the human airways based at least in part on a previously estimated position of the two or more lumens and/or a previous estimated endoscope position. Thereby, the image processing device may determine if an endoscope is moving closer towards, enters, or is about to enter one of the earlier identified lumens.

The subsequent recorded image may be an image from the stream of recorded image, which is recorded subsequent, potentially temporally subsequent, to the at least one image, in which two or more lumens are detected. In some embodiments, the at least one image, in which the two or more lumens are detected to be present may be a first image and the at least one subsequent recorded image may be a second image, the second image being recorded subsequent to the first image.

In some embodiments, the processor is further configured to where it is determined that the anatomic reference position has been reached, storing a part of the stream of recorded images. This, in turn, allows for an improved documentation of the examination as it may subsequently be verified that the desired part of, such as all of, the human airways has been examined. Alternatively or additionally the video stream may subsequently be (re-)checked for abnormalities at respective positions in the airways.

In some embodiments, a user, such as medical personnel, may subsequently correct an endoscope position determined by the image processing device based on the stored recorded image stream. A corrected endoscope position may be transmitted to the image processing device, potentially introducing one or more images from the stored recorded image stream and/or the anatomic reference position in a training dataset so as to allow the machine learning data architecture to be trained.

The view of the model of the human airways may be a two-dimensional view, such as a two-dimensional schematic view schematically showing the human airways. A two-dimensional schematic view may for example show a cross-section of the human airways, e.g. in the shape of a lung tree. Alternatively or additionally, the view of the model may be provided so as to show or indicate a third dimension, e.g. by providing a plurality of two-dimensional views, such as two cross-sections, and/or by allowing a rotation of two-dimensional view 180 degrees, up to 360 degrees, or 360 degrees around a rotational axis. Where a third dimension is to be indicated, a rotation, potentially up 360 degrees or 360 degrees, about each of three axes, i.e. the x-, y-, and z-axes, may be provided.

FIG. 6 shows a flowchart 100 of a method for determining the position of the endoscope. The method can be best understood by viewing FIG. 7, which graphically depicts the flow of data according to the method.

The method begins at 102, by obtaining a stream of images from the endoscope. The images are stored in a location of image files which is accessible and known by the OD logic.

At 104, an image from the stream of images is analysed to assign the labels and confidence values. A plurality of images from the stream of images may be analysed sequentially or simultaneously.

At 106, the method determines if an anatomic reference position has been reached by evaluating the confidence values of detected anatomic references and determining if a confidence value exceeds a threshold or by selecting the anatomic reference with the highest confidence value. If so, the method proceeds to 108. Otherwise, the method returns to 104.

At 108, the method updates the endoscope position by storing an indication thereof, such as a segment identification, a unique anatomic reference, or the like, in an estimated location register of the memory accessible by the OD logic. In subsequent loops the OD logic will utilize the endoscope position to select another subset of anatomic references. The endoscope position is also updated in the model. This may comprise generating an endoscope position and/or removing a previous endoscope position and inserting a new endoscope position.

Thus, the endoscope position is determined as one in a plurality of anatomic positions in the subset based on the determination that an anatomic reference has been reached and a previous position, e.g. previously determined anatomic reference.

In some embodiments, the image processing device further comprises input means for receiving a predetermined desired position in the lung tree, the processor being further configured to indicate on the model of the human airways the predetermined desired position. The predetermined desired position may be a specific part or a specific area in a lung tree, such as one or more specific bronchi, one or more specific bronchioles, and/or one or more specific alveoli. The predetermined desired position may be a part, in which an examination, e.g. for abnormalities, is to take place.

The predetermined desired position may be input to the image processing device via the user input interfaces and devices described with reference to FIG. 2. The indication on the model may be performed in a manner similar to the indications described with respect to the previous endoscope position and/or the determined endoscope position.

In some embodiments, the processor is further configured to determine a route to the predetermined desired position, the route comprising one or more predetermined desired endoscope positions, determine whether the updated endoscope position corresponds to at least one of the one or more predetermined desired endoscope positions, and where it is determined that the updated endoscope position does not correspond to at least one of the one or more predetermined desired endoscope positions, provide an indication on the model that the updated endoscope position does not correspond to at least one of the one or more predetermined desired endoscope positions. Thereby, the medical personnel may be provided with a suggested route to the desired position, allowing for an easy navigation of the endoscope as well as a potentially time-reduced examination as wrong navigations with the endoscope can be avoided or indicated as soon as the wrong navigation has occurred.

In some embodiments, the route may be determined from the entry of the human airways and/or from the updated anatomic reference reached by the endoscope. In some embodiments, the route may be a direct route to a desired position. Additionally, or alternatively, the route may be determined as a route via one or more anatomic references in the route. The route may be updated after each update of the endoscope position. Where the route is updated after each update of the endoscope position, a turn-by-turn navigation-like functionality may be provided, e.g. such that the medical personnel may be provided with information of how to navigate the endoscope when a bifurcation occurs in the human airways. The route may be updated in response to the determination that the endoscope position is not on the route, e.g. does not correspond to or is not equal to one of the desired positions.

FIG. 7 is a functional diagram showing the inputs and outputs of the object detector 56a. The various logic are shown in block diagram to simplify description of their functions. It is understood that logic comprising processing instructions can be structured in a variety of ways. The object detector 56a inputs are the image files and the outputs comprise the detected set of anatomical references. For each anatomical reference in the set there are parameters, described above, which provide indications of position, label (name), shape and confidence.

Proximity suppression logic 56b reads the estimated prior location of the endoscope and based thereon uses the proximity suppression map to determine a subset of anatomic references. The subset includes an anatomic reference corresponding to the present location of the endoscope. The GUI logic uses the present location to update the visual model, where the present location is indicated by a circle denoted by numeral 83. In other words, the OD logic detects the anatomic reference in the images and the anatomic reference corresponds to a position in the model. The model can also show the route taken by the endoscope, indicated by a colored model area 112, and also portions of the model showing where the endoscope has not been, indicated by a white model area 114.

FIG. 8 shows a flowchart 120 of another embodiment of the method, including routing. The method aids in the navigation from an initial to a desired position, as described with reference to FIG. 5, showing a model 80, a desired position 84 and a route 85. An anatomic reference position 86 corresponding to a bifurcation is also shown in the model 80.

The method begins at 122, when a model of the human airways is accessed. The model can be a generic, well-known model. For bronchoscopy, the model can include an overall structure of the human airways, as described with reference with FIG. 5. The model is stored in the memory.

At 124, a predetermined desired position on the model is input. The predetermined desired position may be input with the GUI in response to a GUI query and presentation by the GUI of a menu of desired positions, from which the user can select the desired position.

At 126, the model is displayed in the display screen. An initial position of the endoscope and the desired position may be indicated. The initial position may be in an upper portion of trachea as shown in the view of the model. The model may be displayed before the predetermined desired position on the model is input and can be used to give the user the option to select a desired position by activating an icon from icons representing the potential desired positions.

At 128, a route from a starting point to the desired position is determined throughout the model. The route may comprise a number of anatomic reference positions. A plurality of desired positions may be provided, which the route will connect. The GUI can use the starting and desired positions, and information from the model representing the lumens, such as point-to-point information contained in lumen vectors of lumen segments, to generate a route in the luments that connects the desired positions. The model can also include X, Y coordinates for the anatomic reference positions and define a route by connecting the anatomic reference positions using the X, Y coordinates and the coordinates of the segments connecting anatomic references, such that navigation only occurs within the lumens of the segments.

At 130, the route is shown. The route 85 may be shown by a marking, e.g. as illustrated in the model view of FIG. 5.

At 132, a stream of images is obtained and analyzed in accordance with the method described with reference to FIG. 6.

At 134, the updated endoscope position, obtained at 108 of the flowchart 100, is updated in the model. The updated endoscope position is shown by a marker arranged at a position in the model corresponding to the updated endoscope position. The updated endoscope position replaces the previous endoscope position in the model. Alternatively, one or more previous positions may remain shown on the view of the model, potentially indicated such that the updated position is visually distinguishable from the previous position(s). For instance, markers indicating a previous endoscope position may be altered to be of a different type or colour than the marker indicating an updated endoscope position.

At 136, the method determines whether the updated endoscope position is on the route. The determination is made by determining whether the updated endoscope position corresponds to one of the anatomic references in the route. If the detected anatomic reference matches an anatomic reference in the route, the endoscope is in the route. If the updated position is on the route, the method returns to 132, and analyzes images to navigate to the next anatomic reference in the route.

At 138, if the updated position is not on the route, a warning is provided. The warning can be an indication that the updated position is not on the route. The indication may be a visual indication and/or may be an auditory cue, such as a sound played back to the user, or the like. Subsequent to providing the warning, the method returns to 128, where a new route from the updated endoscope position to the desired position is generated.

The following items are further variations and examples of the embodiments described with reference to FIGS. 1a, 1b, 2 to 5, and 6 to 8.

1. An image processing device for estimating a position of an endoscope, said image processing device comprising: a processor operationally connectable to an image sensor of the endoscope; a first machine learning data architecture trained to determine a set of anatomic reference positions; and a model of human airways, wherein the processor is configured to: obtain from the image sensor of the endoscope a stream of recorded images during an endoscopic procedure; continuously analyse the recorded images of the stream of recorded images using the first machine learning data architecture to determine if the endoscope reached an anatomic reference position of a subset of anatomic reference positions from the set of anatomic reference positions, the subset comprising a plurality of anatomic reference positions; and where it is determined that the anatomic reference position has been reached, update the endoscope position based on the anatomic reference position and update the subset of anatomic reference positions.

2. The image processing device of item 1, wherein the updated subset of anatomic reference positions comprises at least one anatomic reference positions from the subset of anatomic reference positions.

3. The image processing device of item 1, wherein the anatomic reference position two or more lumens of a branching structure.

4. The image processing device of item 1, further comprising a second machine learning architecture trained to detect lumens in an endoscope image, wherein the image processing device is configured to determine if two or more lumens are present in the at least one recorded image using the second machine learning architecture.

5. The image processing device of item 3, wherein the image processing device is further configured to, where it is determined that the anatomic reference position has been reached, estimate a position of the two or more lumens in the model of the human airways.

6. The image processing device according to item 3, wherein the image processing device is configured to, where it is determined that the anatomic reference position has been reached, estimate a position of the two or more lumens in the model of the human airways using the first machine learning architecture.

7. The image processing device of item 5, wherein the image processing device is configured to determine whether one or more lumens are present in at least one subsequent recorded image and, where it is determined that one or more lumens are present in the at least one subsequent recorded image, determine the position of the one or more lumens in the model of the human airways based at least in part on a previously estimated position of the two or more lumens and/or a previous estimated endoscope position.

8. The image processing device of item 5, wherein the image processing device is further configured to, in response to determining that the anatomic reference position has been reached: determine which one of the two or more lumens the endoscope enters; and update the endoscope position based on the determined one of the two or more lumens.

9. The image processing device of item 8, wherein the image processing device is configured to determine which one of the two or more lumens the endoscope enters by analysing, in response to a determination that two or more lumens are present in the at least one recorded image, a plurality of the recorded images to determine a movement of the endoscope.

10. The image processing device of item 8, wherein the anatomic reference position is a branching structure comprising a plurality of branches, and wherein the image processing device is further configured to: determine which branch from the plurality of branches the endoscope enters; and update the endoscope position based on the determined branch.

11. The image processing device of item 8, wherein the processor is further configured to: where it is determined that the anatomic reference position has been reached, store a part of the stream of recorded images.

12. The image processing device of item 1, wherein the processor is further configured to: subsequent to updating the subset of anatomic reference positions, update the model of the human airways based on the reached anatomic reference position.

13. The image processing device of item 12, wherein the model of the human airways is a visual model based on images from a magnetic resonance (MR) scan output and/or a computed tomography (CT) scan output.

14. The image processing device of item 1, wherein the processor is further configured to: subsequent to the step of updating the endoscope position, perform a mapping of the endoscope position to the model of the human airways and display the endoscope position on a view of the model of the human airways.

15. The image processing device of item 1, wherein the processor is further configured to: store at least one previous endoscope position and display on the model of the human airways the at least one previous endoscope position.

16. The image processing device of item 1, further comprising input means for receiving a predetermined desired position in the lung tree, the processor being further configured to: indicate on the model of the human airways the predetermined desired position.

17. The image processing device of item 16, wherein the processor is further configured to: determine a route to the predetermined desired position, the route comprising one or more predetermined desired endoscope positions, determine whether the updated endoscope position corresponds to at least one of the one or more predetermined desired endoscope positions, and where it is determined that the updated endoscope position does not correspond to at least one of the one or more predetermined desired endoscope positions, provide an indication on the model that the updated endoscope position does not correspond to at least one of the one or more predetermined desired endoscope positions.

18. The image processing device of item 1, wherein the first machine learning data architecture is trained by: determining a plurality of anatomic reference positions of the body cavity, obtaining a training dataset for each of the plurality of anatomic reference positions based on a plurality of endoscope images, and training the first machine learning model using said training dataset.

19. An endoscope system comprising an endoscope and an image processing device according to item 1.

20. An endoscope system according to item 19, further comprising a display unit, wherein the display unit is operationally connectable to the image processing device, and wherein the display unit is configured to display at least a view of the model of the human airways.

The following items are additional variations and examples of the embodiments described with reference to FIGS. 1a, 1b, 2 to 5, and 6 to 8.

1. An image processing device for estimating a position of an endoscope in a model of the human airways using a first machine learning data architecture trained to determine a set of anatomic reference positions, said image processing device comprising a processor operationally connectable to an image sensor of the endoscope, wherein the processor is configured to: obtain a stream of recorded images; continuously analyse the recorded images of the stream of recorded images using the first machine learning data architecture to determine if an anatomic reference position of a subset of anatomic reference positions, from the set of anatomic reference positions, has been reached; and where it is determined that the anatomic reference position has been reached, update the endoscope position based on the anatomic reference position.

2. The image processing device of item 1, wherein the subset comprises a plurality of anatomic reference positions.

3. The image processing device of item 1 or 2, wherein the processor is further configured to: where it is determined that the anatomic reference position has been reached, update the subset of anatomic reference positions.

4. The image processing device of item 3, wherein the updated subset of anatomic reference positions comprises at least one anatomic reference positions from the subset of anatomic reference positions.

5. The image processing device according to any one of the preceding items wherein the image processing device is configured to continuously analyse the recorded images to determine if two or more lumens, potentially of a branching structure, are present in at least one of the recorded images.

6. The image processing device according to item 5 wherein the image processing device is configured to determine if two or more lumens are present in the at least one recorded image using a second machine learning architecture trained to detect lumens in an endoscope image.

7. The image processing device according to item 5 or 6, wherein the image processing device is further configured to, where it is determined that two or more lumens are present in the at least one recorded image, estimate a position of the two or more lumens in the model of the human airways.

8. The image processing device according to item 7, wherein the image processing device is configured to, where it is determined that two or more lumens are present in the at least one recorded image, estimate a position of the two or more lumens in the model of the human airways using the first machine learning architecture.

9. The image processing device according to any one of items 7 or 8, wherein the image processing device is configured to, in response to a determination of the position of the two or more lumens in the model of the human airways, determine whether one or more lumens are present in at least one subsequent recorded image and, where it is determined that one or more lumens are present in the at least one subsequent recorded image, determine a position of the one or more lumens in the model of the human airways based at least in part on a previously estimated position of the two or more lumens and/or a previous estimated endoscope position.

10. The image processing device according to any one of items 5-9, wherein the image processing device is further configured to, in response to determining that two or more lumens are present in the at least one recorded image: determine which one of the two or more lumens the endoscope enters; and update the endoscope position based on the determined one of the two or more lumens.

11. The image processing device according to item 10 wherein the image processing device is configured to determine which one of the two or more lumens the endoscope enters by analysing, in response to a determination that two or more lumens are present in the at least one recorded image, a plurality of recorded images to determine a movement of the endoscope.

12. The image processing device according to any one of the preceding items, wherein the anatomic reference position is a branching structure comprising a plurality of branches, and wherein the image processing device is further configured to: determine which branch from the plurality of branches the endoscope enters; and update the endoscope position based on the determined branch.

13. The image processing device according to any one of the preceding items, wherein the processor is further configured to: where it is determined that the anatomic reference position has been reached, storing a part of the stream of recorded images.

14. The image processing device according to any one of the preceding items, wherein the processor is further configured to: prior to the step of updating the subset of anatomic reference positions, generate the model of the human airways, and/or subsequent to the step of updating the subset of anatomic reference positions, update the model of the human airways based on the reached anatomic reference position and/or an anatomic reference position of the updated subset of anatomic reference positions.

15. The image processing device according to item 14, wherein the model of the human airways is a visual model of the human airways, preferably generated based on images from a magnetic resonance (MR) scan output and/or a computed tomography (CT) scan output.

16. The image processing device according to any one of the preceding items, wherein the processor is further configured to: subsequent to the step of updating the endoscope position, perform a mapping of the endoscope position to the model of the human airways and display the endoscope position on a view of the model of the human airways.

17. The image processing device according to any one of the preceding items, wherein the processor is further configured to: store at least one previous endoscope position and display on the model of the human airways the at least one previous endoscope position.

18. The image processing device according to any one of the preceding items further comprising input means for receiving a predetermined desired position in the lung tree, the processor being further configured to: indicate on the model of the human airways the predetermined desired position.

19. The image processing device according to item 18, wherein the processor is further configured to: determine a route to the predetermined desired position, the route comprising one or more predetermined desired endoscope positions, determine whether the updated endoscope position corresponds to at least one of the one or more predetermined desired endoscope positions, and where it is determined that the updated endoscope position does not correspond to at least one of the one or more predetermined desired endoscope positions, provide an indication on the model that the updated endoscope position does not correspond to at least one of the one or more predetermined desired endoscope positions.

20. The image processing device according to any one of the preceding items, wherein the first machine learning data architecture is trained by: determining a plurality of anatomic reference positions of the body cavity, obtaining a training dataset for each of the plurality of anatomic reference positions based on a plurality of endoscope images, training the first machine learning model using said training dataset.

21. An endoscope system comprising an endoscope and an image processing device according to any one of the preceding items, wherein the endoscope system has an image sensor, and wherein the processor of the image processing device is operationally connectable to said image capturing unit of the endoscope.

22. An endoscope system according to item 21 further comprising a display unit, wherein the display unit is operationally connectable to the image processing device, and wherein the display unit is configured to display at least a view of the model of the human airways.

23. A display unit comprising an image processing device according to any one of items 1-22.

24. A computer program product comprising program code means configured to cause at least a processor of an image processing device to perform the steps of any one of items 1-22, when the program code means are executed on the image processing device.

As described above with reference to FIGS. 1a, 1b, 2 to 5 and below with reference to FIGS. 9 to 11, the visualization system can recognize previously observed locations during an endoscopic procedure. A specific embodiment is described below with reference to FIG. 9. In some embodiment and variations thereof, the method comprises: obtaining a stream of images from an image sensor of an endoscope during the endoscopic procedure; during the endoscopic procedure, building a database of previously observed locations based on images of the stream of images; and continuously comparing images of the stream of images with the database of previously observed locations to determine if an image of the stream of images is recorded from a previously observed location.

It has been realised that it is beneficial during an endoscopy to recognise whether an image is recorded at or near a previously observed location. Thereby, an improved navigation of the endoscope during the endoscopic procedure may be allowed for as the operator upon arrival at a location may be provided with information as to whether the location has been reached before during the procedure based on the images. This, again, may allow the operator to base the navigation of the endoscope accordingly, such as in which direction the endoscope is to be moved from the previously visited position to perform the desired examination.

Furthermore, where the method is used with a method and/or system for determining a position of an endoscope based on images of the endoscope, the method may allow for an improved determination of the position as the system may with a higher probability correctly identify a previously observed location, thereby reducing the risk of an erroneous location determination of the endoscope.

A previously observed location may be a location, at which the endoscope has been at an earlier point in time during the examination and/or a location, which has been observed by the endoscope at an earlier point in time during the examination.

In some variations of the present embodiment, obtaining images, building the database, and comparing the images may be performed simultaneously. In other variations, the obtaining may be performed prior to the building and/or comparing. Alternatively or additionally, the building of the database may be performed before the comparing and/or the building may be performed continuously. Alternatively or additionally, the stream of images may be obtained continuously.

Building a database may comprise generating one or more database entries. Each database entry may comprise and/or correspond to an endoscope location, such as a previous endoscope location. Alternatively or additionally, each database entry may comprise and/or correspond to an image. In some embodiments, each database entry comprises information about an endoscope location, and information about one or more images, such as one or more images and/or a representation thereof. The information may be a position indication of the current position of the endoscope, the position indication comprising at least one of the current position of the endoscope and/or the anatomic reference indicative of the current position of the endoscope.

The endoscope location may be a location of the tip part of the endoscope. Alternatively or additionally, the endoscope location may be a location of the endoscope in a human cavity and/or in a model of the human cavity. The endoscope location may be or indicate a segment of the human cavity.

Alternatively or additionally, the method may further comprise outputting an output signal based on the determination of if an image of the stream of images is recorded from a previously observed location. In some embodiments, the output signal may indicate and/or comprise information regarding whether the image is determined to be recorded from a previously observed location. Alternatively or additionally, the output signal may indicate and/or comprise information about a previously observed location, such as a previously observed location, from which it is determined that the image is recorded. The output signal may be provided to a display screen, which may potentially indicate whether the image is recorded at a previously visited location. Alternatively or additionally, the output signal may comprise the stream of images.

The comparing may comprise providing the images to a machine learning data architecture trained to determine if an image is recorded from a previously observed location.

The machine learning data architecture may be a supervised machine learning architecture. The machine learning data architecture may be trained by obtaining a training data set comprising, for various locations, a plurality of endoscope images obtained at the respective location, and for each endoscope image having a human operator determine the location at which it has been obtained. Alternatively or additionally, the machine learning data architecture may be trained by obtaining a training data set comprising, for each location an image, potentially corresponding to an image of a database, and a plurality of endoscope images obtained at the respective location, and for each of the plurality of endoscope images having a human operator determine whether it is obtained at or near the location, at which the image of the location is obtained.

The machine learning data architecture may be a first machine learning data architecture.

In some embodiments, the comparing comprises reducing a dimensionality of the images of the stream of images and comparing the images of reduced dimensionality with the database. By reducing the dimensionality and comparing these with the database, only the necessary features to perform the comparison may be represented in the reduced dimensionality image allowing for an improved comparison, e.g. where an image show the view of the human cavity at a previously visited location but with a slightly different section, cut, or angle.

Building the database may comprise reducing the dimensionality of an image and storing the image of reduced dimensionality in the database and/or database entries, such as each database entry.

The images may be dimensionality reduced by means of an autoencoder trained to encode the image to generate the image of reduced dimensionality. The autoencoder may be a self-supervised method that produces the same image as an input image. It may use an encoder configured to reduce the amount of information to a minimum and a decoder configured to recover the full size of the image using only the reduced information. In some embodiments, a representation of the image may contain compressed information of the original (input) image and a vector, called the Latent Space or Latent Space Representation, may be produced by the autoencoder. This vector may be used to compare different images and assign the probability of the different images being obtained at the same location.

Alternatively or additionally, the images may be dimensionality reduced using the (first) machine learning data architecture.

In some embodiments, the (first) machine learning data architecture is a Convolutional Neural Network (CNN). The CNN may be used to reduce the dimensionality of the input images. This neural network may be trained as a classification, segmentation, or object detection problem, potentially depending on the annotated data available. Features extracted by this network may also be a dimensional reduction of the original images. The features extracted from images may be features vectors. A feature vector may represent an image of reduced dimensionality. Differences of the feature vectors computed for different images may be used to assign the probability that images belong to the same location.

The images of reduced dimensionality may be a vector. The reduced dimensionality image need not represent the image, or at least not fully represent the image, but may comprise and/or represent elements and/or features from the image.

The reduced dimensionality images may be compared with the database, potentially vector to vector, so that a match and/or a distance between the reduced dimensionality images and a reduced dimensionality image of the database is/are determined. Where a match is determined and/or a distance between the reduced dimensionality images of the image stream and the database, respectively, is below a predetermined distance threshold, it may be determined that the image is obtained at a previously visited location.

The predetermined distance threshold may in some embodiments be determined based on a mean, mode, root mean square (RMS) of the distances between vectors. Alternatively or additionally, clustering algorithms, such as k-means clustering, may be used to determine whether a match can be determined between the reduced dimensionality images of the image stream and the database, respectively.

In some variations of the present embodiment, building the database comprises determining whether a predetermined position has been reached, wherein each previously observed location corresponds to a predetermined position and, where it is determined that the predetermined position has been reached, creating an entry in the database based on one or more images of the image stream. Thereby, a position of the endoscope may be determined when the endoscope arrives at a previously visited location.

The predetermined position may a predetermined anatomic reference position. Alternatively or additionally, the predetermined position may be a predetermined position of a set of predetermined positions. Alternatively or additionally, the predetermined position may correspond to or may be a predetermined position in a model, such as a computer model of a human cavity, in which the endoscopic procedure is performed.

Where the endoscopic procedure is a bronchoscopic procedure, the predetermined position may be a furcation and/or a branching of a human airways, such as a branching between main bronchi, secondary bronchi, tertiary bronchi, alveoli, or the like.

In some variations of the present embodiment, the determination whether a predetermined position has been reached comprises continuously analysing the recorded images of the stream of recorded images using a machine learning data architecture, the machine learning data architecture being trained to determine a set of anatomic reference positions, to determine if an anatomic reference position of a subset of anatomic reference positions, from the set of anatomic reference positions, has been reached. Thereby the accuracy of the determination whether the predetermined position has been reached may be improved.

The machine learning data architecture may be trained by being provided with a training data set comprising a number, such as a large number, such as 100 or more, image streams, each potentially comprising a plurality of images, from an endoscope and having a human operator determine the predetermined anatomic reference position at which the images have been obtained. The training data set may comprise one or more images showing anatomic reference positions inside a human cavity, such as inside the human airways where the endoscopic procedure is a bronchoscopic procedure. The images may be from a video stream of an image device of an endoscope. The machine learning data architecture may be trained to optimise towards a F score, such as a F1 score or a Fβ, which it will be appreciated is well known in the art. The machine learning data architecture may be trained using the training data set and corresponding associated anatomic reference positions. Potentially, the anatomic reference positions may be associated by a plurality of people.

The machine learning data architecture trained to determine a set of anatomic reference positions, to determine if an anatomic reference position of a subset of anatomic reference positions, from the set of anatomic reference positions, has been reached. This machine learning data architecture may be a second machine learning data architecture. Alternatively, the machine learning data architecture may be the (first) machine learning data architecture trained to determine if an image is recorded from a previously observed location and further trained to determine a set of anatomic reference positions, to determine if an anatomic reference position of a subset of anatomic reference positions, from the set of anatomic reference positions, has been reached.

In some variations of the present embodiment, the determination whether a predetermined position has been reached further comprises to continuously analyse the recorded images to determine if two or more lumens, potentially of a branching structure, are present in at least one of the recorded images. The determination whether two or more lumens are present may be carried out by the machine learning data architecture. Alternatively, the determination if two or more lumens are present in the at least one recorded image may be performed using a third machine learning architecture trained to detect lumens in an endoscope image.

In some variations of the present embodiment, determining whether a predetermined position has been reached comprises where it is determined that two or more lumens are present in the at least one recorded image, estimating a position of the two or more lumens in a model of the human cavity, such as the human airways. The estimating the position may be performed using the machine learning architecture.

In some variations of the present embodiment, the method may further comprise, in response to determining that two or more lumens are present in the at least one recorded image: determining which one of the two or more lumens the endoscope enters; and updating a determined endoscope position based on the determined one of the two or more lumens. In some embodiments, determining which one of the two or more lumens the endoscope enters may be performed by analysing, in response to a determination that two or more lumens are present in the at least one recorded image, a plurality of recorded images to determine a movement of the endoscope.

In some variations of the present embodiment, building the database comprises evaluating a quality of an image of the image stream for use in the database and, in response to evaluating the quality to be above a predetermined threshold quality, generating a database entry based on the image. Thereby the determination whether an image is obtained at a previously visited location may have an increased robustness as the database may be based on high quality images, in turn reducing the risk of false positive and/or false negative determinations.

The evaluation of the quality may be performed by a machine learning data architecture trained to evaluate a quality of images.

A quality may be and/or may correspond to a suitability of the images for use in determining whether they are obtained at a previously visited location. The quality may be determined based on one or more of a light level, a contrast level, a blurriness, a sharpness, and/or a depth of focus. Alternatively or additionally, the quality may be determined based a recognisability of features from the image and/or from the number of recognisable features from the image.

In some embodiments, building the database comprises generating a database entry further based on one or more of an estimated endoscope location and an image smoothness. Thereby, the database entry may be based on an image which has a suitable smoothness for comparing an image of the stream with the image of the database.

A smoothness may determined based on one or more of a frequency analysis, e.g. the frequency content of an image, an edge detection, and/or a contrast of the image.

In some variations of the present embodiment, generating the database comprises generating a database entry, wherein the database entry is created based on a series of images and wherein the comparing comprises comparing a series of images from the stream of images with the database entry. Thus, an improved determination, e.g. a reduction of the risk of false positives and/or false negatives, may be provided, as a plurality of images and potentially a time dimension thereof may be taken into account.

The series of images may comprise and/or be a plurality of images, such as a consecutive plurality of images and/or a stream of images.

The database entry/entries may be created based on a series of dimensionally reduced images and/or may comprise a series of dimensionally reduced images.

In variations of the present embodiment, the endoscopic procedure is a bronchoscopic procedure or a colonoscopic procedure, such as a colonoscopy.

Another embodiment relates to an image processing device for recognising previously observed locations during an endoscopic procedure, said image processing device comprising a processor operationally connectable to an image sensor of an endoscope, wherein the processor is configured to perform the method according to the first aspect. The image processing device may be the VPA 20. The processor of the image processing device may be any processor, such as the processor 50 and/or the FPGA 42.

The processor may, where this is configured to perform a method using a machine learning data architecture, implement the machine learning data architecture, i.e. the processor may provide the image to the machine learning data architecture by processing the image using the machine learning data architecture. Alternatively, the processor may provide the image, a parameterized version of the image, or a dimensionally reduced version of the image to another processor e.g. outside of the image processing device, where said another processor implements the machine learning data architecture.

Figure 9:
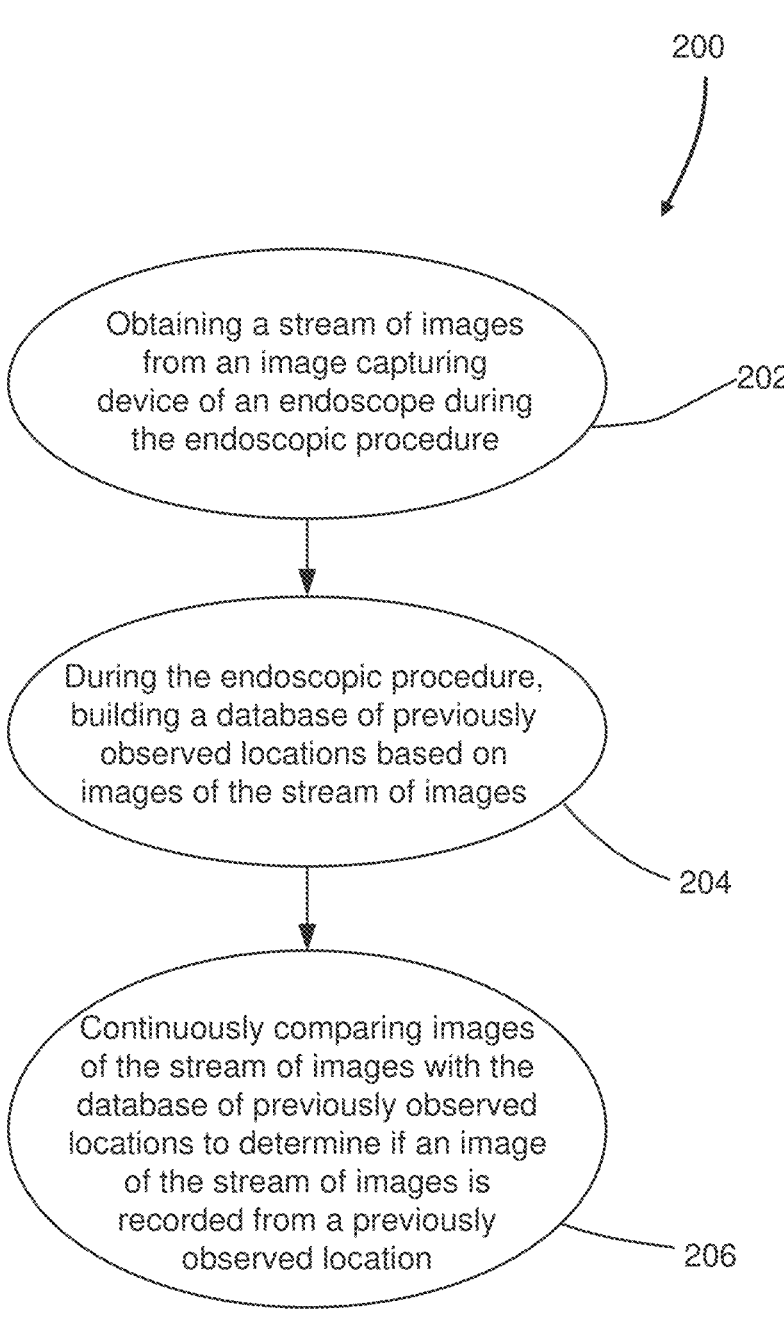
FIG. 9 is a flowchart of an embodiment of a method for recognizing previously observed locations during an endoscopic procedure.

FIG. 9 shows a flowchart 200 of an example of the foregoing embodiment of a method of recognising previously observed locations during an endoscopic procedure. The method may be performed by the VPA 20.

The method initiates, at 202, when a stream of images is obtained from the image sensor of the endoscope during the endoscopic procedure. The stream of images is obtained by the medical device interface and the FPGA and/or processor store the images in memory.

Next, at 204, during the endoscopic procedure, a database of previously observed locations is built based on images of the stream of images. The database may be referred to as prior position database.

Then, at 206, images of the stream of images are continuously compared with the database of previously observed locations to determine if an image of the stream of images is recorded from a previously observed location. In other words, the real-time images previously stored in the memory are compared with the trained model to identify physiological landmarks indicative of location. The physiological landmarks were previously identified in the training set of images with bounding boxes and labels.

The method may be performed by the VPA 20. A stream of images is obtained from the image sensor of the endoscope via the medical device interface. The image data from the image sensor may be available at the medical device interface as soon as the endoscope is connected.

A user of the VPA 20 may actuate the OD logic 56 via the GUI to initiate the procedure. Once the procedure is initiated, the OD logic 56 may cause storage of the images in the memory, for example by saving image files containing the images to the memory.

The OD logic 56 compares the images of the stream of images, e.g. input images, with the images in the trained model/database, e.g. training images, to identify objects that appear in both. If objects appearing in both are indicative of a physiological landmark labeled in the training image, the OD logic 56 determines that the physiological landmark has been reached by the tip part of the endoscope.

The OD logic 56 is furthermore configured to output an output signal indicating and/or comprising information regarding whether the input image is determined to be recorded from a previously observed location. The output signal may be presented with the display screen, as described below.

Figure 10:
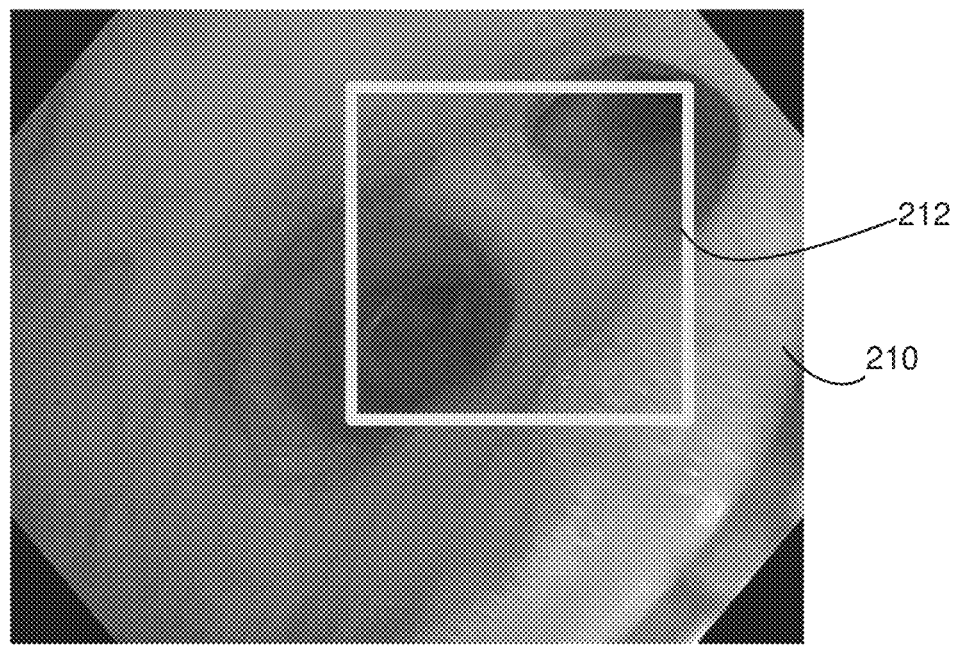
FIG. 10 is an image based on which a database entry is generated according to the method of FIG. 9.

FIG. 10 shows a view of an image 210 based on which a database entry is generated in the method described with reference to FIG. 9. The image 210 is obtained by an image sensor of an endoscope. The view of the image 210 illustrates a bifurcation in the airways, i.e. a bifurcation of the trachea into a right and left main bronchus. Based on the image 210, an entry is generated in the database including a bounding box 212 and a label, such as "bifurcation".

In some embodiments, the location at which the image 210 is obtained, i.e. at or near the bifurcation of the trachea into a right and left main bronchus, is determined and potentially stored in the database.

The database entry may comprise the input image 210 or a dimensionally reduced version thereof.

Figure 11:
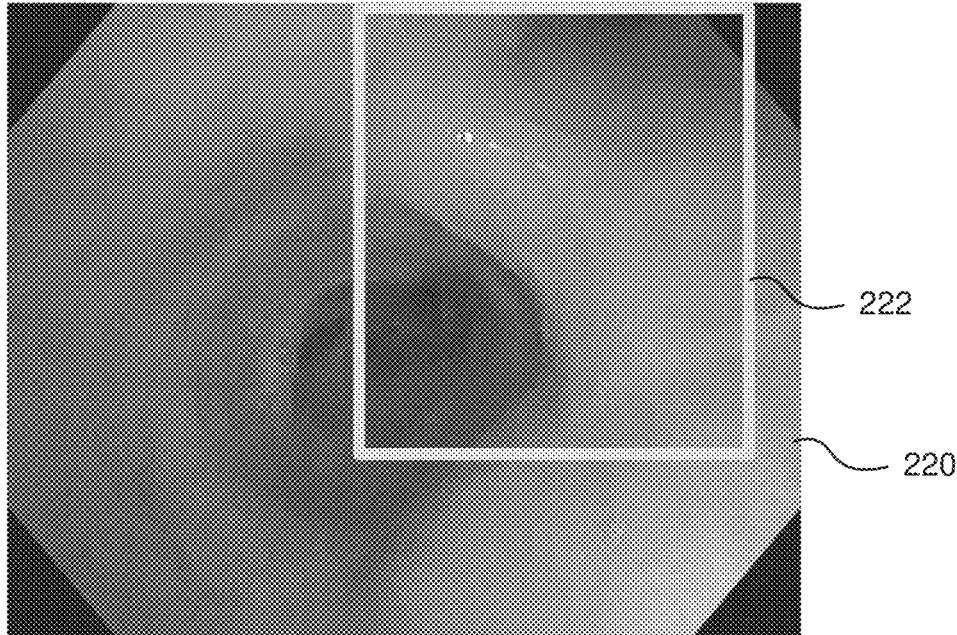
FIG. 11 shows an input image used for comparison to previously observed images.

FIG. 11 shows a view of an input image 220, which the OD logic 56 compares with the database of previously observed locations. The input image 220 includes a bounding box 222 which the OD logic 56 identified with high probability, based on the image 212, as being the "bifurcation". It can be seen that the orifices in the images are not the same size and that the image 222 appears to reflect light more than the image 212. Also, the optical axis of the image sensor appears to differ from one image to the other. These illumination and positioning artifacts are due to the fact that the camera, comprising the image sensor 16 and the LEDs 18, is very small, potentially 3.2 mm in diameter at the tip part, or less, and therefore the LEDs can emit light close to the surface tissue of the trachea or bronchus, which reflects onto the area of interest.

The following items are further variations and examples of the embodiments described with reference to FIGS. 1*a* to 5 and 9 to 11.

1. A method of recognising previously observed locations during an endoscopic procedure comprising: obtaining a stream of images from an image sensor of an endoscope during the endoscopic procedure; during the endoscopic procedure, building a database of previously observed locations based on images of the stream of images; and continuously comparing images of the stream of images with the database of previously observed locations to determine if an image of the stream of images is recorded from a previously observed location.

2. The method according to item 1, wherein the comparing comprises reducing a dimensionality of the images of the stream of images and comparing the images of reduced dimensionality with the database.

3. The method according to any of the preceding items, wherein the step of building the database comprises determining whether a predetermined position has been reached, wherein each previously observed location corresponds to a predetermined position and, where it is determined that the predetermined position has been reached, creating an entry in the database based on one or more images of the image stream.

4. The method according to item 3, wherein the determination whether a predetermined position has been reached comprises continuously analysing the recorded images of the stream of recorded images using a first machine learning data architecture, the first machine learning data architecture being trained to determine a set of anatomic reference positions, to determine if an anatomic reference position of a subset of anatomic reference positions, from the set of anatomic reference positions, has been reached.

5. The method according to any one of the preceding items, wherein building the database comprises evaluating a quality of an image of the image stream for use in the database and, in response to evaluating the quality to be above a predetermined threshold quality, generating a database entry based on the image.

6. The method according to any one of the preceding items, wherein building the database comprises generating a database entry further based on one or more of an estimated endoscope location and an image smoothness.

7. The method according to any one of the preceding items, wherein building the database comprises generating a database entry comprising a plurality of images.

8. The method according to any one of the preceding items wherein building the database comprises generating a database entry, wherein the database entry is created based on a series of images and wherein the comparing comprises comparing a series of images from the stream of images with the database entry.

9. The method according to any one of the preceding items, wherein the endoscopic procedure is a bronchoscopic procedure.

10. An image processing device for recognising previously observed locations during an endoscopic procedure, said image processing device comprising a processor operationally connectable to an image sensor of an endoscope, wherein the processor is configured to perform the method according to any one of items 1-9.

11. A display unit for displaying images obtained by an image sensor of an endoscope, wherein the display unit comprises an image processing device according to item 10.

12. An endoscope system comprising an endoscope and an image processing device according to item 10, wherein the endoscope has an image sensor and the processor of the image processing device is operationally connectable to the image sensor of the endoscope.

13. The endoscope system according to item 12 further comprising a display unit, the display unit being operationally connectable to the image processing device.

14. An endoscope system according to item 12, wherein the image processing device forms part of a display unit according to item 11.

15. A computer program product comprising program code means adapted to cause a data processing system to perform the steps of the method according to any one of items 1-9, when said program code means are executed on the data processing system.

16. The computer program product according to item 15, wherein said computer program product comprises a non-transitory computer-readable medium having stored thereon the program code means.

As described above with reference to FIGS. 1*a*, 1*b*, 2 to 5 and below with reference to FIGS. 12 to 14, the visualization system can determine the location of an endoscope in a phantom model. The phantom model is a physical model of a cavity of a human body. The image processing device comprises a processor operationally connectable to an image sensor of an endoscope. The processor is configured to: obtain a stream of images from the image sensor of the endoscope; continuously process images of the stream of images to determine if a predetermined reference position has been reached; and in response to determining that the predetermined reference position has been reached, update an estimated location of the endoscope.

By the image processing device being configured to process images to determine if a predetermined reference position has been reached, further devices, such as echo signalling devices or the like, to determine a location of the endoscope in the phantom model may be dispensed with. This may, in turn, allow for a simpler system and make handling of the equipment during the navigation of the endoscope in the phantom model simpler, as no additional devices may need to be handled simultaneously with the navigation of the endoscope.

A predetermined reference position may be any position within the phantom model. A predetermined reference position may be and/or may correspond to a position, which the endoscope such as a distal end thereof, can take in the phantom model. In some embodiments, the predetermined reference position is a position at which a visual characteristic occurs, which allows the image processing device to estimate, based on the image, the position of the endoscope. Alternatively or additionally, a predetermined reference position may be a position, at which a furcation occurs in the phantom model. For instance where the phantom model represents the human airways, a furcation may occur at the position in the phantom model representing the position in the human airways, at which the trachea bifurcates into the left and right bronchus, and/or where bronchi and/or bronchioles furcate.

The estimated endoscope location may correspond to or be a part or segment of the phantom model, in which the endoscope is determined to be.

The endoscope location may be a location of a tip part of an endoscope. Alternatively or additionally, the endoscope location may be a location of the endoscope in a phantom model, such as a cavity of the phantom model, and/or in a model, e.g. a computer model, of the phantom model. The endoscope location may be or indicate a segment of the phantom model.

In some embodiments, the processor may be configured to add to the image(s) an estimated endoscope location, potentially as an overlay.

The phantom model may be a physical model of the human lung tree or of the human colon. The phantom model may resemble and/or model the human cavity The phantom model may comprise one or more visual markers. The one or more visual markers may be arranged in the phantom model, potentially so that the one or more visual markers can be recognised in images from the endoscope. The one or more visual markers, such as each visual marker may comprise a QR code, a texture pattern, a pattern of varying colour and/or contrast. The one or more visual markers may be configured to be recognisable by the image sensor and/or by the image processing device from the images obtained by the image sensor. The one or more visual markers may be suitable for and/or configured to allow the image processing device to provide an augmented image based on the visual markers.

In some embodiments, the processor may further be configured to store one or more earlier estimated locations of the endoscope. Alternatively or additionally, the processor may be configured to estimate a location, such as a current location, of the endoscope in the phantom model based on the image(s) from the image stream and at least one earlier estimated location.

Alternatively or additionally, the processor may be configured to provide guidance to the user, potentially so as to guide to user to navigate the endoscope to a predetermined location in the phantom model and/or guide the user to navigate the endoscope to a plurality of predetermined location in a specific predetermined order. Thereby, the user may be assisted in carrying the endoscopic procedure, which the user performs in the phantom model, according to an established "best practice". The processor may be configured to provide the guidance based on a determined estimated location of the endoscope and/or, where one or more earlier estimated locations of the endoscope is stored, based on at least one of the one or more earlier estimated location.

Where an output signal is provided by the processor, the output signal may comprise the guidance, potentially in the form of instructions and/or one or more predetermined location(s).

In some embodiments, where the phantom model comprises one or more visual markers, the image processing device may be configured to analyse an image from the stream of images to determine if one or more visual markers are present in the image. The image processing device may further be configured to, in response to determining that one or more visual markers are present in the image, determine the location of the endoscope based on the determined one or more visual markers. Alternatively or additionally, the image processing device may further be configured to, in response to determining that one or more visual markers are present in the image, augment the image based on the determined one or more visual markers.

A further aspect of the present disclosure relates to a phantom model, the phantom model being a physical model of a cavity of a human body, wherein the phantom model comprises one or more visual markers. The one or more visual markers may be suitable for being obtained by an image sensor of an endoscope, when the endoscope is navigated in the phantom model, such as in an interior of the phantom model.

In some embodiments, the image processing device is configured to continuously process the images using a machine learning data architecture to determine if a reference position has been reached, the machine learning data architecture being trained to determine a predetermined reference position. Thereby, a robust recognition of the predetermined reference positions may be provided.

The machine learning data architecture may be a first machine learning data architecture.

The (first) machine learning data architecture may be trained by being provided with a training data set comprising a number, such as a large number, such as 100 or more, image streams, each potentially comprising a plurality of images, from an endoscope and having a human operator determine the predetermined reference position, at which the images have been obtained in the phantom model. The training data set may comprise one or more images showing reference positions inside a phantom model, such as inside a cavity of the phantom model. The images may be from a video stream of an image device of an endoscope. The machine learning data architecture may be trained to optimise towards a F score, such as a F1 score or a Fβ, which it will be appreciated is well known in the art. The machine learning data architecture may be trained using the training data set and corresponding associated predetermined reference positions. Potentially, the anatomic reference positions may be associated by a plurality of people.

While phantom models may resemble and/or model a human cavity, the textures, shapes, and/or features from the phantom models are typically somewhat different from that of a real human cavity. Thus, by training the machine learning data architecture using images obtained in a phantom model, a more robust and/or reliable determination of an endoscope location in a phantom model may be provided by the machine learning data architecture.

In some embodiments, the reference position may be a reference position of a subset of predetermined reference positions. The subset of predetermined reference position may be a subset from a set of predetermined reference positions. The set may comprise the subset of predetermined reference positions and at least one further reference position.

In some embodiments, a subset of predetermined reference positions comprises two or more reference positions from the set of predetermined reference positions, such as some but not all of the predetermined reference positions from the set of predetermined reference positions.

In some embodiments, the image processing device may be configured to determine a subset of predetermined reference positions based on the estimated endoscope location, such as a previously estimated endoscope location.

In some embodiments, the machine learning data architecture may alternatively or additionally be trained to determine a set of predetermined reference positions. A set of predetermined reference positions may comprise two or more predetermined reference positions.

In some embodiments, the image processing device may be configured to detect openings and/or lumens in an image of the image stream.

In some embodiments, the determination whether a predetermined position has been reached further comprises to continuously analyse the recorded images to determine if two or more lumens, potentially of a branching structure, are present in at least one of the recorded images. The determination whether two or more lumens are present may be carried out by the (first) machine learning data architecture. Alternatively, the determination if two or more lumens are present in the at least one recorded image may be performed using a second machine learning architecture trained to detect lumens in an endoscope image.

In some embodiments, for instance where the phantom model is a model of a human lung tree, the processor may be configured to estimate a location of the endoscope in response to a determination that two or more lumens are present in the at least one recorded image. Alternatively or additionally, a predetermined reference position may be a position, at which a branching occurs, i.e. where two or more lumens are present in the at least one recorded image.

The processor may be configured to, where it is determined that two or more lumen are present in the image(s), determine a location of these in the phantom model. The processor may further be configured to indicate a location of the two or more lumen, such as which part of the phantom model, the endoscope will enter if entering either of the two or more lumen. For instance, where the phantom model is a model of the human lung tree and two lumens are detected, the image processor may determine that the two lumen lead to a phantom model portion modelling a left and phantom model portion modelling a right main bronchus, respectively, and indicate this, e.g. by an overlay on each of the two lumen.

In some embodiments, the image processing device may further be configured to, in response to determining that two or more lumens are present in the at least one recorded image: determining which one of the two or more lumens the endoscope enters; and updating an estimated endoscope location based on the determined one of the two or more lumens. In some embodiments, determining which one of the two or more lumens the endoscope enters may be performed by analysing, in response to a determination that two or more lumens are present in the at least one recorded image, a plurality of recorded images to determine a movement of the endoscope.

The processor may, where this is configured to use a machine learning data architecture, such as a first, a second, and/or a third machine learning data architecture, implement the machine learning data architecture, i.e. the processor may provide the image to the machine learning data architecture by processing the image using the machine learning data architecture. Alternatively, the processor may provide the image, a parameterized version of the image, or a dimensionally reduced version of the image to another processor e.g. outside of the image processing device, where said another processor implements the machine learning data architecture.

In some embodiments the phantom model is a three-dimensional model of the human body cavity.

The three-dimensional (3D) model of human cavity may be a 3D model of the human airways or colon. The 3D model may be configured to resemble the human cavity. The 3D model may be configured to receive an endoscope.

The three-dimensional model of the human body cavity may be made from a polymer material. The three-dimensional model may be approximately scale 1:1 of the human cavity, which it models.

In some embodiments the image processing device is further configured to: output an output signal based at least in part on one or more of the images of the stream of images. Thereby, the estimated endoscope location, the images from the endoscope, and/or other data based on the images may be signalled to another device.

The output signal may comprise one or more images of the stream of images. Alternatively or additionally, the output signal may comprise the estimated endoscope location and/or may comprise an indication, such as a coordinate, a text, and/or a visual marker or overlay, indicating the estimated endoscope location.

The image processing device may comprise an output signal port for outputting the output signal. The output signal port may comprise a plug and/or a socket for interconnection with another device and/or may comprise a wireless communication interface.

The output signal may be configured to be received by a display unit and/or may be configured to be displayed on a display unit.

In some embodiments the image processing device is further configured to: augment an image from the stream of images by obtaining a computer model representing at least a part of the phantom model, determining an estimated position of the endoscope relative to the part of the phantom model, and based on the estimated position and the computer model, augmenting the image, wherein the output signal is based at least in part on the augmented image.

Thereby, further information, such pathological conditions, may be emulated, thereby providing an improved training of the user, since the user may react to these.

The computer model may be determined based on one or more image(s) from the stream or images and/or a structure of the phantom model. The computer model may represent a geometry of the part of the phantom model, may be and/or comprise a plane. Additionally or alternatively, the computer model may represent a three-dimensional geometry of the part of the phantom model.

In some embodiments, the computer model may comprise a simulation of a pathological condition.

The computer model may be selected between a plurality of computer models and/or may be, at least pseudo-, randomly generated.

The determined estimated position relative to the part of the phantom model may have same accuracy as the estimated endoscope location in the phantom and/or may be more accurate. The estimated position relative to the part of the phantom model may be determined based on image(s) and/or based on visual markers, where visual markers are provided in the phantom model. Additionally or alternatively, the estimated position may be based on knowledge and/or data about the phantom model. The knowledge and/or data may be structural knowledge of the phantom model, such as information from a CT scan thereof, information regarding the three-dimensional geometry, and/or manufacturing data, such as CAD data, of the phantom model.

The output signal may alternatively or additionally be and/or may comprise the augmented image, potentially configured to be displayed on a display unit.

The augmentation of the image may comprise adding features, potentially in an overlay, to the image, such as a polyp, a scratch, a section with specific colour, and/or a section with specific surface.

In some embodiments the computer model comprises a virtual light source simulating light from one or more light sources of the endoscope. Thereby, a more realistic augmentation of the image may be provided.

The virtual light source may be based on an orientation and/or a position of the endoscope. Light from the virtual light source may be determined, potentially by the image processing device, based on the images.

In some embodiments the augmenting the image comprises adding to the image an overlay resembling human tissue.

The overlay may be based on visual markers, where the phantom model comprises visual markers.

In some embodiments, the image processing device may be configured to augment the image to include a virtual surface, such as a three-dimensional surface. The virtual surface may be adapted to resemble or imitate a polyp.

In some embodiments the image processing device is configured to augment the image based on information about the computer model, the information being based on physical properties of the phantom model. Thus, the geometry of the phantom model near the section, at which the image was obtained may be taken into account when an augmentation is to, thereby allowing for a more realistic augmentation of the image.

The information about the computer model may be information relating to the geometry of the phantom model. For instance, the information may be based on manufacturing information, such as CAD information or 3D print information, a CT scan of the phantom model, or a MR scan of the phantom model.

In some embodiments, the computer model may be a rendering of the phantom model and/or may be synthesised based on the phantom model. The computer model may be a virtual representation of the phantom model or an estimated virtual representation of the phantom model.

In some embodiments, the augmentation of the image may be based on a synthesised image from the computer model. For instance, the image processing device may, based on the computer model, be configured to generate a synthesised image, which estimates an image which would be obtained from the endoscope, when the endoscope is at a given location in the model. Alternatively or additionally, the image processing device may be configured to generate a synthesised outcome space, potentially comprising a plurality of synthesised images and, based on a match between the image of the image stream and the synthesised images, determine an estimated location of the endoscope and/or augment the image.

In some embodiments the image processing device is further configured to determine, based on an image of the image stream, if a tool is visible in the image and, if a tool is visible, augment the image based on the determination that a tool is visible. Thereby, the augmented images may allow for simulating a biopsy from the phantom model, again allowing for an improved training of the user.

In some embodiments, the image processing device may be configured to determine the type of tool and augment the image based on the type of tool. Alternatively or additionally, the image processing device may determine a position of the tool in the image and augment the image accordingly.

The image processing device may be configured to determine if a tool is visible in the image using a, potentially third, machine learning data architecture trained to determine if a tool is visible. The machine learning data architecture may be trained by providing to the machine learning data architecture a training data set comprising a plurality, such as a large number, of images obtained by an endoscope, and by a user classifying if a tool is visible in the image or not. In some embodiments, the image processing device may be configured to identify a tool, i.e. a type of tool, potentially using the (third) machine learning data architecture and/or a visual marker provided on the tool. In some embodiments, the image processing device may further be configured to augment the image in response to an identification of the tool.

In some embodiments the image processing device is further configured to: estimate a quality parameter of a navigation of the endoscope in the phantom model based on the images of the image stream. Thereby, a quality of the endoscopy may be provided to the user, again allowing for an improved training of the user.

The processing device as described above is configured to implement a method for determining the location of the endoscope in the phantom model. In an embodiment, the method comprises: obtaining a stream of images from an image sensor of an endoscope; continuously processing images of the stream of images to determine if a predetermined reference position has been reached; and in response to determining that a predetermined reference position has been reached, updating an estimated location of the endoscope.

The quality parameter may be based on, comprise, and/or be an estimate of the time the endoscope has spent in a segment or at an estimated location, and/or an estimate of if all locations from a set of locations in the phantom model have been visited. Alternatively or additionally, the quality parameter may be based on a determination whether a navigation of the endoscope in the phantom model would have caused harm to a patient, if the endoscope had been navigated identically in a human cavity, which the phantom model resembles.

The foregoing method may be executed according to processing instructions embedded in a computer program product adapted to cause a data processing system to perform the method.

Figure 12:
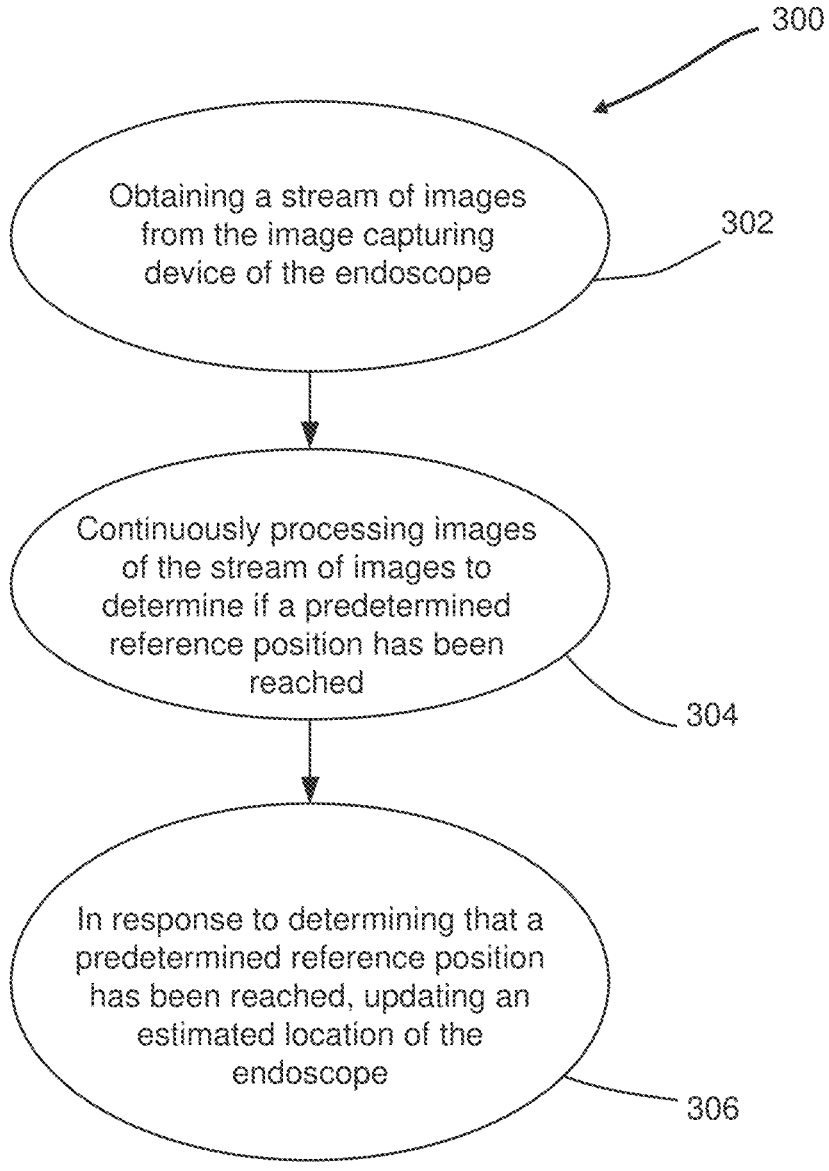
FIG. 12 is a flowchart of another embodiment of a method for recognising anatomic reference positions and updating a position of the endoscope.

FIG. 12 shows a flowchart 300 of an example of the foregoing embodiment of a method for determining the location of an endoscope in a phantom model. The phantom model is a physical model of a cavity of a human body. The method may be performed by the VPA 20.

The method initiates, at 302, by obtaining a stream of images from an image sensor of an endoscope. The stream of images is obtained by the medical device interface and the FPGA and/or processor store the images in memory.

Next, at 304, images of the stream of images are continuously processed to determine if a predetermined reference position has been reached. In other words, the real-time images previously stored in the memory are compared with the trained model to identify physiological landmarks indicative of location, at least some of which are predetermined as reference positions. The physiological landmarks were previously identified in the training set of images with bounding boxes and labels. For example, the OD logic 56 may compare the images of the stream of images, e.g. input images, with the images in the trained model/database, e.g. training images, to identify objects that appear in both. If objects appearing in both are indicative of a physiological landmark labeled in the training image, the OD logic 56 determines that the predetermined reference position has been reached by the tip part of the endoscope.

Then, at step 306, an estimated location of the endoscope in the phantom model is updated in response to determining that a predetermined reference position has been reached.

A user of the VPA 20 may actuate the OD logic 56 via the GUI to initiate the procedure. Once the procedure is initiated, the OD logic 56 may cause storage of the images in the memory, for example by saving image files containing the images to the memory.

The OD logic 56 compares the input images with the training images in the trained model/database to identify objects that appear in both. If objects appearing in both are indicative of the predetermined reference position, the OD logic 56 determines that the predetermined reference position has been reached by the tip part of the endoscope.

The OD logic 56 is furthermore configured to output an output signal indicating and/or comprising information regarding whether the input image is determined to be recorded from a previously observed location. The output signal may be presented with the display screen, as described below.

In response to determining that the predetermined reference position has been reached, the OD logic 56 updates an estimated location of the endoscope. The updated estimated location is stored in the memory. In other embodiments, the updated estimated location may be stored in an external memory and/or an internal memory of a memory device (not shown), to which the VPA 20 may be connectable, e.g. by a wired and/or a wireless connection. Alternatively or additionally, the updated estimated location may be stored on a server accessible to the VPA 20 by means of a wired and/or wireless connection.

The OD logic 56 is furthermore configured to output an estimated location output signal indicating and/or comprising information regarding an estimated location of the endoscope. The estimated location output signal may be presented with the display screen, as described below.

Figure 13:
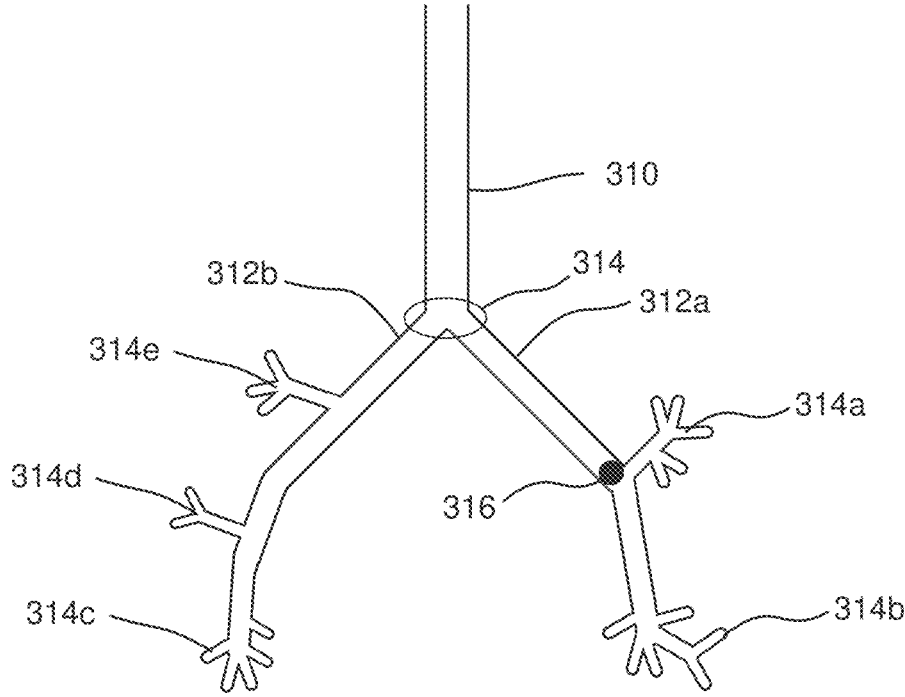
FIG. 13 shows a visual model of a phantom model used in accord with the method of FIG. 12.

FIG. 13 shows a visual model of a phantom model. The phantom model can be a three-dimensional model of human airways. The visual model is a computer model of the phantom model. The view shown in FIG. 13 is not necessarily to scale and the relative size of individual parts or elements therein does not necessarily correspond to the relative sizes of the parts or elements of the phantom model which they model. The visual model illustrates parts, corresponding to the phantom model, representing a trachea 310, a left primary bronchus 312a, and a right primary bronchus 312b, secondary bronchi 314a-314e, as well as some bronchioles. A first estimated location, denoted by numeral 314, corresponds to a predetermined reference position representing the "bifurcation" position illustrated and described with reference to FIG. 5 in the input image

220. A second estimated location, denoted by numeral 316, corresponds to a predetermined reference position representing the end of the primary bronchus 312a and the entry to the secondary bronchi 314a. To identify the second estimated position, the training database would be provided with a plurality of images, perhaps hundreds or even thousands, taken by endoscopes at that location and labelled as described above. An experienced physician may observe the video stream and identify the location in the training images. Additionally or alternatively, imaging and tracking techniques, such as ultrasound, may be used to precisely determine the position of the endoscope and to correlate the live images with the position, forming the training images for the training database.

The estimated endoscope location 316 is indicated by a dot arranged at the position in the model substantially corresponding to and representing the estimated location of the endoscope in the phantom model. It should be noted that the dot need not show an exact real-time location of the endoscope but may show an approximated location or an area or part of the phantom model, in which the endoscope is estimated to be located. In other embodiments, the estimated endoscope location may alternatively or additionally be indicated by a different graphical symbol than the dot, by text, or the like.

Figure 14:
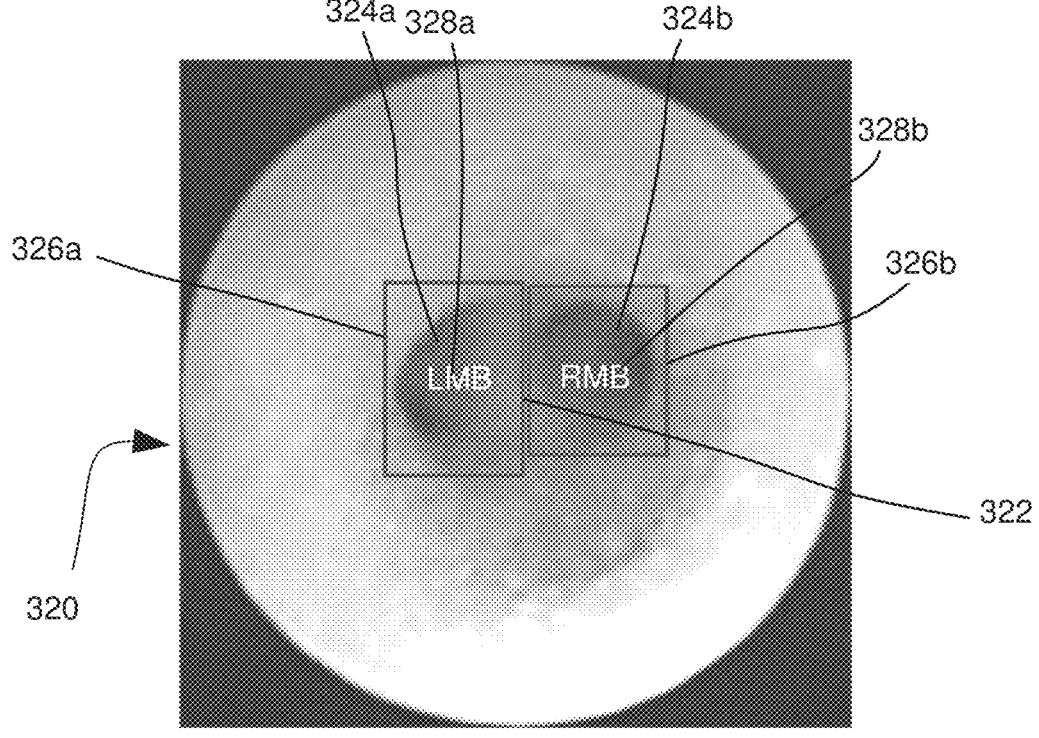
FIG. 14 shows an input image with text overlays and bounding box overlays in accord with the method of FIG. 12.

FIG. 14 shows a view of an input image 320 based on an image obtained by an image sensor of an endoscope. Based on the input image 320, the OD logic 56 identifies a first lumen 324a and a second lumen 324b of a branching 322. The OD logic 56 further determines a bounding box 326a of the first lumen 324a and a bounding box 326b of the second lumen 324b. In other embodiments, the bounding boxes 326a, 326b may be dispensed with and/or not indicated in the image 320.

The OD logic 56 moreover estimates a position of the first lumen 324a as a part of the phantom model, which part models a left main bronchus (LMB), and a position of the second lumen 324b as a part of the phantom model, which part models the right main bronchus (RMB). The image processing device determines this based on the image and/or an estimated location of the endoscope. The OD logic 56 indicates this with a text overlay 328a indicating the estimated position of the first lumen 324a and a text overlay 328b indicating the estimated position of the second lumen 324b. The OD logic 56 may further determine that the endoscope enters a lumen, such as the first lumen 324a, and update the endoscope location correspondingly, e.g. to LMB. In other embodiments, the text overlays 328a, 328b may be dispensed with and/or not indicated in the image 320.

The following items are further variations and examples of the embodiments described with reference to FIGS. 1a, 1b, 2 to 5, and 12 to 14.

1. An image processing device for determining the location of an endoscope in a phantom model, the phantom model being a physical model of a cavity of a human body, wherein the image processing device comprises a processor operationally connectable to an image sensor of an endoscope, the processor being configured to: obtain a stream of images from the image sensor of the endoscope; continuously process images of the stream of images to determine if a predetermined reference position has been reached; in response to determining that the predetermined reference position has been reached, updating an estimated location of the endoscope.

2. The image processing device according to item 1, wherein the image processing device is configured to continuously process the images using a machine learning data architecture to determine if a reference position has been reached, the machine learning data architecture being trained to determine a predetermined reference position.

3. The image processing device according to any one of the preceding items, wherein the phantom model is a three-dimensional model of the human body cavity.

4. The image processing device according to any one of the preceding items, wherein the image processing device is further configured to: output an output signal based at least in part on one or more of the images of the stream of images.

5. The image processing device according to item 4, wherein the image processing device is further configured to: augment an image from the stream of images by obtaining a computer model representing at least a part of the phantom model, determining an estimated position of the endoscope relative to the part of the phantom model, and based on the estimated position and the computer model, augmenting the image, wherein the output signal is based at least in part on the augmented image.

6. The image processing device according to item 5, wherein the computer model comprises a virtual light source simulating light from one or more light sources of the endoscope.

7. The image processing device according to item 5 or 6, wherein the augmenting the image comprises adding to the image an overlay resembling human tissue.

8. The image processing device according to any one of items 5-7, wherein the image processing device is config-ured to augment the image based on information about the computer model, the information being based on physical properties of the phantom model.

9. The image processing device according to any one of items 5-8, wherein the image processing device is further configured to determine, based on an image of the image stream, if a tool is visible in the image and, if a tool is visible, augment the image based on the determination that a tool is visible.

10. The image processing device according to any one of the preceding items, wherein the image processing device is further configured to:

estimate a quality parameter of a navigation of the endo-scope in the phantom model based on the images of the image stream.

11. A display unit for displaying images obtained by an image processing device of an endoscope, wherein the display unit comprises an image processing device accord-ing to any one of items 1-10.

12. An endoscope system comprising an endoscope and an image processing device according to any one of items 1-10, wherein the endoscope has an image sensor and the processor of the image processing device is operationally connectable to the image sensor of the endoscope.

13. The endoscope system according to item 12 further comprising a display unit, wherein the display unit is opera-tionally connectable to the image processing device.

14. An endoscope system according to item 13, wherein the image processing device forms part of a display unit according to item 11.

15. A method for determining the location of an endo-scope in a phantom model, the phantom model being a physical model of a cavity of a human body, wherein the method comprises: obtaining a stream of images from an image sensor of an endoscope; continuously processing images of the stream of images to determine if a predeter-mined reference position has been reached; and in response to determining that a predetermined reference position has been reached, updating an estimated location of the endo-scope.

16. A computer program product comprising program code means adapted to cause a data processing system to perform the steps of the method according to item 15, when said program code means are executed on the data process-ing system.

17. The computer program product according to item 16, wherein said computer program product comprises a non-transitory computer-readable medium having stored thereon the program code means.

As described above with reference to FIGS. 1a, 1b, 2 to 5 and below with reference to FIGS. 15 to 17, the visual-ization system can determine a quality measure of an endoscopic procedure based on estimated locations of a lumen.

Embodiments of a method for estimating a quality mea-sure of an endoscopic procedure performed using an endo-scope are also provided herein. In one embodiment, the method comprises: obtaining a stream of images captured by the image sensor of the endoscope; processing the stream of images to estimate locations of a lumen in the stream of images, and determining a quality measure of the endo-scopic procedure based on the estimated locations of the lumen.

In some embodiments, the OD logic 56 is configured to process the stream of images to estimate the location of the lumen in the stream of images and to determine the quality measure of the endoscopic procedure based on the estimated location of the lumen. The quality measure may be stored in the memory. Alternatively/additionally, the quality measure may be provided to a display screen or module to be presented to an operator, possibly together with endoscope images.

In a variation of the present embodiment, the OD logic 56 is configured to: obtain a stream of images captured by the image sensor of the endoscope; process the stream of images to estimate locations of a lumen in the stream of images, and determine a quality measure of the endoscopic procedure based on the estimated locations of the lumen. Conse-quently, by determining a location of a lumen and using the location for estimating a quality measure a simple method of determining a quality measure is provided.

Alternatively, the quality measure may be configured to detect the lumen using a non-adaptive method relying on static rules. As an example, the processor may be configured to detect a lumen by using a method comprising: finding a set of connected pixels having an intensity value below a first threshold. The first threshold may be an absolute threshold or a threshold determined based on the average intensity in an image. A group of connected pixels may be a set of pixels, where each pixel shares an edge or a corner with at least one other pixel in the set of pixels. A lumen may be detected if a set of connected pixels is found having a size above a second threshold.

The quality measure may be presented to the user during the procedure e.g. on a display. Alternatively, the quality measure may be presented to the user after the procedure has been completed and/or stored in a memory unit connected to the processor of the image processing device.

In some variations of the present embodiment, the OD logic 56 is configured to estimate the location of the lumen by providing the stream of images to a machine learning data architecture trained to identify the location of lumens in endoscope images. Consequently, an effective and reliable way of determining positions of lumens is provided.

The machine learning data architecture may be a supervised machine learning architecture. The machine learning data architecture may be trained by obtaining a training data set comprising endoscope images of different parts of different body cavities and for each endoscope image having a human operator identify a lumen (if present) e.g. a human operator may for each image firstly specify if a lumen can be seen in the image (if the image sensor is pointing towards a wall of the body cavity no lumen is visible), and secondly the location of the lumen. If a quality measure for a particular type of endoscopic procedure is determined, then the training data set may comprise endoscope images from that particular type of endoscopic procedure. As an example, if the quality measure is for a colonoscopy procedure, then the training data set may comprise endoscope images from different colonoscopy procedures on different patients.

The location of the lumen may be a center of the lumen or a circumference of the lumen. The circumference of the lumen may be a circle e.g. the smallest circle that encompasses the lumen or the largest circle that can be fully contained within the lumen. Alternatively, the circumference may be a curve substantially arranged above the border of the lumen. The processor may implement the machine learning data architecture, i.e. the processor may provide the image to the machine learning data architecture by processing the image using the machine learning data architecture. Alternatively, the processor may provide the image, a parameterized version of the image, or a dimensionally reduced version of the image to another processor e.g. outside of the image processing device, where said another processor implements the machine learning data architecture.

In some embodiments, the machine learning data architecture is an artificial neural network such as a deep structured learning architecture.

The location of the lumen in the image may indicate what area of the circumference of the colon is being investigated. Consequently, by using the estimated location of the lumen in the image for determining a quality measure, the quality measure may indicate if all parts of the colon have been sufficiently investigated.

In some embodiments, the processor is further configured to divide the circumference of the colon into a plurality of areas, based on the estimated location of the lumen in the stream of images estimate which area of the plurality of areas is being investigated, and for each area of the plurality of areas determine a quality measure. Consequently, the medical professional may be provided with information not only specifying the overall quality of the colonoscopy, but detailed information specifying the quality of different areas of the colon. This may both be useful information for the medical professional during the procedure and after the procedure.

The circumference of the colon may be divided into equally large areas e.g. four equally large areas or 8 equally large areas. As an example, the areas may be upper left, upper right, lower left, and lower right.

In some embodiments, each area of the plurality of areas corresponds to an image zone of the stream of images and wherein the processor is configured to estimate that a particular area of the plurality of areas is being investigated if the estimated location of the lumen is arranged within the image zone of the particular area. Consequently, a simple method of estimating which area of the circumference is being investigated is provided.

The image zones may have an equal size. The image zones may be centered around the center of image. The image zone may be arranged rotationally symmetric around the center of the image. Each image zone may have an opposing image zone with the same shape but only rotated 180 degrees around the center of the image.

In the event the lumen is located in more than one image zone, it may be decided that the lumen is present in the image zone where most of the lumen is present. However, it may also be determined that the lumen is only present in an image zone if the entire lumen is present in the image zone or at least a percentage of the lumen above a threshold.

In some embodiments, the OD logic 56 is configured to, for one or more images of the stream of images where a lumen is not found, estimate which area of the plurality of areas is being investigated based on a previous image in the stream of images where a lumen if found and/or a subsequent image where a lumen is found. Consequently, by using information from a previous image or subsequent image (where a lumen is visible), it may be estimated even for images where the lumen cannot be seen which area of the circumference of the colon is being investigated.

In some variations of the present embodiment, the OD logic 56 is further configured to divide the colonoscopy procedure into a plurality of parts and for each part estimate a quality measure. Consequently, it may be secured that an efficient examination is being performed along the entire length of the colon.

In some variations of the present embodiment, each part corresponds to a section of the colon having a predetermined length, and wherein the processor is configured to process the stream of images to estimate in which section the endoscope is located. Consequently, it may be secured that an efficient examination is being performed along the entire length of the colon.

The length of each section may be 5 cm, 10 cm or 15 cm. Each section may correspond to specific anatomical positions or be defined with respect to a specific anatomic position. Examples of specific anatomical positions are: the cecum, the anus, and the entrance to the appendix. However, the location of each section may also be defined relative to a selected point e.g. the initial position of the colonoscope.

In some variations of the present embodiment, the processor is configured to process the stream of images to estimate the withdrawal speed of the endoscope and use the estimated withdrawal speed to estimate in which section the endoscope is located. Consequently, a simple method of determined the location of the endoscope is provided. This may be especially advantageous when the location of each section is defined relative to a selected point e.g. the initial position of the colonoscope.

In some variations of the present embodiment, the processor is configured to process the stream of images to determine a parameter value related to the sharpness of the images and estimate the withdrawal speed based on the parameter value. The sharpness of an image is dependent on the speed of the endoscope. Specifically, if the endoscope is moving fast the resulting images will become less sharp than if the endoscope is moving slow. Consequently, by determining the sharpness of images a simple way of estimating the withdrawal speed is provided.

The stream of images may be processed in the spatial domain and/or frequency domain to determine a parameter value related to the sharpness of the images. In the frequency domain a value may be determined specifying the percentage of energy in the image above a particular set of frequencies. A high value will be indicative of a sharp image and a low value will be indicative of a unsharp/blurry image. Alternatively, a set of frequencies may be found containing a particular amount of the energy in the image. Again, a high value will be indicative of a sharp image and a low value will be indicative of a unsharp/blurry image.

In the spatial domain the average change in intensity between neighboring pixels may be determined. A high value will be indicative of a sharp image and a low value will be indicative of a unsharp/blurry image.

The relationship between the parameter value and the withdrawal speed is dependent on a number of factors including the lightning, the optical system, the tissue type etc. In practice, it may be experimentally determined. A function may be found describing the relationship. Alternatively, a look-up table may be stored specifying the relationship.

In some variations of the present embodiment, the processor is configured to estimate the withdrawal speed of the endoscope by providing the stream of images to a machine learning data architecture trained to estimate the withdrawal speed of an endoscope during a colonoscopy procedure based on endoscope images. Consequently, an effective way of determining the withdrawal speed is provided.

The machine learning data architecture may be a supervised machine learning architecture. The machine learning data architecture may be trained by obtaining a training data set comprising a plurality of streams of endoscope images obtained from different colonoscopies, where for each stream of endoscope image the withdrawal speed is provided. In practice, when creating the training data set, the withdrawal speed may be measured using an extra measurement system. As an example, the endoscope may be provided with accelerometers enabling the withdrawal speed to be estimated. Alternatively, the withdrawal speed may be estimated by providing the insertion tube of the endoscope with markings e.g. a marking every 5 cm. The withdrawal speed may then be found by having another imaging system monitoring the anus of the patient and measuring the time it takes for a new marking to become visible. As an example, if the spacing between markings are 5 cm and the time it takes for a new marking to become visible is 20 seconds, then the withdrawal speed is estimated to be 0.25 cm/second. The extra measurement system is only needed for training, i.e. the extra measurement system is not needed when using the machine learning data structure to estimate the withdrawal speed.

In some variations of the present embodiment, the machine learning data architecture is an artificial neural network such as a deep structured learning architecture.

Figure 15:
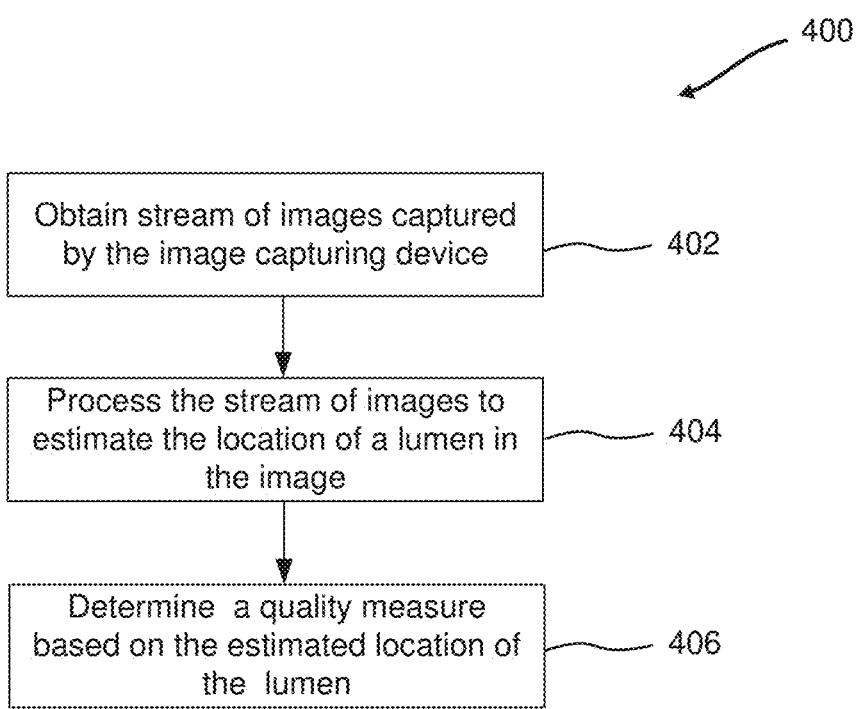
FIG. 15 is a flowchart of an embodiment of a method for determining a quality of an endoscopic procedure.
Figure 16A:
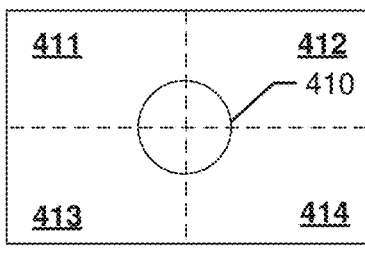
Figure 16B:
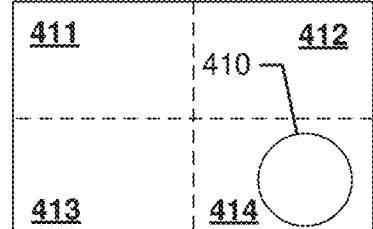
Figure 16D:
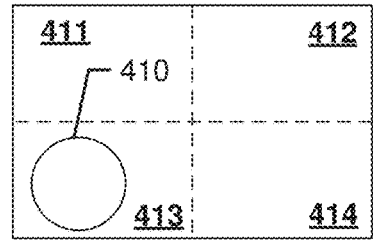
Figure 16E:
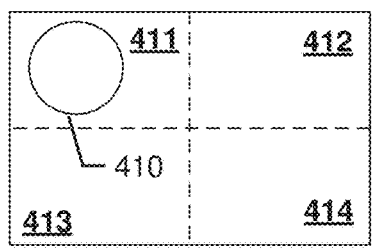

FIG. 15 shows a flowchart 400 of an example of the above-mentioned embodiment of a method for estimating a quality measure of an endoscopic procedure.

At 402, a stream of images captured by the image sensor of the endoscope is obtained. The images may be obtained in the manner described with reference to the box 202 of the flowchart 200 and/or the box 302 of the flowchart 300.

Then, at 404, the stream of images is processed to estimate locations of a lumen in the stream of images. The images may be processed in the manner described with reference to the box 304 of the flowchart 300. The training images include images of the lumen boxed and labeled.

Then, at 406, a quality measure is determined of the endoscopic procedure based on the estimated locations of the lumen.

FIGS. 16a-e show schematically images captured by an image sensor of an endoscope during a colonoscopy. The processing circuit 26 may be configured to determine a quality measure of a colonoscopy. The processing circuit 26 may be further configured to divide the circumference of the colon into a plurality of areas, and based on the estimated location of the lumen in the stream of images estimate which area of the plurality of areas is being investigated, and for each area of the plurality of areas determine a quality measure. The circumference of the colon may be divided into equally large areas e.g. four equally large areas or 8 equally large areas. As an example, the areas may be upper left, upper right, lower left, and lower right. Each area of the plurality of areas may corresponds to an image zone of the stream of images and wherein the processor is configured to estimate that a particular area of the plurality of areas is being investigated if the estimated location of the lumen is arranged within the image zone of the particular area.

In FIGS. 16a-e the circumference of the colon is divided into 4 equally large areas. The areas are upper left, upper right, lower left, and lower right. Each area of the plurality of areas corresponds to an image zone 411, 412, 413, and 414 of the stream of images. In particular, the area upper left of the circumference corresponds to the image zone 411, the area upper right of the circumference corresponds to the image zone 412, the area lower left of the circumference corresponds to the image zone 413, and the area lower right of the circumference corresponds to the image zone 414. The processing circuit 26 may be configured to estimate that a particular area of the plurality of areas is being investigated if the estimated location of the lumen is arranged within the image zone of the particular area. Thus, if the lumen 410 is located in the image zone 411 (see FIG. 16e) then it will be determined that lower right area is being investigated, if the lumen 410 is located in the image zone 412 (see FIG. 16b) then it will be determined that lower left area is being investigated, if the lumen 410 is located in the image zone 413 (see FIG. 16d) then it will be determined that upper right area is being investigated, and if the lumen 410 is located in the image zone 414 (see FIG. 16c) then it will be determined that the upper left area is being investigated. The quality measure for each area may be based on the amount of time spend on investigating the area e.g. the quality measure may be based on one or more thresholds. A first threshold may be used to determine the quality measure. Thus, if the medical professional uses more time than the first threshold on investigating an area, then a high quality measure may result. Additionally, a second first threshold may be used to determine the quality measure. Thus, if the medical professional uses more time than the second threshold but less than the first threshold on investigating an area, then a mediocre quality measure may result, and if the medical professional uses less time than the second threshold then a low quality measure may results.

Figure 17:
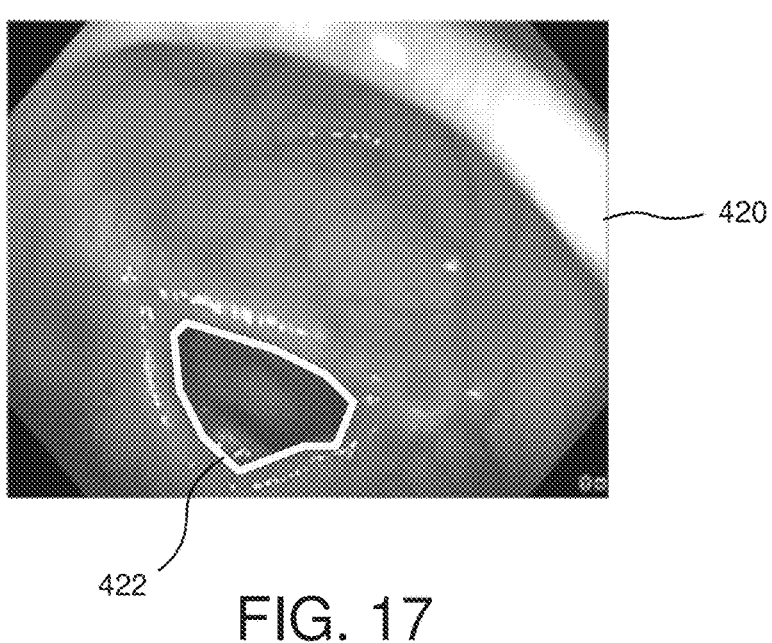
FIG. 17 shows an image of a training dataset.

FIG. 17 illustrates how a machine learning data architecture may be trained to estimate locations of a lumen in endoscope images. Shown is a single image 420 of a training data set. A typical training data set comprises endoscope images of different parts of the colon from the different procedures, i.e. endoscope images from a significant number of endoscope examinations. To train the machine learning data architecture a human operator indicates the location of the lumen 422. The location of the lumen is indicated by drawing up the circumference of the lumen 422.

Figure 18:
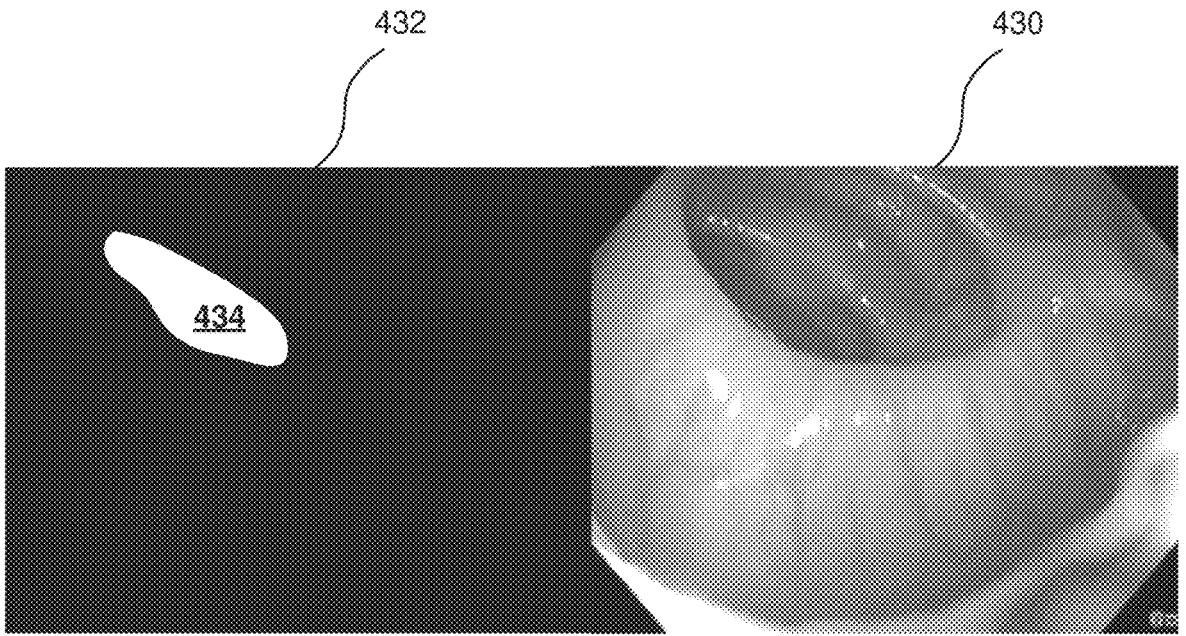
FIG. 18 shows an image to be evaluated and the output after the images is evaluated.

FIG. 18 illustrates how a lumen may be identified in endoscope images. The lumen is identified using a machine learning data architecture trained to estimate the location of a lumen in endoscope images as disclosed in relation to FIG. 17. In FIG. 18, the input image 430 is shown to the right and the output from the machine learning data architecture 432 is shown to the left. As the machine learning data architecture has been trained to estimate the circumference of a lumen 434, the circumference or periphery of the lumen 434 and its location are estimated.

Figure 19:
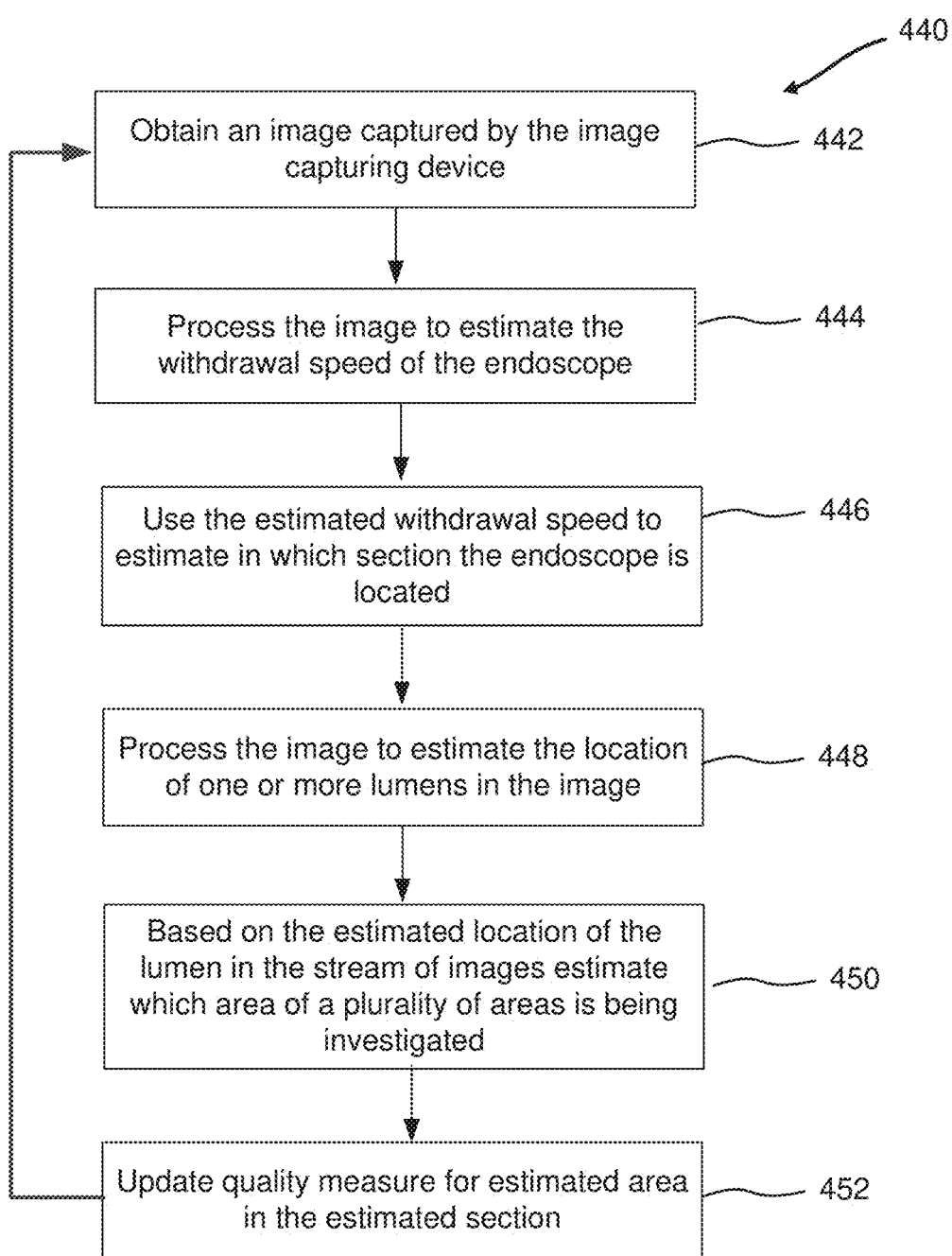
FIG. 19 is a flowchart of another embodiment of a method for determining a quality of an endoscopic procedure.

FIG. 19 shows a flowchart of a method 440 for estimating quality measures of a colonoscopy procedure performed using an endoscope, the endoscope comprising an image sensor. At 442, an image captured by the image sensor of the endoscope is obtained. Then, at 444 the obtained image is processed to estimate the withdrawal speed of the endoscope. Next, at 446, the estimated withdrawal speed is used to estimate in which section of a plurality of sections of the colon the endoscope is located. Each section of the plurality of sections may have a predetermined length e.g. each section may have a length of 5 cm, 10 cm or 15 cm.

Then, at 448 the image is processed to estimate the location of a lumen.

Next, at 450, it is estimated what area of a plurality of areas of the circumference of the colon is being investigated based on the estimated location of the lumen e.g. in the same way as disclosed in relation to FIGS. 16a-e.

Finally, the quality measure for the estimated area of the circumference of the colon for the estimated section is updated at 452. As an example, if the quality measure for each area is based on the amount of time spend on investigating the area, then the quality measure for the estimated area of the circumference of the colon for the estimated section may be updated based on how often a new image is obtained e.g. if a new image is obtained with a frequency of 60 Hz then the amount of time spend may be increased with 1/60 seconds.

Finally, the method returns to 442, where a new image is obtained.

The frequency with which a new image is obtained may be the same as the frequency of the image sensor but it may also be lower e.g. only every second or every fourth captured image may be processed to estimate a quality measure.

The final output of the method after the colonoscopy has been completed is a quality measure for each area of the circumference of the colon for each section of the colon. Thus, if the colon is divided into 10 sections and the circumference of the colon is divided into 4 areas, then a total of 40 quality measures will be estimated. This will allow the medical professional not only to obtain an overall evaluation of the quality of the procedure, but a detailed map of the quality of the different parts of the procedure. This may also assist the medical professional in performing a high quality procedure if the quality measures are presented to the medical professional during the colonoscopy procedure, as the medical professional may wait to withdraw the endoscope from the current section of the colon until all areas of the circumference of the current section have been properly investigated. It should be noted that the steps of the method may be performed in different order e.g. steps 448 and 450 may be performed before steps 444 and 446.

The following items are further variations and examples of the embodiments described with reference to FIGS. 1a, 1b, 2 to 5, and 15 to 17.

1. An image processing device for estimating a quality measure of a endoscopic procedure performed using an endoscope, the endoscope comprising an image sensor, the image processing device comprising a processor operationally connectable to the image sensor, wherein the processor is configured to: obtain a stream of images captured by the image sensor of the endoscope; process the stream of images to estimate locations of a lumen in the stream of images, and determine a quality measure of the endoscopic procedure based on the estimated locations of the lumen.

2. An image processing device according to item 1, wherein the processor is configured to estimate the location of the lumen by providing the stream of image to a machine learning data architecture trained to identify the location of lumens in endoscope images.

3. An image processing device according to items 1 or 2, wherein the endoscopic procedure is a colonoscopy.

4. An image processing device according to item 3, wherein the processor is further configured to divide the circumference of the colon into a plurality of areas, based on the estimated location of the lumen in the stream of images estimate which area of the plurality of areas is being investigated, and for each area of the plurality of areas determine a quality measure.

5. An image processing device according to item 4, wherein each area of the plurality of areas corresponds to an image zone of the stream of images and wherein the processor is configured to estimate that a particular area of the plurality of areas is being investigated if the estimated location of the lumen is arranged within the image zone the particular area.

6. An image processing device according to any one of items 1 to 5, wherein the processor is further configured to divide the colonoscopy procedure into a plurality of parts and for each part estimate a quality measure.

7. An image processing device according to item 6, wherein each part corresponds to a section of the colon having a predetermined length, and wherein the processor is configured to process the stream of images to estimate in which section the endoscope is located.

8. An image processing device according to item 6, wherein the processor is configured to process the stream of images to estimate the withdrawal speed of the endoscope and use the estimated withdrawal speed to estimate in which section the endoscope is located.

9. An image processing device according to item 8, wherein the processor is configured to process the stream of images to determine a parameter value related to the sharpness of the images and estimate the withdrawal speed based on the parameter value 10. An image processing device according to item 8, wherein the processor is configured to estimate the withdrawal speed of the endoscope by providing the stream of images to a machine learning data architecture trained to estimate the withdrawal speed of an endoscope during a colonoscopy procedure based on endoscope images.

11. A display unit for displaying images obtained by an image sensor of an endoscope, wherein the display unit comprises an image processing device according to any one of items 1 to 10.

12. An endoscope system comprising an endoscope and an image processing device according to any one of items 1 to 10, wherein the endoscope has an image sensor and the processor of the image processing device is operationally connectable to the image sensor of the endoscope.

13. A method for estimating a quality measure of an endoscopic procedure performed using an endoscope, the endoscope comprising an image sensor, wherein the method comprises: obtain a stream of images captured by the image sensor of the endoscope; process the stream of images to estimate locations of a lumen in the stream of images, and determine a quality measure of the endoscopic procedure based on the estimated locations of the lumen.

14. A computer program product comprising program code means adapted to cause a data processing system to perform the steps of the method according to item 13, when said program code means are executed on the data processing system.

15. A computer program product according to item 14, wherein said computer program product comprises a non-transitory computer-readable medium having stored thereon the program code means.

As described above with reference to FIGS. 1*a*, 1*b*, 2 to 5 and below with reference to FIGS. 20 to 23*b*, the visualization system can determine a quality measure of the bronchoscopy procedure based on the estimated location of the one or more lumens.

When the endoscope navigates through the bronchial tree a lumen should normally be located centrally in the image to lower the risk that the endoscope collides with the walls of the bronchial tree. Consequently, by using an estimated location of a lumen a simple and effective way of estimating a quality measure is provided.

The processor may be configured to detect the lumen using an adaptive method such as a machine learning data architecture. Alternatively, the processor may be configured to detect the lumen using a non-adaptive method relying on static rules. As an example, the processor may be configured to detect a lumen by using a method comprising: finding a set of connected pixels having an intensity value below a first threshold. The first threshold may be an absolute threshold, or a threshold determined based on the average intensity in an image. A group of connected pixels may be a set of pixels, where each pixel shares an edge or a corner with at least one other pixel in the set of pixels. A lumen may be detected if a set of connected pixels is found having a size above a second threshold.

The quality measure may be presented to the user during the procedure e.g. on a display. Alternatively, the quality measure may be presented to the user after the procedure has been completed and/or stored in a memory connected to the processor of the image processing device.

In some embodiments, the processor is configured to estimate the location of the one or more lumens by providing the image to a machine learning data architecture trained to identify the location of lumens in endoscope images. Consequently, an effective and reliable way of determining positions of lumens is provided.

The machine learning data architecture may be a supervised machine learning architecture. The machine learning data architecture may be trained by obtaining a training data set comprising endoscope images of different parts of different bronchial trees and for each endoscope image having a human operator identify a lumen (if present) e.g. a human operator may for each image firstly specify if a lumen can be seen in the image (if the image sensor is pointing towards the wall of the bronchial tree no lumen is visible), and secondly the location of the lumen. The location of the lumen may be a center of the lumen or a circumference of the lumen. The circumference of the lumen may be a circle e.g. the smallest circle that encompasses the lumen or the largest circle that can be fully contained within the lumen. Alternatively, the circumference may be a curve substantially arranged above the border of the lumen. The processor may implement the machine learning data architecture, i.e. the processor may provide the image to the machine learning data architecture by processing the image using the machine learning data architecture. Alternatively, the processor may provide the image, a parameterized version of the image, or a dimensionally reduced version of the image to another processor e.g. outside of the image processing device, where said another processor implements the machine learning data architecture.

In some embodiments, the machine learning data architecture is an artificial neural network such as a deep structured learning architecture.

The machine learning data architectures may be U-Net convolutional network.

In some embodiments, the processor is configured to obtain a stream of images captured by the image sensor of the endoscope, process the stream of images to estimate the location of the one or more lumens in the stream of images, and determine the quality measure of the bronchoscopy based on the estimated location of the one or more lumens in the stream of images. Consequently, the quality measure may represent the quality of an entire procedure.

In some embodiments, the processor is further configured to obtain an optimum lumen location in the stream of images, and determine the quality measure based on both the optimum lumen location and the estimated location of the one or more lumens in the stream of images.

While it may generally be desirable to have a lumen arranged centrally, there may be situations where a lumen should not be arranged centrally e.g. if two lumens are present, then it may be desirable that each lumen is arranged with an offset to the center of image. Thus, by obtaining an optimum lumen location a more precise quality measure me be determined.

The optimum lumen location may be a zone of the image e.g. a zone centered in the center of image. The zone may have a circular or elliptical shape. Alternatively, the optimum lumen location may be a point in the image indicating the optimum location of a point of the lumen e.g. the center of the lumen. A value of the quality measure indicating a high quality may result if the location of the one or more lumens are close to the optimum lumen location and a value of the quality measure indicating a low quality may result if the one or more lumens are far away from the optimum lumen location. The quality measure may be based on a numerical number e.g. a number between 0 and 10. A sub quality measure may be determined for each image of the stream of images, wherein the quality measure is an average of the sub quality measures. The average may be a weighted average or an unweighted average.

In some embodiments, the processor is configured to continuously obtain optimum lumen locations. Consequently, different optimal lumen locations may be obtained as the endoscope navigates through the airways.

As an example, the bronchial tree may be divided into a number of sections and for each section optimum lumen location(s) may be specified, the processor may then estimate in which section of the bronchial tree the endoscope is present and retrieve the corresponding optimum lumen location(s). The optimum lumen locations may be provided by an experienced medical professional and stored in a memory unit e.g. a memory unit of the image processing device.

The type of location in the bronchial tree may specify if a single lumen or more than a single lumen is present e.g. if more than one lumen is present optimum lumen location may be enlarged.

In some embodiments, the processor is further configured to estimate the operational state of the endoscope, the operational state indicates if the endoscope is navigating through the bronchial tree or investigating an area of the bronchial tree, where the processor is configured to determine the quality measure based on both the estimated location of the one or more lumens and the estimated operational state of the endoscope. Consequently, a more precise quality measure may be determined.

In some embodiments, the processor is configured to estimate the operational state of the endoscope by processing the image or stream of images using a machine learning data architecture trained to determine based on endoscope images or streams of images if the operator is navigating through the bronchial tree or investigating an area of the bronchial tree. Consequently, an effective way of determining operational state is provided.

The machine learning data architecture may be a supervised machine learning architecture. The machine learning data architecture may be trained by obtaining a training data set comprising endoscope images from different bronchoscopy procedures and for each endoscope image having a human operator identify if the current image is from a part of the bronchoscopy procedure where the medical professional is navigating through the bronchial tree or investigating an area of the bronchial tree.

In some embodiments, the requirements for the location of the one or more lumens are more strict if it is estimated that the endoscope is navigating through the bronchial tree than if it is estimated that the endoscope is investigating an area of the bronchial tree.

As an example, there may be no requirements to the location of a lumen if it is estimated that the endoscope is investigating an area of the bronchial tree.

In some embodiments, a method for estimating a quality measure of a bronchoscopy procedure based on an image captured by an image sensor of an endoscope, the method comprising: obtaining an image captured by the image sensor of the endoscope; processing the image to estimate the location of one or more lumens in the stream of images, and determining a quality measure of the bronchoscopy based on the estimated location of the one or more lumens.

Figure 20:
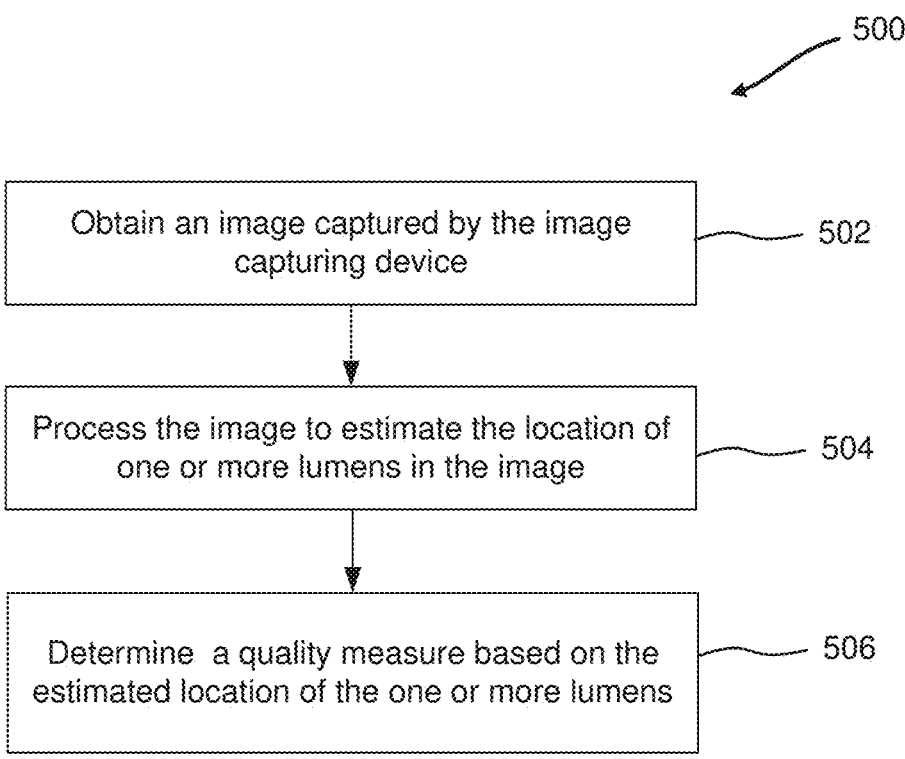
FIG. 20 is a flowchart of a further embodiment of a method for determining a quality of an endoscopic procedure.

FIG. 20 shows a flowchart 500 of a method for estimating a quality measure of a bronchoscopy procedure based on an image captured by an image sensor of an endoscope.

At 502 an image captured by the image sensor of the endoscope is obtained.

Next, at 504, the image is processed to estimate the location of one or more lumens in the stream of images.

Then, at 506, a quality measure of the bronchoscopy is determined based on the estimated location of the one or more lumens.

Figure 21A:
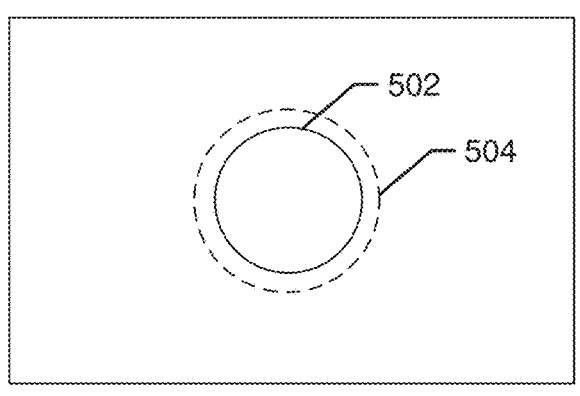
FIG. 21*a-c* show schematically images captured by an endoscope.
Figure 21B:
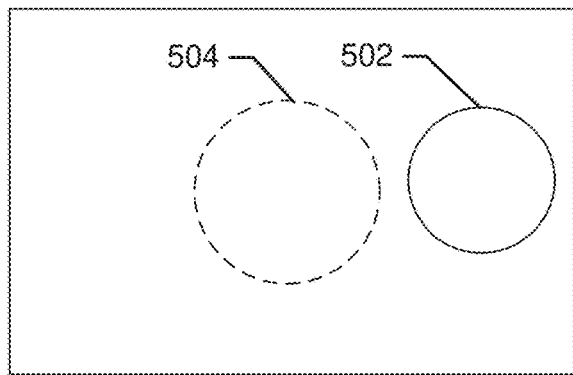
Figure 21C:
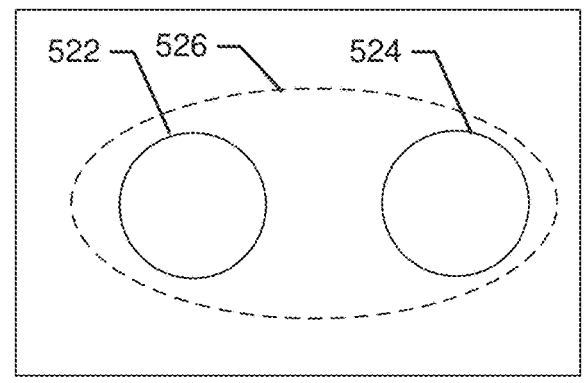

FIGS. 21a-c show schematically images captured by an image sensor of an endoscope. In FIGS. 21a and 21b, a single lumen 502 and an optimum lumen location 504 are shown. In FIG. 21a the lumen 502 is in the optimum lumen location and in FIG. 21b the lumen 502 is not in the optimum lumen location 502. These figures illustrate how to determine a quality measure based on the position of the lumen 502.

Referring to FIG. 21a, the optimum lumen location 504 is for this image arranged centrally, in a part of the bronchial tree where no branching is present. At least when the endoscope is navigating through the bronchial tree, the lumen should be arranged centrally to lower the risk that the endoscope's distal tip collides with the bronchial wall. The lumen 502 is arranged fully within the optimum lumen location 504, thus in this situation a high quality measure may be generated.

The optimum lumen location 504 might or might not be shown to the medical professional operating the endoscope i.e. the optimum lumen location 504 might only be available to the processing circuit 26 for determining the quality measure. However, the optimum lumen location 504 may be shown to the medical professional. As an example, if the images captured by the image sensor are displayed on a display unit, then the optimum lumen location 504 may be indicated on the display unit e.g. it may be overlaid the endoscope images.

The processor of the image processing device may be configured to estimate the operational state of the endoscope by processing the image or a stream of images using a machine learning data architecture trained to determine, based on endoscope images or streams of images, if the operator is navigating through the bronchial tree or investigating an area of the bronchial tree. Based on the estimated operational state, the optimal lumen location 504 may or may not be shown to the medical professional e.g. optimal lumen location 504 might only be displayed when it is estimated that the operator is navigating through the bronchial tree. This may be especially useful for training new medical professionals. Furthermore, by selectively displaying the optimum lumen location, the medical professional might not be distracted when investigating an area of the bronchial tree e.g. for a pathological condition.

FIG. 21b shows a situation where the lumen 502 is fully outside the optimum lumen location 504. In this situation a quality measure indicating a low quality may be generated.

FIG. 21c shows a typical view of the image sensor when the endoscope is arranged in a part of the bronchial tree where a branching is present. In FIG. 21c, two lumens, 522 and 524, and a lumen location 526, are shown. The lumens 522 and 524 are arranged fully within the optimum lumen location 526. In this situation a quality measure indicating a high quality may be generated. It can further be seen that the optimum lumen location 526 has been enlarged relative to the optimum lumen location 504.

Figure 22:
FIG. 22 shows an image of a training dataset.

FIG. 22 illustrates how a machine learning data architecture may be trained to estimate locations of one or more lumens in endoscope images. Shown is a single image 530 of a training data set. A typical training data set comprises endoscope images of different parts of different bronchial trees, i.e. endoscope images from a significant number of endoscope examinations. To train the machine learning data architecture a human operator indicates the location of lumens, in this concrete example two lumens 532 and 534. The location of the lumens is indicated by drawing up the periphery of each lumen.

Figure 23A:
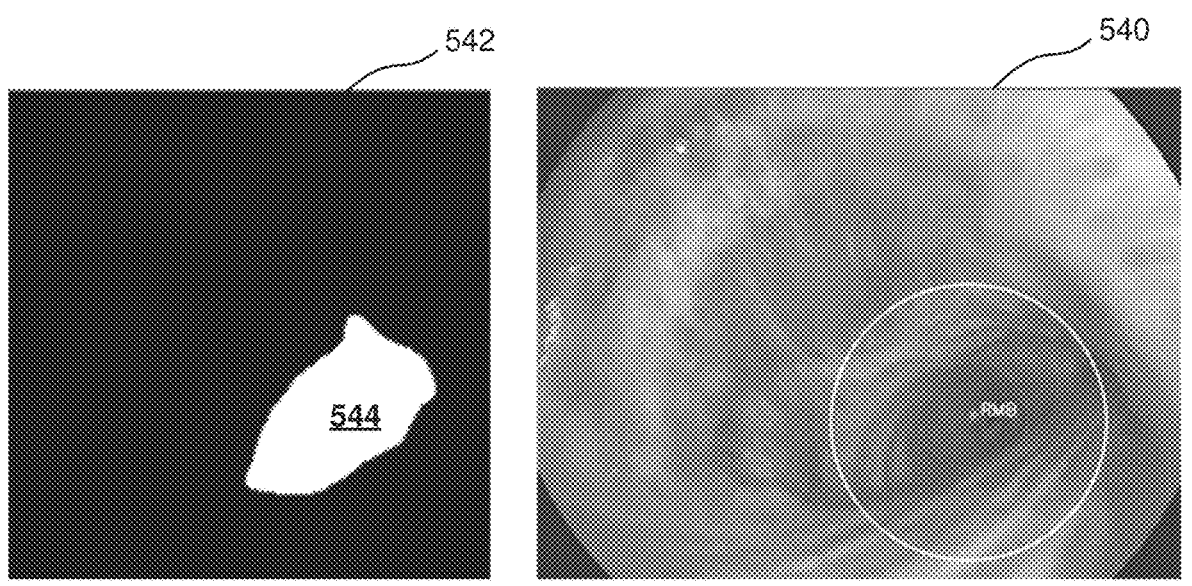
FIG. 23*a-b* show images to be evaluated and the output after the images are evaluated.
Figure 23B:
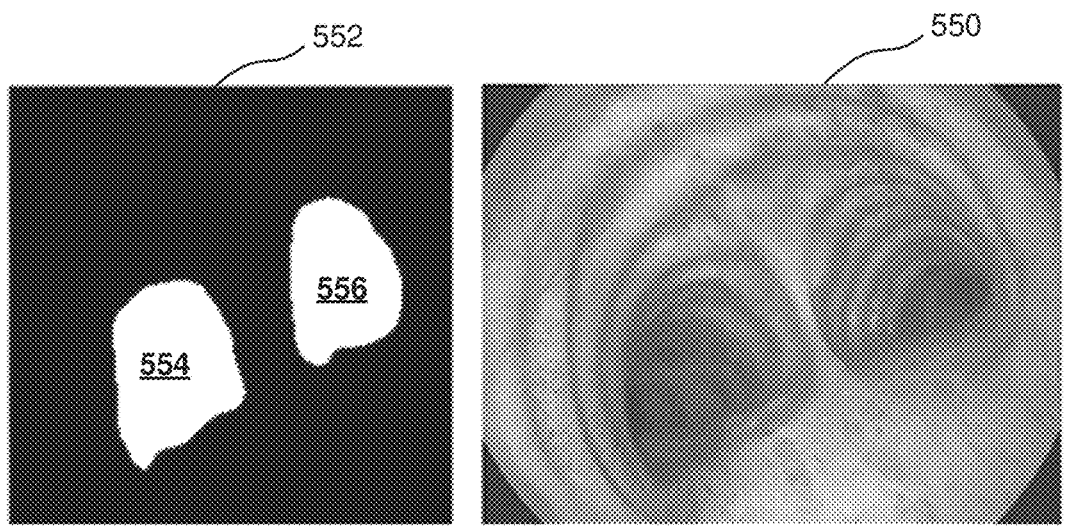

FIGS. 23a-b illustrate how one or more lumen may be identified in endoscope images. The one or more lumens are identified using a machine learning data architecture trained to estimate locations of one or more lumens in endoscope images as disclosed in relation to FIG. 22. In FIG. 23a, the input image 540 is shown to the right and the output image 542 from the machine learning data architecture is shown to the left. As the machine learning data architecture has been trained to estimate the periphery of a lumen, the location and the periphery of a lumen 544 are identified in the output image 542. FIG. 23b shows another example, where the input image 550 is shown to the right and the output image 552 from the machine learning data architecture is shown to the left. In this example, the location of two lumens 554 and 556 are estimated.

The processing circuit 26 estimates the location and size and/or shape of lumens by identifying, in the output images, the pixels corresponding to the transitions from black to white. Alternatively, rather than first generating an output image and then estimating the location and size and/or shape of lumens from the output image, the processing circuit 26 may extract from the machine learning data architecture the characteristics of the lumens, said characteristics being how the machine learning data architecture identified the lumens from training images. The characteristics may comprise, for example, a pixel location corresponding to the center of the lumen and a value corresponding to its size. The characteristics may comprise, for example, a value indicative of a shape from a predetermined plurality of shapes. The shapes may correspond to an orientation of a cross-section of a section of the lumen relative to a longitudinal axis of the section of the lumen, which might indicate curvature of the section or a following section.

The characteristics may comprise, for example, a relative position vis a vis a prior image. The differences between images, for example expanding peripheries, may indicate a direction and speed of travel of the distal tip and may also be used to determine a position of the tip. Prior images, evaluated earlier in the procedure, may be used to estimate an overall size of the lumen and this information may be used to evaluate subsequent images. It has been found, for example, that the machine learning data architecture is more accurate assessing images of a subsequent procedure performed on a patient, if those images are incorporated into the training images, than on a new patient. Thus, it is also possible based on a proximal section of the lumen to increase the detection accuracy in a distal section of the lumen.

Furthermore, the processing circuit 26 may, upon determining the location of the tip of the endoscope and the direction of travel, modify (e.g. zero out) the weights of sections of the lumen which have been passed already by the tip of the endoscope, and the removal of these sections from the analysis of the subsequent images improves the accuracy (and reduces computational costs) of the evaluation of the subsequent images while the endoscope is moving in the same direction. When the direction of travel reverses, the weights are reset until the processing circuit 26 determines that some sections are not viable (e.g. have been passed already by the tip of the endoscope).

The following items are further variations and examples of the embodiments described with reference to FIGS. 1a, 1b, 2 to 5, and 20 to 23b.

1. An image processing device for estimating a quality measure of a bronchoscopy procedure performed using an endoscope, the endoscope comprising an image sensor, the image processing device comprising a processor operationally connectable to the image sensor, wherein the processor is configured to: obtain an image captured by the image sensor of the endoscope; process the image to estimate the location of one or more lumens in the image, and determine a quality measure of the bronchoscopy based on the estimated location of the one or more lumens.

2. An image processing device according to item 1, wherein the processor is configured to estimate the location of the one or more lumens by providing the image to a machine learning data architecture trained to identify the location of lumens in endoscope images.

3. An image processing device according to items 1 or 2, the processor is configured to obtain a stream of images captured by the image sensor of the endoscope, process the stream of images to estimate the location of the one or more lumens in the stream of images, and determine the quality measure of the bronchoscopy based on the estimated location of the one or more lumens in the stream of images.

4. An image processing device according to item 3, wherein the processor is further configured to obtain an optimum lumen location in the stream of images, and determine the quality measure based on both the optimum lumen location and the estimated location of the one or more lumens in the stream of images.

5. An image processing device according to item 4, wherein the processor is configured to continuously obtain optimum lumen locations.

6. An image processing device according to item 5, wherein the processor is configured to estimate the location of the endoscope or the type of location in the bronchial tree and based on the estimated location or type of location is configured to determine optimum lumen locations.

7. An image processing device according to any one of items 1 to 6, wherein the processor is further configured to estimate the operational state of the endoscope, the operational state indicates if the endoscope is navigating through the bronchial tree or investigating an area of the bronchial tree and wherein the processor is configured to determine the quality measure based on both the estimated location of the one or more lumens and the estimated operational state of the endoscope.

8. An image processing device according to item 7, wherein the processor is configured to estimate the operational state of the endoscope by processing the image or stream of images using a machine learning data architecture trained to determine based on endoscope images or streams of images if the operator is navigating through the bronchial tree or investigating an area of the bronchial tree.

9. An image processing device according to items 7 or 8, wherein the requirements for the location of the one or more lumens are more strict if it is estimated that the endoscope is navigating through the bronchial tree than if it is estimated that the endoscope is investigating an area of the bronchial tree.

10. A display unit for displaying images obtained by an image sensor of an endoscope, wherein the display unit comprises an image processing device according to any one of items 1 to 9.

11. An endoscope system comprising an endoscope and an image processing device according to any one of items 1 to 9, wherein the endoscope has an image sensor and the processor of the image processing device is operationally connectable to the image sensor of the endoscope.

12. An endoscope system according to item 11, wherein the image processing device forms part of a display unit according to item 10.

13. A method for estimating a quality measure of a bronchoscopy procedure based on an image captured by an image sensor of an endoscope, wherein the method comprises the steps of: obtain an image captured by the image sensor of the endoscope; process the image to estimate the location of one or more lumens in the stream of images, determine a quality measure of the bronchoscopy based on the estimated location of the one or more lumens.

14. A computer program product comprising program code means adapted to cause a data processing system to perform the steps of the method according to item 13, when said program code means are executed on the data processing system.

15. A computer program product according to item 14, wherein said computer program product comprises a non-transitory computer-readable medium having stored thereon the program code means.

As described above with reference to FIGS. 1a, 1b, 2 to 5 and below with reference to FIGS. 24 to 29, the visualization system can document an endoscopic procedure, illustratively a bronchoscopy procedure. A processor comprises processing instructions configured to execute the method, which comprises: obtaining a model of the bronchial tree; obtaining a stream of images captured by the image sensor of the endoscope; continuously obtaining estimates of the location of the endoscope in the model of the bronchial tree during the bronchoscopy; and based on at least three estimates of the location of the endoscope in the model of the bronchial tree generating a report documenting the bronchoscopy procedure. Consequently, by obtaining a model of the bronchial tree and creating a report based on estimated location of the endoscope in the model, a bronchoscopy may effectively be documented. Of course, the same logic can be used to document any other endoscopic procedure using a corresponding neural network model and proximity suppression map.

The model of the bronchial tree may be a generic model created to correspond to the anatomy of most bronchial tree. However, it may also be uniquely created for a particular patient e.g. based on other type of medical imaging such as CT, MRI or a previous bronchoscopy.

The location of the endoscope in the model of the bronchial tree may specify a particular part of the bronchial tree e.g. a particular branch of the bronchial tree. The location of the endoscope may be determined using any method such as magnetic tracking or image-based techniques such as machine learning methods e.g. as disclosed above and/or in PCT/EP2021/064985. The imaged based technique may attempt to recognize anatomical reference positions in the endoscope images. Once an anatomical reference position has been recognized it may be determined that the endoscope is at the same anatomical reference position in the model of the bronchial tree.

The report may be generated after the endoscopic procedure has been concluded. Alternatively/additionally, the report may be generated/updated continuously during the bronchoscopy and displayed to the medical professional during the bronchoscopy e.g. in connection with endoscope images captured by the image sensor. The report may be stored in a memory of the image processing device. The report may be stored in a single data file. Alternatively, different elements of the report may be stored in different data files. The report may comprise or consist of one or more images. The report may be automatically generated e.g. without user input. The report may be based on more than at least three estimates of the location of the endoscope in the model of the bronchial tree e.g. the report may be based on all of the obtained estimates of the location of the endoscope in the model of the bronchial tree. The report may comprise a quality measure of the bronchoscopy. The quality measure may be generated based on the at least three estimates of the location of the endoscope in the model of the bronchial tree. The quality measure may indicate a percentage of the bronchial tree that has been investigated. The percentage may be calculated relative to the full bronchial tree or a part of the bronchial tree dependent on the particular type of bronchoscopy being performed. The quality measure may further be based on the time used for performing the bronchoscopy.

In some embodiments, the report indicates the locations that have been visited by the endoscope during the bronchoscopy procedure.

In some embodiments, the report comprises an image of the model of the bronchial tree, where the parts of the model of the bronchial tree that have been visited by the endoscope are marked in the image of the model of the bronchial tree. Consequently, an effective way of documenting a bronchoscopy is provided.

As an example the parts of the bronchial tree that have not been visited by the endoscope may be displayed with a first color and the parts of the bronchial tree that have been visited may be shown with a second color different from the first color. One or more of the parts that have been visited may be a part where no part of the endoscope is present e.g. a part from where the endoscope has been withdrawn.

In some variations of the present embodiment, the processor is configured to store, in response to a user input, an image of the stream of images together with first data indicative of the location of the endoscope in the model of the bronchial tree when the image was recorded, and wherein the generated report comprises the image and the first data. Consequently, it may be effectively documented where the endoscope was present when the image was captured. As an example, if the image shows a potential pathological structure, and a test on sample subsequently confirms that the structure is pathological, the report may be used to allow the medical professional to easily revisit the structure and thereby secure effective treatment.

The user input may be received from the handle of the endoscope e.g. the handle may comprise an input unit that can be used for capturing images. The input unit may be operationally connectable to the processor. Alternatively/additionally, the user input may be received from a display showing the endoscope images.

In some variations of the present embodiment, the processor is configured to store a first stream of images, the first stream of images being at least a part of the stream of images and for a plurality of images of the first stream of images store second data indicative of the locations of the endoscope in the model of the bronchial tree when the plurality of images where recorded, and wherein the generated report comprises the first stream of images and the second data.

Today most medical professionals prefer to use endoscope still images when documenting procedures as it too complex and time consuming to navigate through a video consisting of a stream of images. However, by storing the second data logging the locations of the endoscope, it may become easier to navigate in a clinical video.

The first stream of images may represent the entire bronchoscopy. Alternatively, the first stream of images may represent only a part of the bronchoscopy. The first stream of images may be recorded in response to a user input from input unit e.g. in response to an input unit at the endoscope handle.

In some variations of the present embodiment, the processor is operationally connectable to a display wherein the processor is configured to control the display to display the generated report.

In some variations of the present embodiment, the processor is operationally connectable to an input unit, and wherein the processor is configured to: control the display to display an image of the model of the bronchial tree; receive an input signal from the input unit indicating part of the model of the bronchial tree; based on the input signal and the second data identify a first image of the first stream of images that is recorded at the indicated part of the model of the bronchial tree or in proximity to the indicated part; and control the display to display the first image. Consequently, a medical professional may effectively navigate through a clinical video.

If the endoscope twice has visited the indicated part, then two images may be shown. As an example, if the indicated part is a part of the upper bronchial tree, the endoscope may have visited the part both when the endoscope enters the bronchial tree and is withdrawn from the bronchial tree.

In some variations of the present embodiment, the processor is configured to control the display to start replaying the first stream of images from the first image. The processor may be configured to replay the first stream of images directly or in a response to a further user input.

Embodiments of a method for documenting a bronchoscopy procedure performed using an endoscope are also provided herein. The method comprises: obtaining a model of the bronchial tree; obtaining a stream of images captured by the image sensor of the endoscope; continuously obtaining estimates of the location of the endoscope in the model of the bronchial tree during the bronchoscopy; and based on at least three estimates of the location of the endoscope in the model of the bronchial tree generating a report documenting the bronchoscopy procedure.

Figure 24:
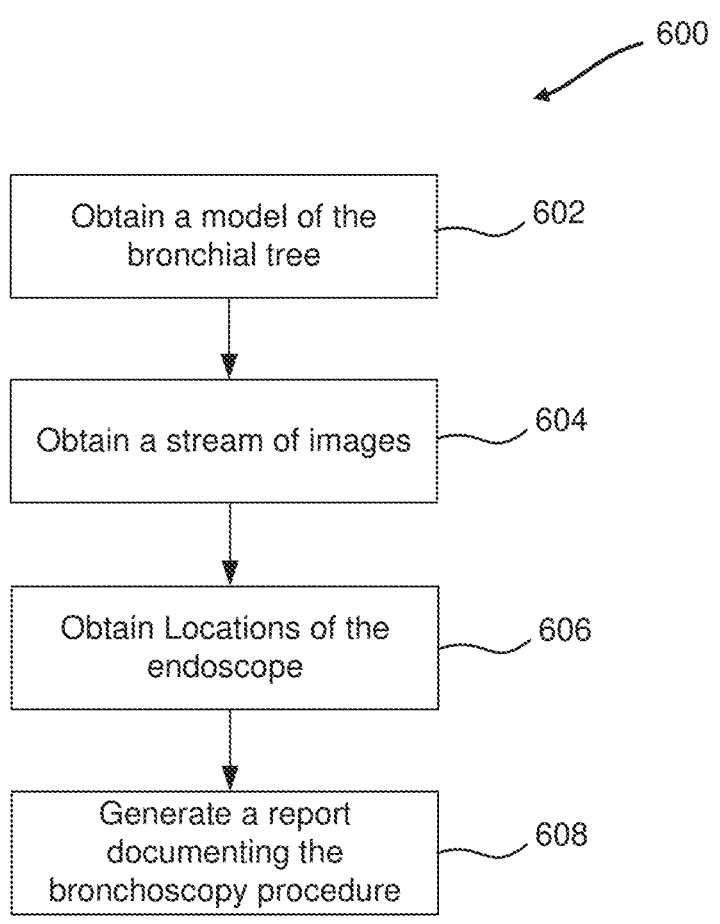
FIG. 24 is a flowchart of an embodiment of a method for documenting an endoscopic procedure.

FIG. 24 shows a flowchart 600 of an example of the foregoing method for documenting a bronchoscopy procedure performed using an endoscope.

At 602, a model of the bronchial tree is obtained.

At 604, a stream of images captured by the image sensor of the endoscope is obtained.

At 606, estimates of the location of the endoscope in the model of the bronchial tree during the bronchoscopy are continuously obtained.

At 608, based on at least three estimates of the location of the endoscope in the model of the bronchial a report documenting the bronchoscopy procedure is generated.

Figure 25:
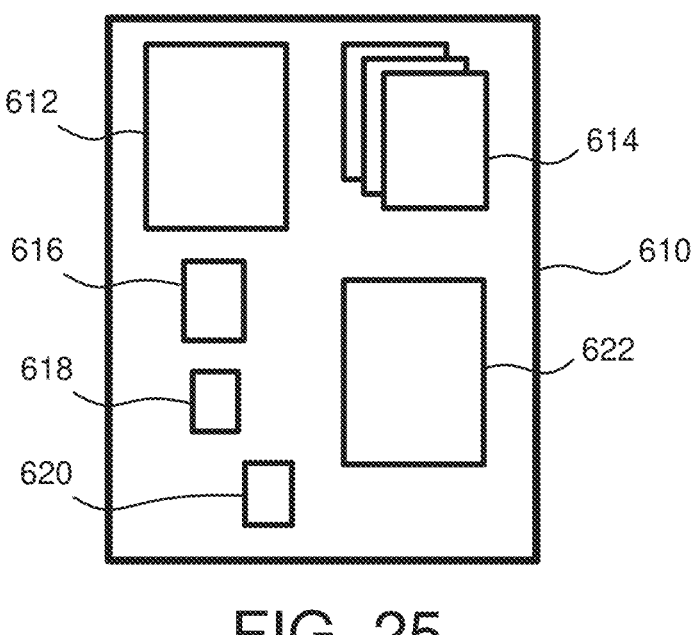
FIG. 25 is a schematic representation of a report in accord with the method of FIG. 24.

FIG. 25 shows schematically a report 610 documenting the bronchoscopy procedure according to an embodiment of the disclosure. The report comprises an image 612 of the model of the bronchial tree, where the parts of the model of the bronchial tree that have been visited by the endoscope are marked in the image. Thus, the image 612 indicates the locations that have been visited by the endoscope during the bronchoscopy procedure. The report 610 may further comprise one or more images 614 of a stream of images. For each image of the one or more images 614 the report 610 further comprises first data 616 indicative of the location of the endoscope in the model of the bronchial tree when that image was recorded. The report 610 may further comprise a quality measure 618 of the bronchoscopy. The report may further comprise a first stream of images 622 and second data 620 indicative for a plurality of images of the first stream of images 622 of the locations of the endoscope in the model of the bronchial tree when the plurality of images where recorded.

Figures 26A, 26B:
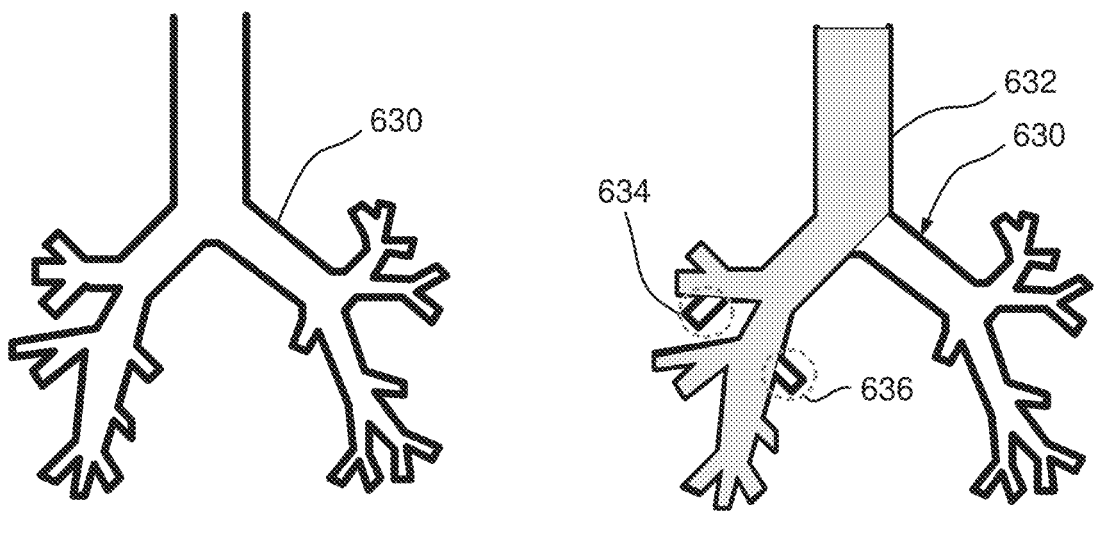
FIG. 26*a-b* are views of a model included in the report of FIG. 25.

FIGS. 26a-b show images 630 of a model of the bronchial tree. In other embodiments, the images of the model of the bronchial tree may be provided with more or fewer details. The model of the bronchial tree may be a generic model created to correspond to the anatomy of most patients. However, the model may also be uniquely created for a particular patient e.g. based on other type of medical imaging such as CT, MRI or a previous bronchoscopy. FIG. 26a shows the image before a bronchoscopy has been started, where all parts of the bronchial tree are shown in a first colour (white). FIG. 26b shows the image after a bronchoscopy of the right part of the bronchial tree has been performed (the right part of the bronchial tree is normally shown to the left in an anatomical representation of the bronchial tree). In FIG. 26b the parts 632 of the model of the bronchial tree that have been visited by the endoscope are marked with a second color (gray). It can be seen that two parts, 634 and 636, of the bronchial tree have been missed. Thus, if the medical professional is presented with a report comprising the image in FIG. 26b, the medical professional may recognize that the parts 634 and 636 must be examined to prevent that any pathological conditions are overlooked.

Figure 27A:
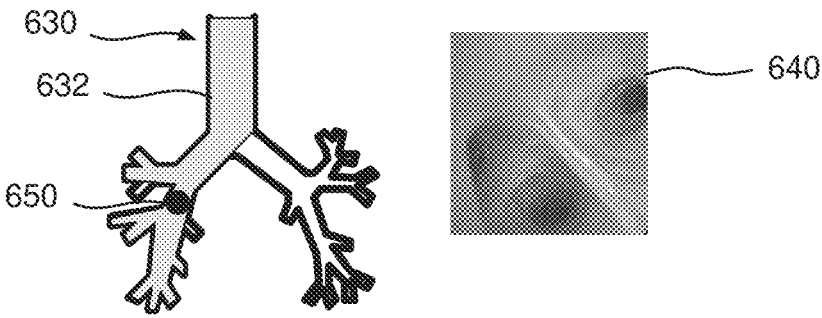
FIG. 27*a-b* are views of the model and an image corresponding to a location shown in the model.

FIG. 27a shows an endoscope image 640 recorded during a bronchoscopy procedure according to an embodiment of the disclosure. Also shown is an image of the model 630 of the bronchial tree, where parts of the model, denoted by numeral 632, are marked to indicate that they have been visited by the endoscope. A dot 650 illustrates where the endoscope was located when the image 640 was recorded. The position of the dot may be determined by first data forming part of a report documenting the bronchoscopy procedure.

Figure 27B:
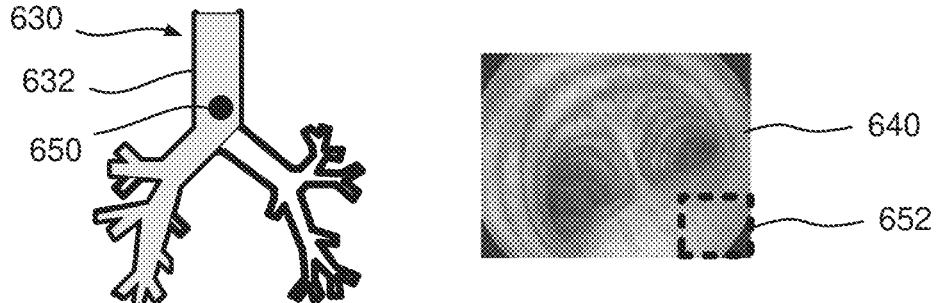

FIG. 27b corresponds to FIG. 27a with the difference that the image 640 is recorded at another position indicated by the dot 650. Furthermore, a box 652 schematically illustrates that the endoscope image 640 may be augmented with the image of the model of the bronchial tree 630. As an example, the image of the model of the bronchial tree 630 may be overlayed onto the endoscope image 640 in the corner where the box 652 is located. The image of the model of the bronchial tree 630 may be made semitransparent before being overlayed the endoscope image 640.

Figure 28:
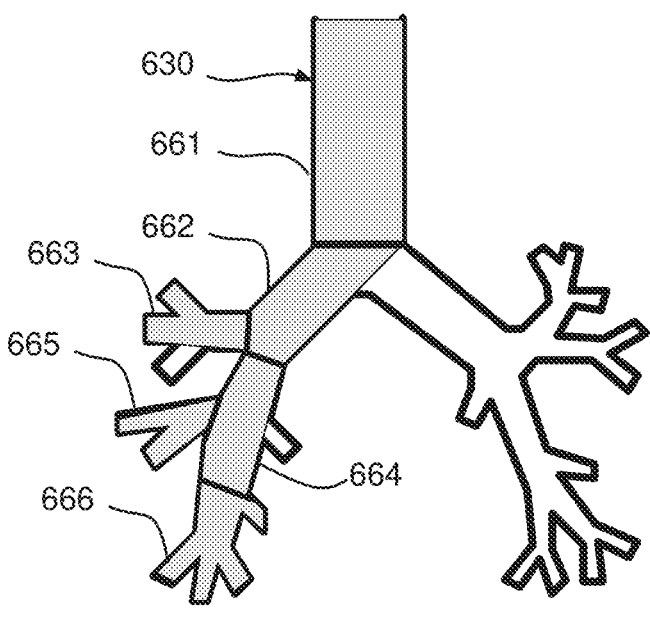
FIG. 28 is a view of a model of a bronchial tree illustrating segments investigated and segments not investigated.

FIG. 28 illustrates schematically embodiments in which the images are used to effectively navigate through a clinical video. Shown is the model 630 of the bronchial tree. The model has been divided into a number of parts 661-666. In this embodiment, only the right part of the bronchial tree is being investigated. Thus, only the right part of the bronchial tree has been divided into parts. However, in other embodiments, the entire bronchial tree is being investigated, whereby also the right part will be divided into parts.

Figure 29:
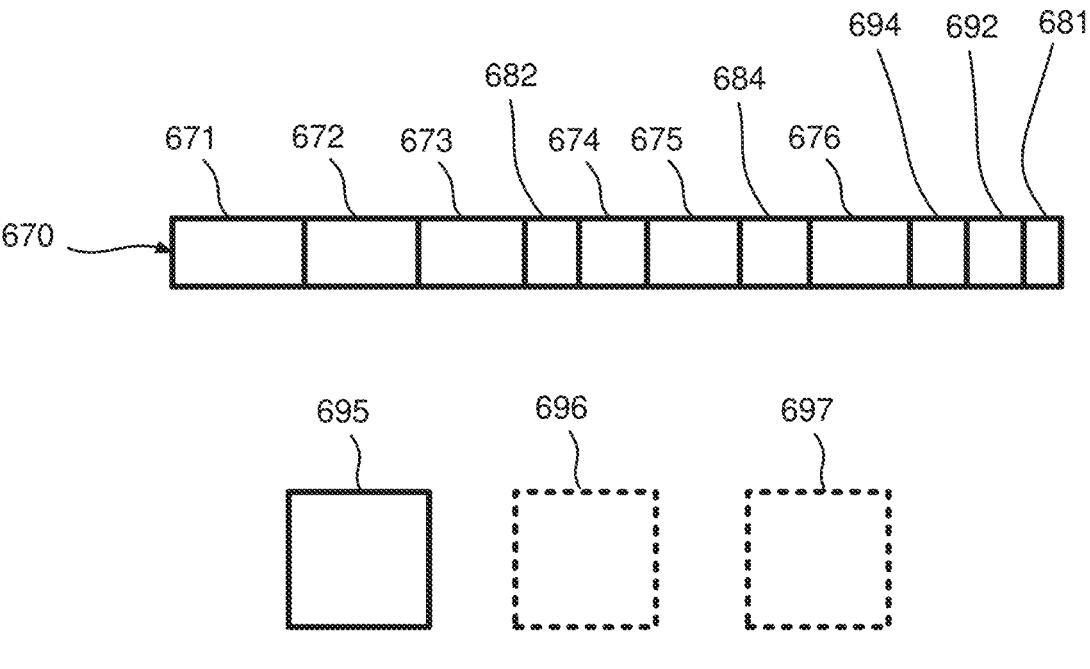
FIG. 29 is a schematic representation of images arranged to represent the endoscopic procedure in the order the images were obtained.

FIG. 29 shows schematically a first stream of images 670 representing the entire bronchoscopy. During the bronchoscopy for a plurality of images of the first stream of images 670 second data is stored indicative of the locations of the endoscope in the model of the bronchial tree when the plurality of images where recorded. As an example, the second data may be generated for the first image recorded after the endoscope has entered a new part of the bronchial tree. Thus, the second data may be stored for the first image recorded after the endoscope has entered the parts 661-666. The second data may be used to divide the first stream of images 670 into a plurality of sections 671-676, 682, 684, 694, 692, and 681. In the sections 671-676 the endoscope is examining/propagating, respectively, through the parts 661-666 of the bronchial tree. Sections 682 and 692 correspond to part 662, sections 684 and 694 correspond to part 664, and section 681 corresponds to part 661.

The order of the sections may be indicative of the direction of travel. Thus, the endoscope may travel back to part 662 (section 682) before proceeding to parts 664 and 665, and then travel back to part 664 (section 684) before proceeding to part 666. The endoscope may then reverse direction and travel back through parts 664, 662, and 661 (sections 694, 692, and 691) before proceeding. The sections of the first stream of images 670 thus illustrate the procedure, including back and forth movements of the endoscope and inspection of the parts accessed by the endoscope.

In some embodiments, the model of the bronchial tree 630 may be displayed and an input signal may be received indicating a part of the model of the bronchial tree. Based on the input signal and the second data a first image of first stream of images 670 that is recorded at the indicated part of the model of the bronchial tree or in proximity to the indicated part may be found and displayed. As an example, the model of the bronchial tree 630 may be displayed on a touch display, where a user is provided with the possibility to select any one of parts 661-666. If the user select part 661, the first image from section 671 may be displayed in a first part 695 of the touch display and the first image from the section 681 may be displayed in a second part 696 of the touch display. The user may then select one of the images whereby either the section 671 or the section 681 of the first stream is replayed. Correspondingly, if the user selects the part 662, the first image from the section 672 may be displayed in the first part 695 of the touch display, the first image from the section 682 may be displayed in the second part 696 of the touch display, and the first image from the section 692 may be displayed in a third part 697 of the display. The user may then select one of the images whereby either the section 672, the section 682 or the section 692 of the first stream is being replayed.

The following items are further variations and examples of the embodiments described with reference to FIGS. 1*a*, 1*b*, 2 to 5, and FIGS. 24 to 29.

1. An image processing device for documenting a bronchoscopy procedure performed using an endoscope, the endoscope comprising an image sensor, the image processing device comprising a processor operationally connectable to the image sensor, wherein the processor is configured to: obtain a model of the bronchial tree; obtain a stream of images captured by the image sensor of the endoscope; continuously obtain estimates of the location of the endoscope in the model of the bronchial tree during the bronchoscopy; and based on at least three estimates of the location of the endoscope in the model of the bronchial tree generate a report documenting the bronchoscopy procedure.

2. An image processing device according to item 1, wherein the report indicates the locations that have been visited by the endoscope during the bronchoscopy procedure.

3. An image processing device according to items 1 or 2, wherein the report comprises an image of the model of the bronchial tree, where the parts of the model of the bronchial tree that have been visited by the endoscope are marked in the image of the model of the bronchial tree.

4. An image processing device according to any one of items 1 to 3, wherein the processor is configured to store in response to a user input an image of the stream of images together with first data indicative of the location of the endoscope in the model of the bronchial tree when the image was recorded, and wherein the generated report comprises the image and the first data.

5. An image processing device according to any one of items 1 to 4, wherein the processor is configured to store a first stream of images, the first stream of images being at least a part of the stream of images and for a plurality of images of the first stream of images store second data indicative of the locations of the endoscope in the model of the bronchial tree when the plurality of images where recorded, and wherein the generated report comprises the first stream of images and the second data.

6. An image processing device according to any one of items 1 to 5, wherein the processor is operationally connectable to a display wherein the processor is configured to control the display to display the generated report.

7. An image processing device according to items 5 and 6, wherein the processor is operationally connectable to an input unit, and wherein the processor is configured to: control the display to display an image of the model of the bronchial tree; receive an input signal from the input unit indicating part of the model of the bronchial tree; based on the input signal and the second data identify a first image of first stream of images that is recorded at the indicated part of the model of the bronchial tree or in proximity to the indicated part; and control the display to display the first image.

8. An image processing device according to items 7, wherein the processor is configured to control the display to start replaying the first stream of images from the first image.

9. An image processing device according to items 8 or 7, wherein the display is a touch display incorporating the input unit.

10. A display unit for displaying images obtained by an image sensor of an endoscope, wherein the display unit comprises an image processing device according to any one of items 1 to 9.

11. An endoscope system comprising an endoscope and an image processing device according to any one of items 1 to 9, wherein the endoscope has an image sensor and the processor of the image processing device is operationally connectable to the image sensor of the endoscope.

12. An endoscope system according to item 11, wherein the image processing device forms part of a display unit according to item 10.

13. A method for documenting a bronchoscopy procedure performed using an endoscope, the endoscope comprising an image sensor, wherein the method comprises: obtaining a model of the bronchial tree; obtaining a stream of images captured by the image sensor of the endoscope; continuously obtaining estimates of the location of the endoscope in the model of the bronchial tree during the bronchoscopy; and based on at least three estimates of the location of the endoscope in the model of the bronchial tree generating a report documenting the bronchoscopy procedure.

14. A computer program product comprising program code means adapted to cause a data processing system to perform the steps of the method according to item 13, when said program code means are executed on the data processing system.

15. A computer program product according to item 14, wherein said computer program product comprises a non-transitory computer-readable medium having stored thereon the program code means.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

The term "comprising," "including," and "having," and variations thereof, are open transition terms that specify the presence of stated features, integers, steps or components but do not preclude the presence or addition of one or more other features, integers, steps, components or groups thereof. By contrast, the term "consisting" is a closed transition term that precludes the presence or addition of one or more other features, integers, steps, components or groups thereof.

We claim:

1. An image processing device to facilitate an endoscopic procedure using an endoscope having an image sensor configured to generate images, the image processing device comprising:

a housing; and a processing circuit in the housing, the processing circuit including a processor and memory, the memory comprising a neural network model and proximity suppression logic, the neural network model comprising a single-pass neural network model trained with training images corresponding to the endoscopic procedure and defining anatomic references observable in the training images, the processor being configured to process the neural network model and the proximity suppression logic, wherein the neural network model is configured to process the images, to detect the anatomic references in the images, and to output a set of anatomic references including identifiers and confidence values representing the likelihoods that the anatomic reference identifiers are correct, and wherein the proximity suppression logic is configured to change the confidence values of the anatomic references in the set of anatomic references based on a prior position of the endoscope to identify an anatomic reference indicative of the current position of the endoscope.

2. The image processing device of claim 1, wherein the proximity suppression logic comprises a proximity suppression map including anatomical references and weights corresponding to the anatomical references, the weights predetermined based on a proximity of an anatomical reference to the other anatomical references, wherein the proximity suppression logic matches the prior position of the endoscope with one of the anatomical references in the map and changes the confidence values by multiplying the confidence values and the respective weights.

3. The image processing device of claim 1, further comprising an organ model including representations of lumens of organs of a patient to be examined.

4. The image processing device of claim 3, further comprising graphical user interface (GUI) logic configured to present the organ model with a display screen communicatively connected to the image processing device, wherein the GUI logic is additionally configured to present with the display screen an indication of the current position of the endoscope.

5. The image processing device of claim 4, further comprising a medical device interface configured to receive the images from the endoscope, the image processing device configured to determine, based on the medical device interface, a type of endoscopic procedure and to select the organ model, from two or more organ models stored in the memory, based on the type of the endoscopic procedure.

6. The image processing device of claim 4, wherein the image processing device is further configured to determine a route comprising a plurality of anatomic references.

7. The image processing device of claim 6, wherein the image processing device is further configured to determine whether the current position of the endoscope is on the route and output a warning indication if the current position is not on the route.

8. The image processing device of claim 1, wherein the image processing device is configured to repeatedly store in a prior position database a position indication of the current position of the endoscope as the endoscope is moved during the endoscopic procedure and the current position changes, the position indication comprising at least one of the current position of the endoscope and/or the anatomic reference indicative of the current position of the endoscope, and the prior position database containing the position indications generated during the endoscopic procedure.

9. The image processing device of claim 8, wherein the image processing device is configured to determine, by comparing the position indications in the prior position database with the position indication of the current position, if the current position of the endoscope matches a prior position of the endoscope.

10. The image processing device of claim 8, wherein the image processing device is configured to generate a report documenting each of the position indications in the database.

11. The image processing device of claim 10, wherein the report depicts an organ model with markings reflecting prior endoscope positions stored in the prior position database.

12. The image processing device of claim 10, wherein the processor is configured to store, in response to a user input, an image together with first data indicative of a position of the endoscope in an organ model when the image was recorded, and wherein the report comprises the image and the first data.

13. An endoscope system comprising:

the endoscope; and an image processing device according to claim 1.

14. The endoscope system of claim 13, further comprising a display screen.

15. The endoscope system of claim 13, further comprising a physical model of an organ of the human body, the organ comprising lumens and the physical model comprising model lumens, the physical model being a three-dimensional model, wherein the neural network model is trained with training images corresponding to the endoscopic procedure performed in the model lumens of the physical model.

16. The endoscope system of claim 15, wherein the physical model comprises visual markers detectable with the endoscope during the endoscopic procedure.

* * * * *